United States Patent
Jensen et al.

(10) Patent No.: US 8,121,687 B2
(45) Date of Patent: Feb. 21, 2012

(54) CARDIAC MOTION CHARACTERIZATION BY STRAIN MEASUREMENT

(75) Inventors: Marc Jensen, Los Gatos, CA (US); Todd Thompson, San Jose, CA (US); Olivier Colliou, Los Gatos, CA (US); George M. Savage, Portola Valley, CA (US); Mark J. Zdeblick, Portola Valley, CA (US); Jeremy Frank, San Francisco, CA (US); Lawrence W. Arne, Redwood City, CA (US); Robert White, Stanford, CA (US)

(73) Assignee: Proteus Biomedical, Inc., Redwood City, CA (US)

(*) Notice: Subject to any disclaimer, the term of this patent is extended or adjusted under 35 U.S.C. 154(b) by 898 days.

(21) Appl. No.: 11/718,201

(22) PCT Filed: Oct. 31, 2005

(86) PCT No.: PCT/US2005/039535
§ 371 (c)(1),
(2), (4) Date: May 27, 2008

(87) PCT Pub. No.: WO2006/050385
PCT Pub. Date: May 11, 2006

(65) Prior Publication Data
US 2008/0255629 A1    Oct. 16, 2008

Related U.S. Application Data

(60) Provisional application No. 60/624,427, filed on Nov. 1, 2004, provisional application No. 60/638,247, filed on Dec. 20, 2004, provisional application No. 60/638,947, filed on Dec. 22, 2004, provisional application No. 60/667,749, filed on Mar. 31, 2005.

(51) Int. Cl.
*A61N 1/18* (2006.01)

(52) U.S. Cl. .......... 607/17; 607/6; 607/18; 607/19; 607/22

(58) Field of Classification Search .......... 607/4–6, 607/17–19, 122, 127
See application file for complete search history.

(56) References Cited

U.S. PATENT DOCUMENTS

| | | | |
|---|---|---|---|
| 3,971,363 A | 7/1976 | Fletcher et al. | |
| 4,911,016 A * | 3/1990 | Miyazaki et al. | 73/766 |
| 5,178,151 A | 1/1993 | Sackner et al. | |
| 5,241,964 A | 9/1993 | McQuilkin et al. | |
| 5,496,361 A | 3/1996 | Moberg et al. | |
| 5,868,678 A | 2/1999 | Brunner et al. | |
| 5,941,904 A * | 8/1999 | Johnston et al. | 607/19 |
| 6,285,906 B1 * | 9/2001 | Ben-Haim et al. | 607/4 |
| 6,406,420 B1 | 6/2002 | McCarthy et al. | |
| 2003/0004440 A1 | 1/2003 | Brenneman et al. | |
| 2005/0203579 A1 * | 9/2005 | Sowelam et al. | 607/6 |

OTHER PUBLICATIONS

Flaherty, "Swiss startup puts MEMS sensor in contact lens" UK Technology Startups; www.electronicsweekly.com (2010) 2 pp.

* cited by examiner

*Primary Examiner* — Niketa Patel
*Assistant Examiner* — Rex R Holmes
(74) *Attorney, Agent, or Firm* — Bret E. Field; Bozicevic, Field & Francis LLP

(57) ABSTRACT

Methods for evaluating motion of a cardiac tissue location, e.g., heart wall, are provided. In the subject methods, timing of a signal obtain from a strain gauge stably associated with the tissue location of interest is employed to evaluate movement of the cardiac tissue location. Also provided are systems, devices and related compositions for practicing the subject methods. The subject methods and devices find use in a variety of different applications, including cardiac resynchronization therapy.

31 Claims, 41 Drawing Sheets

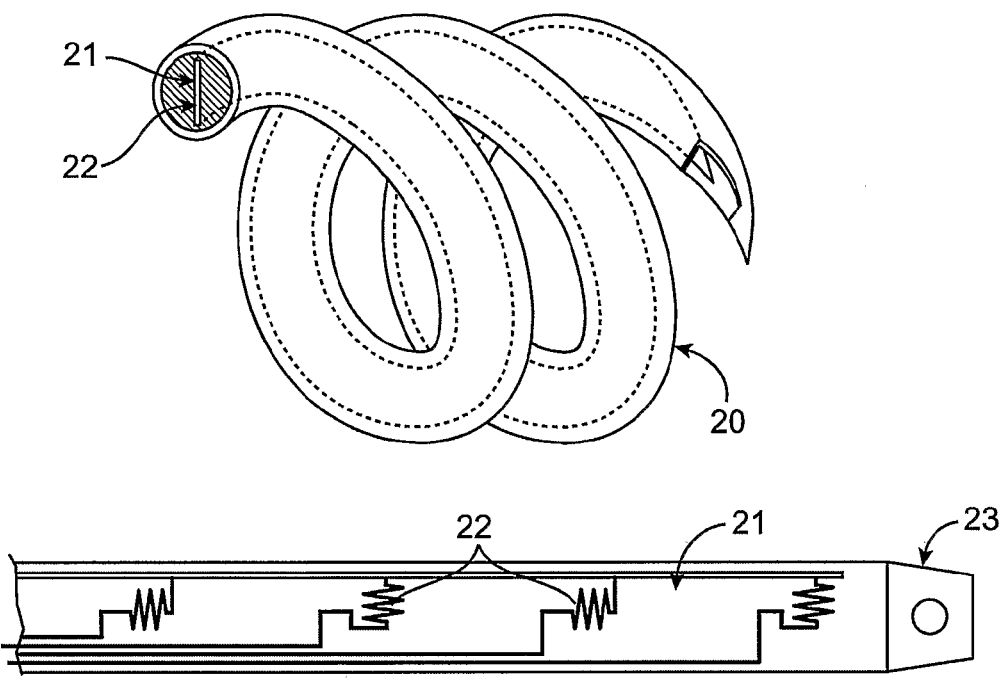
FIG. 13
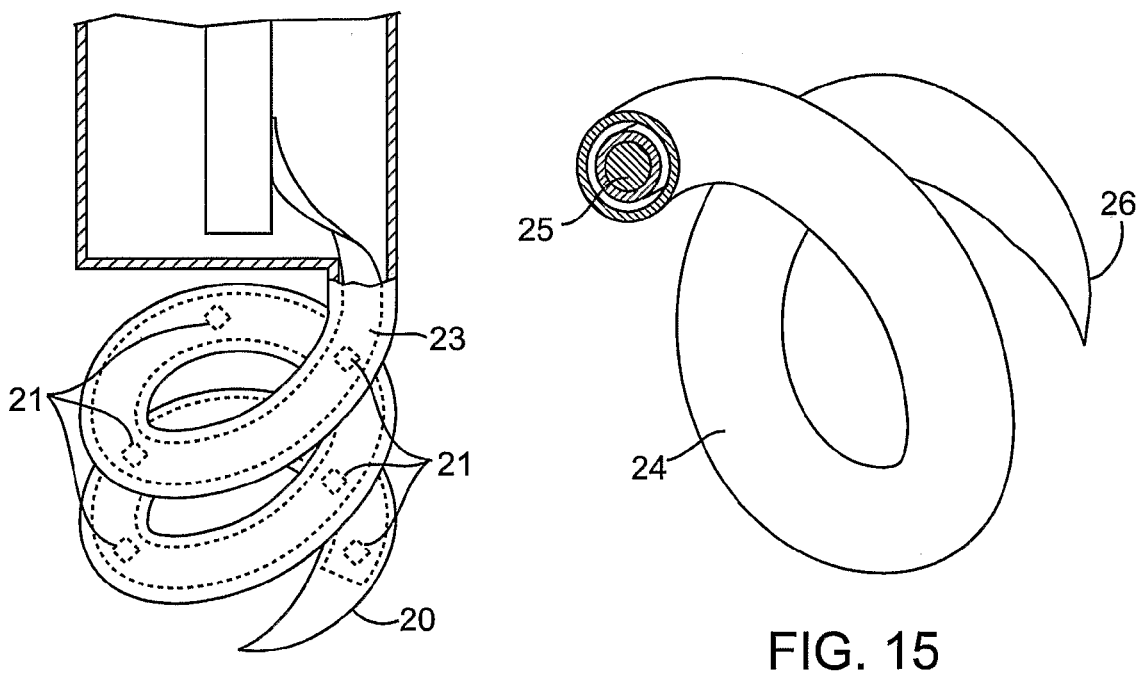
FIG. 14
FIG. 15

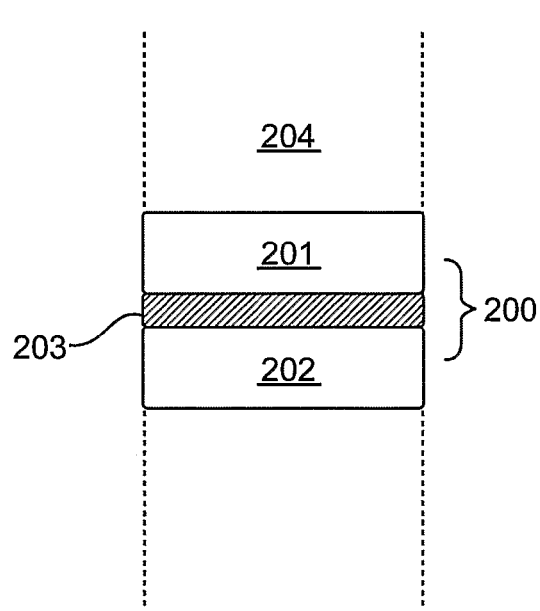 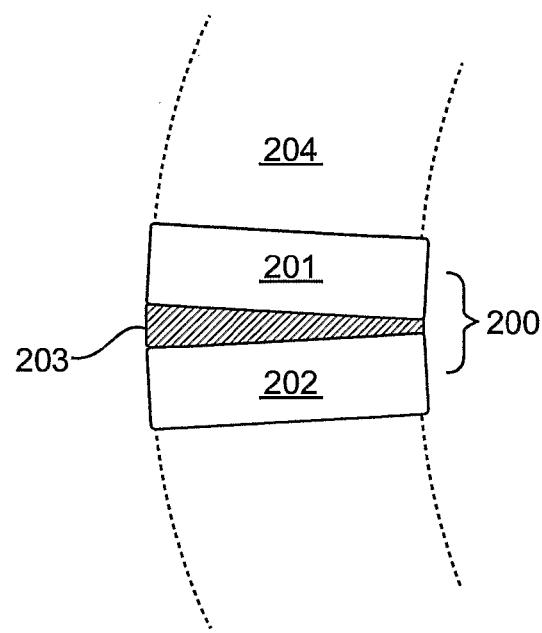
FIG. 25A  FIG. 25B
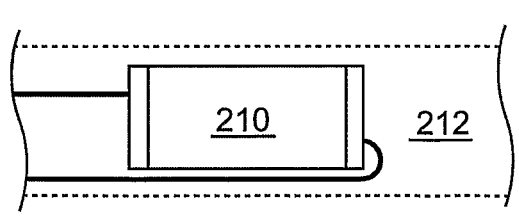 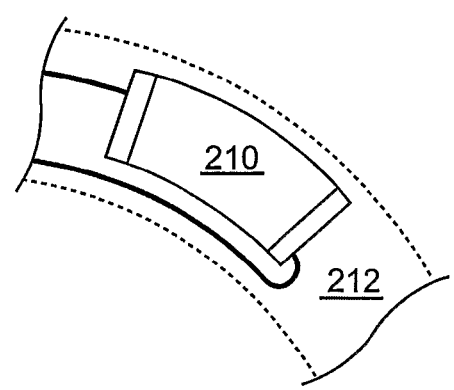
FIG. 26A  FIG. 26B

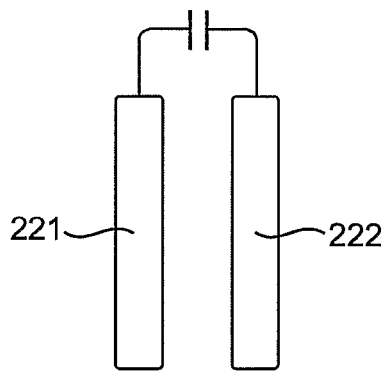
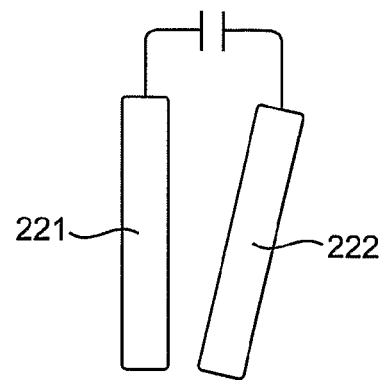
FIG. 27A  FIG. 27B
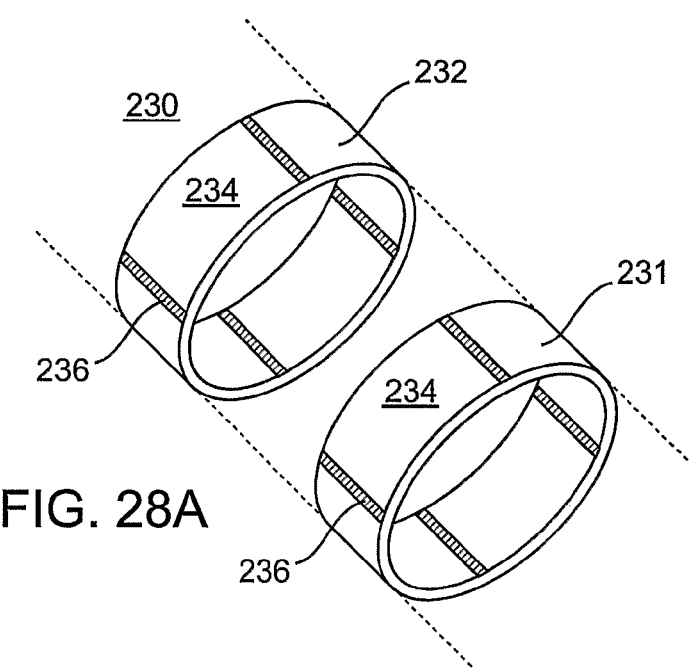
FIG. 28A
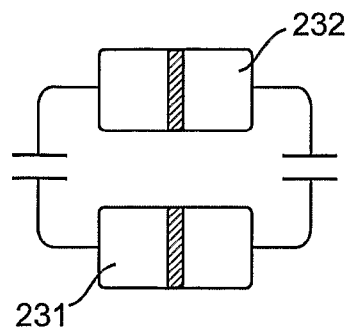
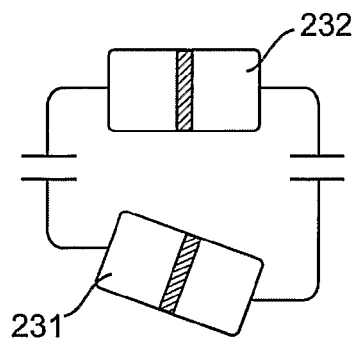
FIG. 28B  FIG. 28C

CARDIAC MOTION CHARACTERIZATION BY STRAIN MEASUREMENT

CROSS-REFERENCE TO RELATED APPLICATIONS

Pursuant to 35 U.S.C. §119 (e), this application claims priority to the filing date of: U.S. Provisional Patent Application Ser. No. 60/624,427 filed Nov. 1, 2004; U.S. Provisional Patent Application Ser. No. 60/638,247 filed Dec. 20, 2004; U.S. Provisional Patent Application Ser. No. 60/638,947 filed Dec. 22, 2004; and U.S. Provisional Patent Application Ser. No. 60/667,749 filed Mar. 31, 2005; the disclosures of which are herein incorporated by reference.

INTRODUCTION

Background of the Invention

In a diverse array of applications, the evaluation of tissue motion is desirable, e.g., for diagnostic or therapeutic purposes. An example of where evaluation of tissue motion is desirable is cardiac resynchronization therapy (CRT), where evaluation of cardiac tissue motion as observed by traditional ultrasound techniques is employed for diagnostic and therapeutic purposes.

CRT is an important new medical intervention for patients suffering from heart failure, e.g., congestive heart failure (CHF). When congestive heart failure occurs, symptoms develop due to the heart's inability to function sufficiently. Congestive heart failure is characterized by gradual decline in cardiac function punctuated by severe exacerbations leading eventually to death. It is estimated that over five million patients in the United States suffer from this malady.

The aim of resynchronization pacing is to induce the interventricular septum and the left ventricular free wall to contract at approximately the same time.

Resynchronization therapy seeks to provide a contraction time sequence that will most effectively produce maximal cardiac output with minimal total energy expenditure by the heart. The optimal timing is calculated by reference to hemodynamic parameters such as dP/dt, the first time-derivative of the pressure waveform in the left ventricle. The dP/dt parameter is a well-documented proxy for left ventricular contractility.

In current practice, external ultrasound measurements are used to calculate dP/dt. Such external ultrasound is used to observe wall motion directly. Most commonly, the ultrasound operator uses the ultrasound system in a tissue Doppler mode, a feature known as tissue Doppler imaging (TDI), to evaluate the time course of displacement of the septum relative to the left ventricle free wall. The current view of clinicians is that ultrasonographic evaluation using TDI or a similar approach may become an important part of qualifying patients for CRT therapy.

As currently delivered, CRT therapy is effective in about half to two-thirds of patients implanted with a resynchronization device. In approximately one-third of these patients, this therapy provides a two-class improvement in patient symptoms as measured by the New York Heart Association scale. In about one-third of these patients, a one-class improvement in cardiovascular symptoms is accomplished. In the remaining third of patients, there is no improvement or, in a small minority, a deterioration in cardiac performance. This group of patients is referred to as non-responders. It is possible that the one-class New York Heart Association responders are actually marginal or partial responders to the therapy, given the dramatic results seen in a minority.

The synchronization therapy, in order to be optimal, targets the cardiac wall segment point of maximal delay, and advances the timing to synchronize contraction with an earlier contracting region of the heart, typically the septum. However, the current placement technique for CRT devices is usually empiric. A physician will cannulate a vein that appears to be in the region described by the literature as most effective. The device is then positioned, stimulation is carried out, and the lack of extra-cardiac stimulation, such as diaphragmatic pacing, is confirmed. With the currently available techniques, rarely is there time or means for optimizing cardiac performance.

When attempted today, clinical CRT optimization must be preformed by laborious manual method of an ultrasonographer evaluating cardiac wall motion at different lead positions and different interventricular delay (IVD) settings. The IVD is the ability of pacemakers to be set up with different timing on the pacing pulse that goes to the right ventricle versus the left ventricle. In addition, all pacemakers have the ability to vary the atrio-ventricular delay, which is the delay between stimulation of the atria and the ventricle or ventricles themselves. These settings can be important in addition to the location of the left ventricular stimulating electrode itself in resynchronizing the patient.

Current use of Doppler to localize elements in the heart have been limited to wall position determination via external ultrasonography, typically for purposes of measuring valve function, cardiac output, or rarely, synchronization index.

There is currently no useful clinically available means of determining optimal CRT settings on a substantially automatic or a real-time, machine readable basis. It would be an important advancement in cardiology to have an implantable means of monitoring the mechanical performance of the heart in real time, an immediate application being in setting the functions of cardiac resynchronization therapy pacemakers, with further application to the pharmacologic management of heart failure patients, arrhythmia detection and ischemia detection, etc.

SUMMARY OF THE INVENTION

Methods for evaluating motion of a cardiac tissue location, e.g., heart wall, are provided. In the subject methods, timing of a signal obtain from a strain gauge stably associated with the tissue location of interest is employed to evaluate movement of the cardiac tissue location. Also provided are systems, devices and related compositions for practicing the subject methods. The subject methods and devices find use in a variety of different applications, including cardiac resynchronization therapy.

BRIEF DESCRIPTION OF THE FIGURES

FIG. 13 provides a screw end design for localized measuring cardiac timing;

FIG. 14 provides a screw end design as attached to a cap;

FIG. 15 provides a design for localized measuring cardiac timing in a minimalist design;

FIGS. 25A and B provide views of a marker band strain gauge embodiment of the invention;

FIGS. 26A and B provide views of a resonant piezoelectric strain gauge embodiment of the invention;

FIGS. 27A to 28C provide views of capacitance band strain gauge embodiments of the invention;

DESCRIPTION OF SPECIFIC REPRESENTATIVE EMBODIMENTS

Figure 1A:
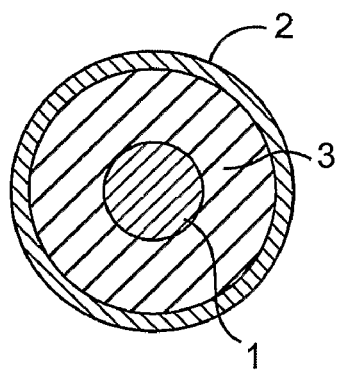
FIGS. 1A and 1B provide a view of an inventive embodiment using small dimension strain gauges.

Methods for evaluating motion of a cardiac tissue location, e.g., heart wall, are provided. In the subject methods, timing of a signal obtain from a strain gauge stably associated with the tissue location of interest is employed to evaluate movement of the cardiac tissue location. Also provided are systems, devices and related compositions for practicing the subject methods. The subject methods and devices find use in a variety of different applications, including cardiac resynchronization therapy.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the subject invention, a general review of the subject methods and systems as well as various aspects thereof is first provided. Next, a more detailed review of specific embodiments with reference to various figures is provided. Following this section, representative applications in which the subject invention finds use are described, as well as other aspects of the invention, such as computer related embodiments and kits that find use in practicing the invention.

Overview of Cardiac Motion Characterization by Strain Measurement

As summarized above, the subject invention provides methods for evaluating movement of a cardiac tissue location of interest by strain measurement. In the subject methods, data obtained by a strain sensing element stably associated with the cardiac tissue location of interest is employed. A feature of the present invention is that the data which is employed at least includes, and sometimes solely includes, the timing of a signal obtained from a strain gauge. Accordingly, an aspect of embodiments of the invention is to ignore the total deflection of the element, but instead to use the timing of the motion to evaluate, e.g., determine, when the tissue or organ moves. The advantage of a strain gauge over other motion sensors, such as an accelerometer or other transducer, is that the strain gauge is orders of magnitude less complicated, and thereby more robust and reliable. An embodiment of the present strain measurement innovation is configured to provide critical information on wall motion for cardiac resynchronization therapy, such as for the treatment of congestive heart failure. Aspects of the invention provide strain gauges positioned in or on the heart for determining cardiac wall contraction synchrony and/or disynchrony.

The inventive use of strain gauges to determine cardiac wall motion timing allows a minimally invasive, highly miniaturized means for the direct measurement in real-time of the wall motion occurring in the beating heart. The measurements provided by the present invention provided the amplitude and timing of the strain and/or shortening of the muscle fibers of the heart.

The inventive strain gauge sensors enjoy special qualities not available to other sensors. By example, these prior methods typically indicate general motion that is occurring in the heart, using, for example, accelerometers and Doppler effect transducers. Cardiac accelerometers will measure any movement as a person walks around a room, travels in a vibrating vehicle, or similar daily activities. Doppler approaches will measure relative motion between different points. However, the signal is relatively small and thus sophisticated data filtering is needed. The advantages of the present strain measurement invention allow it special qualities in cardiac sensing, which, in combination with simplicity and minute size requirements, in many cases proves synergistic with other sensors, as reviewed in greater detail below.

In contrast to many other cardiac sensors, the strain gauge approach of the present invention measures the timing of motion of the cardiac wall. This characteristic provides unique advantages in providing critical information to the clinician in providing and optimizing cardiac synchrony therapy. Important goals of research in this area have been to measure the relative movement of the right ventricular free wall, the left ventricular free wall, and the septum (between the two ventricles). These goals are met by the innovative use of the strain gauges in the means and methods of the present invention.

The present inventive use of strain gauges provides information based on timing and deflection of the sensors. The measurement is a simple signal, measuring whether or not strain is occurring; and therefore indicating whether or not the muscle is contracting. By way of example, when the inventive strain gauge is placed in a cardiac vein that runs along the endocardial aspect of wall of the left ventricle, data is provided to the clinician as to the timing of left ventricular wall movement. These data can be obtained using a single strain gauge or multiple strain gauges, depending on the specific application. In contrast to currently employed methods using pressures and/or Tissue Doppler imaging, the use of the present strain gauge invention allows the clinician to directly measure from just this sort of on/off motion sensor, whether or not the two particular cardiac chambers are contracting at the same time. More important is the determination of whether the septal and free wall contractive element of the left ventricle are also contracting at the most optimal time for continuing to cardiac output. These particular representative applications are reviewed below in greater detail.

As such, the inventive cardiac timing device is a medical tool using strain gauges as timing devices for measurement and control of local organ motion, such as various cardiac features. The new and unobvious use for strain gauges is to use the sensor primarily as an event timing measurement device. In this new use, the total magnitude of the change in strain is of secondary concern. This strain signal would be filtered to indicate motion of tissue through appropriate filters, but then would provide positive signal as to when the tissue started to move. In addition, through calibration of the device, the direction of motion could also be determined.

As is known in the art, a stain gauge is traditionally used in an application where the deflection (strain) is calibrated for certain force (stress). Strain gauges are used most often in tensile testing machines. In the majority of these applications the strain gauge is only used to determine the force applied to a test specimen when it experiences a force at a known rate.

The new and novel use of a strain gauge described herein is to ignore the total stress measurement that this sensor would normally provide. Instead only the timing of motion is the required output of the device. The force (stress) can also be measured but it is of only second order concern in this application. The advantage of a strain gauge over other motion sensors, such as an accelerometer or other transducer, is that it is orders of magnitude less complicated, and thereby more robust and reliable. Additional advantages over such devices as accelerometry are the reduction of confounding signals. An accelerometer will detect motion of the body that the device is used in, walking for example. An accelerometer will also detect motion from adjacent organs, including motion from respiration. All these extraneous signals will need to be filtered out to avoid interference with the data that the accelerometer is trying to measure. With the strain gauge, motion timing from a specific local tissue area is much easier to measure.

Aspects of the strain gauges employed in the subject methods are the presence of one or more transducers that generate a signal, e.g., electrical, optical etc., in response to an applied stimulus, e.g., deflection, bending, stretching, etc. In representative embodiments, the strain gauge is incorporated into a medical device at or under surface of the device. The strain gauge provides a signal when the tissue location of interest moves, since the strain gauge is stably associated with the tissue location of interest.

As summarized above, the subject invention provides methods of evaluating movement of a tissue location. "Evaluating" is used herein to refer to any type of detecting, assessing or analyzing, and may be qualitative or quantitative. In representative embodiments, movement is determined relative to another tissue location, such that the methods are employed to determine movement of two or more tissue locations relative to each other.

The tissue location(s) is generally a defined location or portion of a body, i.e., subject, where in representative embodiments it is a defined location or portion (i.e., domain or region) of a body structure, such as an organ, where in representative embodiments the body structure is an internal body structure, such as an internal organ, e.g., heart, kidney, stomach, lung, etc. In representative embodiments, the tissue location is a cardiac location. As such and for ease of further description, the various aspects of the invention are now reviewed in terms of evaluating motion of a cardiac location. The cardiac location may be either endocardial or epicardial, as desired, and may be an atrial or ventricular location. Where the tissue location is a cardiac location, in representative embodiments, the cardiac location is a heart wall location, e.g., a chamber wall, such as a ventricular wall, a septal wall, etc. Although the invention is now further described in terms of cardiac motion evaluation embodiments, the invention is not so limited, the invention being readily adaptable to evaluation of movement of a wide variety of different tissue locations.

In practicing embodiments of the invention, following implantation of any required elements in a subject (e.g., using known surgical techniques), the a signal (representing data) from a strain gauge sensing element that is stably associated with the tissue location of interest is then detected to evaluate movement of the tissue location. As reviewed above, the timing of the signal obtained from the sensing element is employed, e.g., in characterizing movement of the tissue location of interest.

By "stably associated with" is meant that the sensing element is substantially if not completely fixed relative to the tissue location of interest such that when the tissue location of interest moves, the sensing element also moves. As the employed strain gauge sensing element is stably associated with the tissue location, its movement is the same as (or at least a proxy for such that it serves as a suitable indicator on the movement of the tissue location to which it is stably associated. The sensing element may be stably associated with the tissue location using any convenient approach, such as by attaching the sensing element to the tissue location by using an attachment element, such as a hook, etc., by having the sensing element on a structure that compresses the sensing element against the tissue location such that the two are stably associated, etc.

In a given embodiment, the sensing element can provide output in an interval fashion or continuous fashion for a given duration of time, as desired.

In certain embodiments, a single sensing element, e.g., strain gauge, is employed. In such methods, evaluation may include monitoring movement of the tissue location over a given period of time. In certain embodiments, two or more distinct sensing elements are employed to evaluate movement of two or more distinct tissue locations. The number of different sensing elements that are employed in a given embodiment may vary greatly, where in certain embodiments the number employed is 2 or more, such as 3 or more, 4 or more, 5 or more, 8 or more, 10 or more, etc. In such multi-sensor embodiments, the methods may include evaluating movement of the two or more distinct locations relative to each other.

In certain embodiments, the subject methods include providing a system that includes a strain gauge sensing element that is stably associated with the tissue location of interest. This providing step may include implanting one or more new elements into a body. This step, if employed, may be carried out using any convenient protocol, where a variety of protocols are well known to those of skill in the art.

The subject methods may be used in a variety of different kinds of animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In many embodiments, the subjects or patients will be humans.

The tissue movement evaluation data obtained using the subject methods may be employed in a variety of different applications, including but not limited to monitoring applications, treatment applications, etc. Representative applications in which the data obtained from the subject methods finds use are further reviewed in greater detail below.

General Design Considerations

The following section reviews a number of different features of different aspects of representative embodiments of the invention.

Materials

A wide variety of materials are appropriately employed in the fabrication of the strain gauges of the present innovative cardiac timing device. These materials are well know to the artisan, and can be varied with the particular intended use and placement of the device.

In representative embodiments, the strain gauges of the present invention are fabricated from a metal or metal alloy. In certain embodiments, the alloy is selected with high resistance characteristic. High resistance alloys appropriate for use in the strain gauges of the inventive cardiac timing device have at least one high resistance material component. By high resistance is meant a resistance of at least about 1000 ohms, such as at least about 2000 ohms or higher, e.g., 5000 ohms or higher. Examples of such materials are Constantan (copper-nickel alloy), Nichrome V (nickel-chrome alloy), platinum alloys (e.g., alloys with chromium, nickel, tungsten, etc.), Isoelastic (nickel-iron alloy), or Karma-type alloy wires (nickel-chrome alloy), foils, or semiconductor materials, e.g., poly-crystalline silicon or similar materials. In representative embodiments, the strain gauges are fabricated from copper-nickel alloys and nickel-chromium alloys, and can be employed in the present invention.

Platinum alloys are the materials employed in representative embodiments for construction of the strain gauges of the present cardiac timing device. Platinum alloys are particularly suitable for use in the present invention because they can often be used in direct contact with the body with limited ill effects, such as corrosion or toxic seepage into the body. Thus, platinum alloy materials of the present invention can effectively allow some contact, and in some cases, direct contact of the sensors with the body and body fluids.

Sensor Not Requiring Hermeticity Seal

The embodiments of the present invention that allow for direct contact of the sensor with body fluids provides a number of advantages. Direct contact with the cardiac features to be assessed provides an increase in sensitivity. Obviation of the requirement of a hermeticity layer allows an even greater miniaturization of the sensing device, providing the opportunity to position sensors in previously unavailable areas, and to provide many multiple sensors in a small space. This simpler design also provides a much simplified fabrication process.

The ability of the strain gauges of certain embodiments of the present cardiac timing device to function successfully without the requirement of hermetic sealing provides an important functional design advantage. An advantage of the direct body fluid contact inventive configuration is the concomitant increase in sensitivity of strain measurements which occurs when the sensors are not isolated from the cardiac features to be measured. The capacity to function without a hermetical seal is particularly advantageous in the context of the timing of the present invention as the direct ascertainment of the time of strain allows the most accurate assessment of the timed event.

The capability of the present strain gauges to tolerate direct contact with body fluids allows an even greater miniaturization of the present device, a key advantage of the present invention over other sensing devices. Thus, the strain gauges of the present invention can go beyond their uniquely small dimension to an even smaller profile using platinum alloys or other design approaches which circumvent the requirement of a hermetic seal to survive in the body environment.

The elegantly simple design approach of the innovative cardiac timing device eliminates numerous manufacturing steps which would otherwise be required for the assembly of the device. Fabrication processes are much simplified, limiting quality control problems, speeding production, and decreasing fabrication expenses.

Fatigue Considerations

The fatigue life of the material used in the strain gauge components of the present cardiac timing device also needs to be considered in selection of an optimal material for a particular embodiment of the invention. The fatigue life aspect of material selection is more critical when the cardiac timing device is planned for use in implantable applications, but less so for temporary use applications.

In long-term implantable applications of the inventive cardiac timing device, a material for the strain gauge component is typically one that has a fairly long fatigue life. Such materials have a relatively high yield point, and can be selected from a range of alloys. While modified for other design considerations, longevity of the device is preferably selected from strain gauge materials that have the highest yield point practicable. Platinum alloys, particularly those hardened with tungsten Pt-8W, Pt-10Ir or Pt-20Ir typically provide a high fatigue life to the strain gauge component.

Sensor Substrate

The strain gauge transducers may be bonded on any of a number of flexible or compliant substrates in the strain gauge sensor element. In certain embodiments, the substrate is a compliant substrate. Examples of suitable materials for the substrate are polyimide, polyetherimide, polyetherketone (PEEK), polyphenylene sulfide, polyethylene terephthalate, fluoroethylene-propylene (FEP), among others. Certain of these substrate materials are known to biocompatible, and thus and can be directly exposed to blood or tissue. PEEK is one such substrate.

The key to material selection for the strain gauge substrate is assuring that the thickness of the material and its bending stiffness is matched with the flexibility of the medical device that it is incorporated into. The substrate material also can be so designed to inhibit the motion of the strain gauge in unintended directions. Using this approach, a flexible construction is provided which allows the strain gauge to experience forces to which it is subject in its implanted position, such as within a cardiac lead.

Sensors Not Requiring Substrate

In a particularly minimalist embodiment of the inventive cardiac timing device, the strain gauge components are fabricated to be incorporated into the medical device without a flexible substrate. The strain gauge metallic member is molded into lead body itself. This inventive design approach limits or even eliminates the flexible backing component of the embodiments described above.

Optical Strain Gauges

One embodiment of the present invention provides an inventive cardiac motion detection system that includes optical strain gauges. By detecting changes in optical signals instead of electrical signals, and by combining fiberoptics and micro-machining technologies, the inventive cardiac motion detection system presents a powerful new tool in a physician's armamentarium. This new tool performs accurate, real-time monitoring of cardiac motions, and thus facilitates more precise CRT treatment. In these embodiments, an optically conductive element is employed to convey timing signals from the transducers of the sensing elements, as opposed an electrically conductive element, as reviewed in connection with other embodiments elsewhere in this application.

The use of optical sensing immunizes the present inventive cardiac motion detection system of these embodiments from external electrical or magnetic interferences. One embodiment of the present invention uses optical sensing and detection techniques to identify cardiac motion. Optical signals, when transmitted in a confined medium such as optical fiber, are known to be immune from external electrical or magnetic interferences. This feature allows the present detection system to detect much weaker signals which cannot be distinguished by prior motion detection systems. As a result, these embodiments have superb sensitivity and dynamic range.

In addition, the present system allows simultaneous operation of a large number of strain gauges. The present system enjoys this unique advantage because multiple wavelengths can be transmitted through a single optical fiber without interfering with each other. In one embodiment of the present invention, a cardiac motion detection system multiplexes many wavelengths into one optical fiber and operates each fiberoptic strain gauge at a different wavelength. In this way, the present inventive system can simultaneously detect the cardiac motion at a number of locations without occupying additional space within a catheter.

By using fiberoptic strain gauges, the present inventive cardiac motion detection system allows unprecedented reduction of the size of a motion sensor. The inventive combination of fiber optics and micro-machined structures provides a strain gauge with a size comparable to the outer diameter of a regular optical fiber, which is typically 125 µm. Such fiberoptic strain gauges enable a physician to place them in optimal positions within the heart and to limit implantation procedure time. Moreover, the implantation procedure is made much less invasive to the patient. As a result, the risk associated with the implantation procedure and the subsequent monitoring of cardiac motions is considerably lower.

Multiple Stain Gauges

In representative embodiments, a given strain gauge sensing element includes two or more individual transducer elements. As such, in a range of embodiments of the present cardiac timing device, multiple strain gauge transducer elements can be incorporated within a specific location, e.g., on the same and/or opposing surfaces of a substrate, in a given sensing element. This configuration of the inventive cardiac timing device allows the subtraction of motion timing components in directions which are not of interest.

In certain embodiments of the inventive cardiac timing device, axial strain is a force component that is a potential source of interfering background signal. A second strain gauge transducer forming a half bridge and located on the opposite side of the member, e.g., compliant substrate, can allow for the elimination of this motion component. More complex configurations with additional transducers are also employed in certain embodiments. Representative configurations of interest include, but are not limited to: two pairs of transducers, where each member of the pair is on an opposite surface of the compliant member, where the pairs can be parallel to each other, at right angles to each other, etc.

In some inventive cardiac timing device designs, timing can be determined from axial strain as well as bending strain. Proper selection and orientation of two strain gauges forming a half bridge limits or eliminates the bending strain component of the signal. Additional orientations of the strain gauges can be planar. Alternatively, the gauges can be inserted into the cardiac timing device in a curved shape. Other configurations of individual or groups of strain gauges provide the best sensing for timing of the motion of the heart which is of greatest interest in a particular application. Referencing multiple different sensors with different orientation and/or designs allows a range of information to be available to the clinician. A full bridge strain gauge configuration can be employed that, when wrapped around the outside body of the lead device, provides orientation data independent of the measure of deflection amplitude.

Multiple strain gauges in the proper orientation allows for the elimination of potential confounding changes in the resistance of the strain gauge due to temperature. Resistance changes can occur due to fluctuations in body temperature, such as when a patient is exposed to cold causing hypothermia or exposure to heat or fever from infection causing hyperthermia.

Post Processing Steps

The analysis of the strain gauge data may benefit from post processing to determine the timing of the motion. For people skilled in the art of signal processing it is well known how to process the signal to provide the most accurate data for clinical interpretation.

In certain embodiments of the device, signal processing is performed. For example, a strain signal from the device drives an auditory device that relays timing signals to the clinician as a series of tones. The clinician, prompted by these tones, then measures and adjusts the timing of the cardiac muscle by listening to different frequency tones that converged to one frequency as the timing of the heart was improved.

A visual signal can also be derived from the strain timing information. A series of lights is produced from the strain gauge signal that would change from red to green as the change in timing of the cardiac muscle was improved.

Electrical Design Considerations

The electrical connections which are employed in the inventive cardiac timing device incorporating the strain gauge are, in some cases, provided with appropriate diodes and electrical components. These components are arranged in a manner which limits or eliminates any conduction of stray electrical signals which could otherwise prove disadvantageous. This design consideration is particularly relevant in the combined effecting-sensing embodiments of the present cardiac timing device. A typical example would be a cardiac sensor/pacing system. Additionally, if a patient is subjected to cardiac defibrillation therapy, the inventive cardiac timing device is so designed to avoid compromise of function.

Fabrication

The strain gauges selected or developed for inventive cardiac timing may be constructed using any convenient fabrication method. In representative embodiments, a vapor deposition process is an appropriate fabrication method for strain gauges in the inventive cardiac timing device. In this fabrication, a photo resistive mask is employed, similar to a MEMS processing approach.

An additional fabrication method for strain gauges in the inventive cardiac timing device employs photo etching of the strain gauges. Alternatively, a laser cutting approach can be utilized. For the latter, the strain gauges are cut from thin sheets of the alloy of choice. A pattern for the strain gauge is drawn with an electronic CAD program. The data file for that pattern is exported to a laser cutting machine where the CAD file is translated to a machine readable file. That file is used to drive the cutting of the desired shape. The shape can also be laser cut or photo etched into tubing of the appropriate alloy selection.

Positioning of Strain Gauges in Device, and Device in Body

The location of the strain gauge in the body of the cardiac timing device directly impacts the significance of signal which it transmits. During insertion of the cardiac timing device, it is possible to fine tune the location of the sensor elements. The optimal positioning of strain gauge sensors within the device is also pivotal in providing the best possible cardiac timing information from the device.

Positioning of the strain gauges both within the device and within the body provides for optimum motion signal and motion timing for detection of heart wall motion. In preferred embodiments, the positioning of the strain gauge within the device or positioning means will be off the neutral axis. The positioning can also be provided at the outside edge around the diameter of the device. Optimal location of the strain gauge components within the cardiac timing device are determined as a function of the bending stiffness of the material of which the lead or other device body components, such as the catheter device are composed.

If the material of the cardiac timing device body components are selected from within a relatively soft range, there is the opportunity for the strain gauge component to be implanted more deeply into the device without disadvantageously compromising sensing capabilities. An example of such materials are silicone and its derivatives. Conversely, if the material of the cardiac timing device body is more rigid, the strain gauge component will typically implanted less deep into the device. A typical example of such harder materials is polyurethane.

Where multiple strain gauges are used, it is advantageous to separate them from the mechanical strain from adjacent sections of the body of the device. This can be accomplished by providing softer material in areas of the body of the device between locations where the strain gauge components are embedded. This approach serves to mechanically isolate the strain gauge components from each other. This approach can ameliorate or obviate a potential risk of strain from one section of the device being transmitted through the device to another section. If such transmitted strain is recorded by the more distant strain gauges, these background strains can obscure or compromise the readings of ambient physical strains of the areas where the strain sensors have been positioned.

Temporary Cardiac Devices

For temporary cardiac sensing applications of the strain gauge, the strain gauge attachment and communication means for the inventive cardiac timing device can be accomplished using a wide range of methods. Because the placement is temporary, miniaturization and long term survivability do not represent the serious challenges to design which they do for the development of permanent devices.

One highly simplified fabrication approach well suited to construction of temporary cardiac timing devices is to simply run small gauge conductive wires down the center of a catheter. Once in position, these wires are soldered or welded to the desired strain gauges.

In the case of temporary cardiac timing device, a multiplicity of wires can be provided down the catheter device as dimension is a much less critical component than in the case of permanent devices. This multiwire configuration allows for the gleaning of data from a number of strain gauges at different locations or at the same location, each having a unique wire connection. Such multiple wire configurations are more practical in temporary devices, as the denier size of the device can be larger.

A more compact interaction of the above multiplicity of wire design for the inventive cardiac timing device is accomplished by running conductors down to each strain gauge in a cable configuration. The cable is provided in a wound configuration, where each conductor wire is individually insulated. At the location where the wires are to be attached to the strain gauge, these wires are stripped. At these stripped points, the strain gauges are either welded or soldered to provide permanent contact with the appropriate wires.

Permanent Cardiac Devices

A particularly advantageous design for semi-permanent and permanent embodiments of the inventive cardiac timing device is the approach of using one common connection and a single wire running to each individual connection. This is a bus type configuration. In this design of the innovative cardiac timing device, the opportunity is provided for a long string of strain gauges implanted along the length of the device.

In contrast to the temporary configurations described above, however, a bus configuration provides a single wire or conductor which serves all of the strain gauge components for one side of the electrical connection. This bus configuration allows an extremely small denier size, which can be pivotal in providing the cardiac timing device in an acceptable form for more permanent uses. This bus configuration also plays on the strength of the very small dimensions available for the strain gauge components, as compared to other motion sensors such as accelerometers.

In the permanent implant embodiment of the inventive cardiac timing device, conductors are selected to each strain gauge which have a relatively high fatigue life. The capacity to survive 400 million cycles prior to failure is the typical requirement for long term implant cardiac devices. For the construction of devices meeting these requirements, several design approaches are particularly suitable.

Additionally, strain gauges for permanent implant cardiac timing devices are advantageously connected to a central set of wound conductor cables. These wound conductor cables would typically be fabricated of stainless steel with a silver core. This construct is then coated with an electrically isolating coating of polyimide, and wound together to form a cable. This cable configuration provides the capacity to run a multiplicity of conductors down to multiple strain gauge locations.

Methods Overview

A simple application of the inventive strain sensor is to place catheters, with strain sensors attached, on both the left ventricular free wall, the right ventricular free wall, and potentially directly on the septum. This placement of the inventive device produces a very simple signal indicating when each of these cardiac features is contracting, the amplitude and time course of the contraction, and in some configurations their direction of movement. In order to obtain data on direction of movement, the strain gauges are oriented appropriately with a steerable implantation device. When combined with pressure readings from other sensors, the present invention allows the comparison of contraction timing and the pressure changes in the ventricles.

A prior art data point for CRT therapy has been pressure-pressure loops. In the general case it is thought that in the healthy heart, both ventricles contract at the same time. In that case, peak pressure would be achieved in both ventricles simultaneously. This test has been employed as a measure of potential synchrony. In dyssynchronous hearts, the pressure peak typically occurs at different times, suggesting that the muscle is contracting at different times. This difference in contraction can be directly measured with the present inventive strain gauges. Comparison to RV and/or LV pressures will add additional global data over strain gauges alone.

In an additional embodiment of the present invention, the strain gauge is attached to the ventricular septum, the wall between the two ventricles. Cardiologists often characterize the septum moving much like a sail. If pressure peaks are occurring at different times in the ventricles, the septum bows into whichever ventricle is at the lowest pressure. If the left ventricle compresses later than the right ventricle, the right ventricle will be in a relaxation phase during the LV contraction. In this case, the septum is likely to deflect into the right ventricle. By measuring the direction and/or timing of the deflection of the septum related to pressure changes, the clinician can determine, without even measuring a left ventricular pressure, when the pressure peak is occurring in the left ventricle.

An additional use of the present strain gauges is to determine apex movement. In this case, a strain gauge is placed near or at the tip of a device at the apex of one of the ventricles, left or right, preferably the right ventricle. These devices provide a measure of when the apex is moving. A number of parameters can be measured by this device placement. By example, the timing of apical contraction can be determined, as well as changes in the amplitude of the contraction. This sensing capacity can be provided by one of the following features.

In general, two types of data are collected in representative embodiments of the invention. In the simplest case, the timing of the motion is collected by simply analyzing when the contractions occur. In this case the amount of strain is not important and the strain measuring elements do not need calibration. This case could also be used as a method to measure the difference between contractions that occur before, during and after CRT optimization. The actual amplitude of the contractions is not important, only the difference between the contractions before and after an optimization procedure.

In a more complex case, the device assembly with the strain gauges is calibrated. With this calibrated device, the amount of strain, or deflection of the device, and therefore the tissue in question is measured accurately. This approach is employed for more accurately measuring the real motion or strain that is occurring. For example, the motion of the apex alone shows, in certain embodiments, whether a heart is beating synchronously or not. If the apex moves from side to side due to dyssynchronous contraction of the ventricles (interventricular dyssynchrony) or within the left ventricle (intraventricular dyssynchrony), a reduction in the side to side and a shift to more apical to basal motion of the apex, or other changes in motion, is employed as an indication of improving synchrony. A combination of these measures also proves clinically useful.

An additional application of the inventive system is to place catheters, with strain sensors attached, on the left ventricular free wall, the right ventricular free wall, and potentially directly on the septum. Such a configuration produces direct, motion-derived signals indicating when each of these cardiac features is contracting, and the respective amplitude and time course of the contractions. In other configurations, a physician measures their direction of movement using the present detection system. In order to obtain data on direction of movement, the strain gauges are ideally oriented appropriately with a steerable implantation device. When combined with additional pressure readings, one embodiment of the present invention allows the comparison of contraction timing and the pressure changes in the ventricles.

Additional Features Found in Representative Systems

Embodiments of the subjects systems incorporate other physiologic sensors in order to improve the clinical utility of wall-motion data provided by the present invention. For example, an integrated pressure sensor could provide a self-optimizing cardiac resynchronization pacing system with an important verification means, since wall motion optimization in the face of declining systemic pressure would be an indication of improper pacing, component failure or other underlying physiologically deleterious condition (e.g., hemorrhagic shock). One or more pressure sensors could also provide important information used in the diagnosis of malignant arrhythmias requiring electrical intervention (e.g., ventricular fibrillation).

Incorporation of other sensors is also envisioned. For example, the prior work by some of the present inventors describes the use of dimension sensors for resynchronization. This system is described in part in currently pending patent applications U.S. patent application Ser. No. 10/764,429 entitled "Method and Apparatus for Enhancing Cardiac Pacing", U.S. patent application Ser. No. 10/764,127 entitled "Methods and Systems for Measuring Cardiac Parameters", and U.S. patent application Ser. No. 10/764,125 entitled "Method and System for Remote Hemodynamic Monitoring", all filed Jan. 23, 2004, U.S. patent application Ser. No. 10/734,490 entitled "Method and System for Monitoring and Treating Hemodynamic Parameters" filed Dec. 11, 2003, U.S. Provisional Patent Application 60/638,692 entitled "High Fatigue Life Semiconductor Electrodes" filed Dec. 22, 2004, and U.S. Provisional Patent Application 60/638,928 entitled "Methods and Systems for Programming and Controlling a Cardiac Pacing Device" filed Dec. 23, 2004. These applications are herein incorporated into the present application by reference in their entirety.

Some of the present inventors have developed Doppler, pressure sensors, additional wall motion, and other cardiac parameter sensing devices. Some of these are embodied in currently filed provisional applications; "One Wire Medical Monitoring and Treating Devices", U.S. Provisional Patent Application No. 60/607,280 filed Sep. 2, 2004, "Stable Micromachined Sensors" U.S. Provisional Patent Application 60/615,117 filed Sep. 30, 2004, "Amplified Complaint Force Pressure Sensors" U.S. Provisional Patent Application No. 60/616,706 filed Oct. 6, 2004, "Implantable Doppler Tomography System" U.S. Provisional Patent Application No. 60/617,618 filed Oct. 8, 2004, and PCT Patent Application PCT/US2004/041430 entitled "Implantable Pressure Sensors" filed Dec. 10, 2004, "Shaped Computer Chips with Electrodes for Medical Devices" U.S. Provisional Patent Application 60/655,609 filed Feb. 22, 2005. These applications are incorporated in their entirety by reference herein.

In the implantable embodiments of this invention, as desired wall motion, pressure and other physiologic data can be recorded by an implantable computer. Such data can be periodically uploaded to computer systems and computer networks, including the Internet, for automated or manual analysis.

Uplink and downlink telemetry capabilities may be provided in a given implantable system to enable communication with either a remotely located external medical device or a more proximal medical device on the patient's body or another multi-chamber monitor/therapy delivery system in the patient's body. The stored physiologic data of the types described above as well as real-time generated physiologic data and non-physiologic data can be transmitted by uplink RF telemetry from the system to the external programmer or other remote medical device in response to a downlink telemetry transmitted interrogation command. The real-time physiologic data typically includes real time sampled signal levels, e.g., intracardiac electrocardiogram amplitude values, and sensor output signals including dimension signals developed in accordance with the invention. The non-physiologic patient data includes currently programmed device operating modes and parameter values, battery condition, device ID, patient ID, implantation dates, device programming history, real time event markers, and the like. In the context of implantable pacemakers and ICDs, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/therapy delivery system thus develops a variety of such real-time or stored, physiologic or non-physiologic, data, and such developed data is collectively referred to herein as "patient data".

Specific Representative Embodiments and Systems

In further describing aspects of the subject invention, various representative systems and methods for their use are reviewed in terms of figures.

Guide Wire Applications

A key advantage of embodiments of the inventive cardiac timing devices employed in the subject methods is the unusually small dimensions available for the strain gauge sensor, even as compared to other micro-miniature cardiac sensors. Smaller devices which will inventively incorporate strain gauges are typically termed guide wire size applications. For guide wire size applications of the inventive cardiac timing device, devices are provided with a design to accommodate strain gauges that are on the order of 0.014 inches in diameter. Strain gauges are commercially available which are of a dimension sufficiently small to fit within currently available guide wires.

Figure 1B:
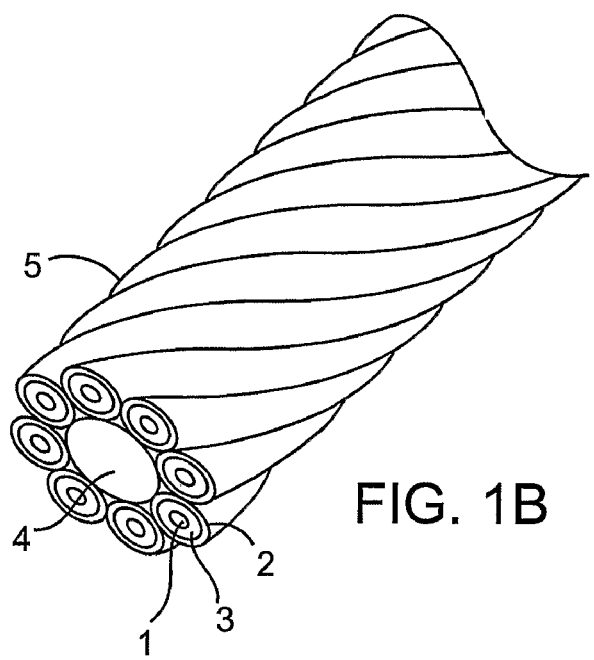
Figure 2:
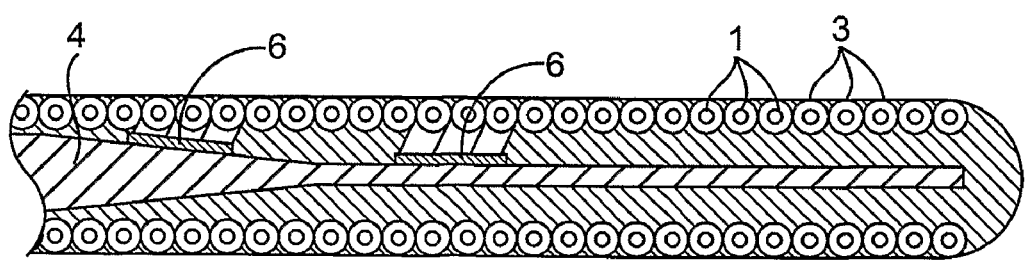
FIG. 2 provides longitudinal cross section of the spiral inventive configuration shown in FIG. 1B.

As shown in FIGS. 1 to 4, in a representative embodiment using small dimension strain gauges, a series of strain gauges are electrically connected along the length of a cardiac guide wire. As shown in FIGS. 1 and 2, these strain gauges are connected electrically with spiral wrapped coil. In this case, each conductor could be, for example, as shown in the cross-sectional view of FIG. 1A, where a silver core 1 is enclosed within a stainless steel wire 3. This composite wire is then coated with insulation layer 2, which can be composed of, for example, FEP or polyimide. A series of such wires are shown in the three-dimensional view of FIG. 1B which are spirally wrapped about a Stainless Steel (304V SS) or Ni—Ti super-elastic core 4. Various processes for spirally wrapping multi-fiber conductors are well known in the industry, where any convenient process may be employed.

A longitudinal cross section of the spiral configuration of the device shown in FIG. 11A is provided in FIG. 2. Drawn filled conductor material makes up the high tensile strength stainless steel jacket represented by stainless steel wire 3 surrounding a very conductive silver core 1 at the center of the wire. Typically, the silver core of the wire 5 is 28% of the total diameter. Each conductor is then insulated with an insulation layer 2, can be manufactured of FEP, polyimide, PTFE or other similar bio-compatible insulating materials which has a long survival life in a saline environment. The blunt tip represents the distal end of the guide wire 4 as shown in FIG. 2.

In this configuration, the conductor wires 5 are wound all the way to the tip of the guide wire core 4. In this position, the conductor is split out, stripped of its insulation, and then attached either by welding or soldering to strain gauges 6 located anywhere from half a centimeter from tip to 20 centimeters from distal tip of the device. A multiplicity of strain gauges 6 may be placed along the length of the device. Strain gauges 6 can be attached directly to the guide wire core 4 with adhesive. Alternatively, strain gauges 6 may be restrained in a specific orientation when the guidewire was over-molded and encapsulated with plastic material as part of the manufacturing process.

The guide wire 4 distal tip may have strain gauges 6 located 0.5 cm to 4.0 cm from the distal tip. Additional strain gauges 6 are located anywhere from 4.0 cm to 20.0 cm from the distal tip. Additional strain gauges could optionally be located in additional locations, the only constraint being the number of conductors that are available to connect with each individual strain gauge.

Figure 3:
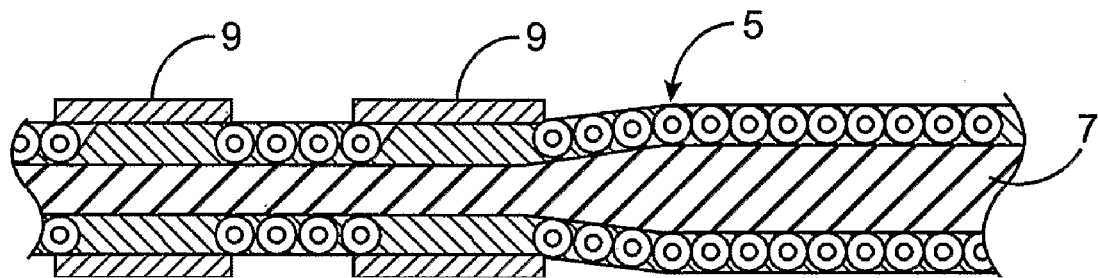
FIG. 3 provides additional views of the inventive configuration shown in FIG. 1.

FIG. 3 illustrates the proximal electrical connections for the strain gauges 6 in representative embodiments of the invention, where an easy to use electrical connection to whatever device that records and analyzes the signal coming from the strain gauges 6 is provided. In the embodiment depicted in FIG. 3, central core 7 of the guide wire is 12-13 thousandths in diameter. Central core 7 is covered by a multi-fiber conductor 5 that is wrapped around the guide wire 4. The conductors are tripped and either welded or soldered to conducting bands 9. There is a multiplicity of conducting bands 9 corresponding to each strain gauge 6.

Figure 4:
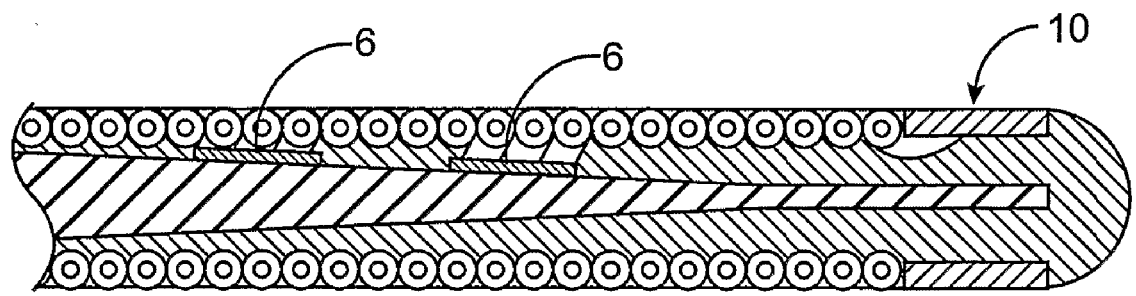
FIG. 4 provides additional views of the inventive configuration shown in FIG. 1 with the distal end construction of the guide wire.

As shown in FIG. 4, the distal end construction of guide wire 4 can incorporate a pacing ring 10 at the distal tip or some distance back from the distal tip. The multiplicity of conductors that go down the outside of the guide wire 4 can further provide connection with a pacing ring electrode 10 at the distal tip of the device. The electrode 10 has the capacity to sense electrical signals and pace the tissue. The electrode 10 can be one or more pacing rings. These rings are typically composed of platinum-10% iridium, with and iridium oxide coating. An alternate embodiment would use Pt-10% Ir wire wrapped around the SS core wire at the electrode. This wire could be coated with iridium oxide. This would produce a more flexible tip for the device and a longer possible electrode area.

The inventive cardiac timing device described above has the capacity to provide motion timing and electrical pacing and sensing on device enjoying a uniquely small profile device. This inventive cardiac timing device can be used in the coronary venous or arterial system to record motion, pace and sensing electrical signals. The inventive cardiac timing device can be used in the manner of a typical guide wire as a rail that a catheter would then follow to the location where it is permanently implanted. The device embodiment provides an opportunity to identify the optimum location for the permanently implantable device without the added work of placing a larger and less steerable implant device.

Figure 5:
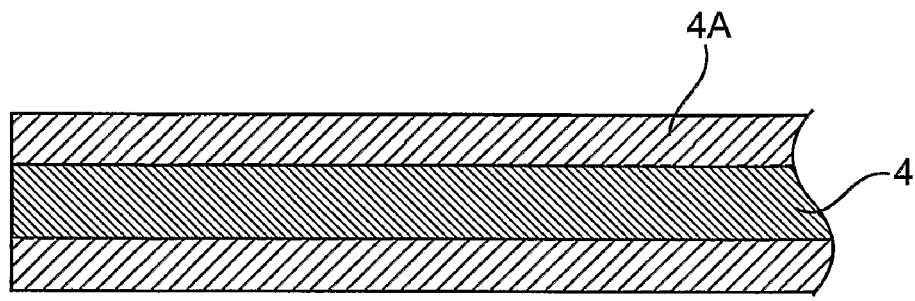
FIG. 5 provides a depiction of a proximal end of an optical fiber material guide wire.
Figure 6:
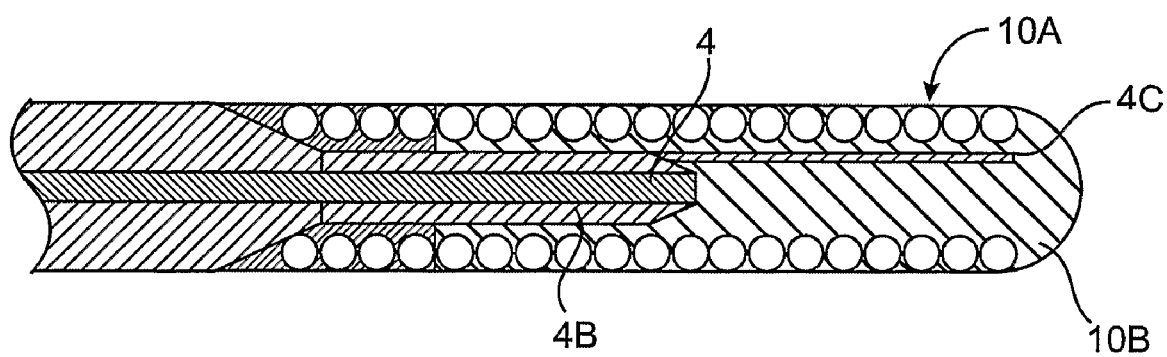
FIG. 6 provides a depiction of a distal end of an optical fiber material guide wire.

An additional embodiment for guide wire strain gauge device incorporates an optical fiber material guide wire 4 which is situated through the center of the device running from the proximal end shown in FIG. 5, to the distal end shown in FIG. 6. The optical fiber resides in the center core of the guidewire. In the proximal section, it is located inside a stainless steel tube 4A of approx 155 cm length with an outside diameter of 0.0135 inches. In the distal section of the device shown in FIG. 6, the optical fiber is inside a smaller stainless steel tube or Ni—Ti supper elastic tube 4B with an outside diameter of 0.0075 inches. The distal and proximal tube sections are bonded together with a soldering process or adhesive bonding. The distal metal tube is ground down to smaller diameters as it nears the distal tip. A small rectangular wire 4C would extend to the distal tip. This final wire is typically referred to as a safety wire.

The distal construction is located inside a long metallic coil, such as made of stainless steel, with a distal 2 cm section of Pt-10Ir wire 10A. The outside diameter of this coil is 0.0135 inches. The whole construction can optionally be coated with PTFE or it can be over molded with a polymeric material 10B. Alternate embodiments can eliminate the coil. The device can be over molded with a polymeric material to make the final diameter of the device uniform.

Figure 7:
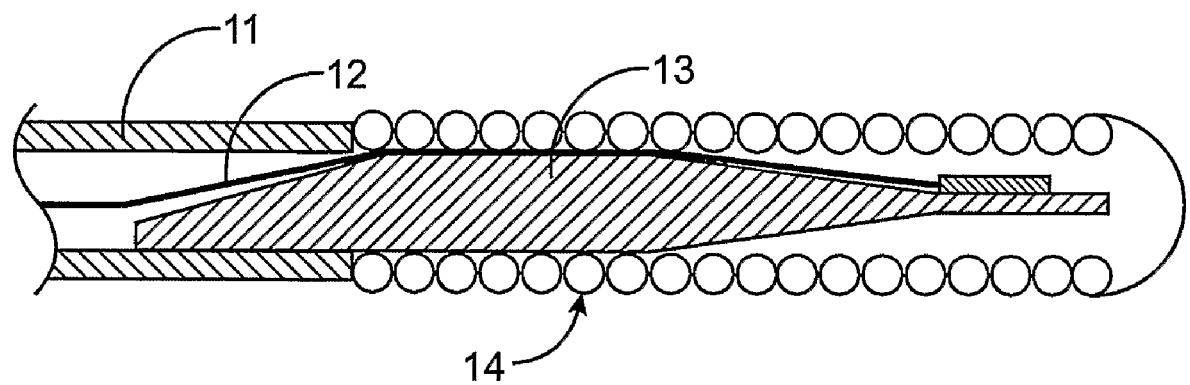
FIG. 7 provides an alternate configuration for a guide wire strain gauge device according to an embodiment of the invention.

FIG. 7 provides an alternate configuration for the guide wire strain gauge device. In this configuration, the central conductors 12 run through a heavily coiled worked stainless steel tube commonly referred to as a "hypotube" 11 with a typical diameter of 13.5 thousandths. Conductors 12 are inserted into the center of the hypotube typically 160 cm long. They exit through a feature where a taper is ground into a piece of stainless steel core wire 13 that has a proximal taper grind forming a small gap. The central conductors 12 are fed underneath the typical metallic coil 14, and the taper flat ground core wire item 13. The central conductors 12 then flow in-between the gap between stainless steel core wire 13 and metallic coil 14. This construction is essentially similar to what has been described previously for FIG. 4.

Figure 8:
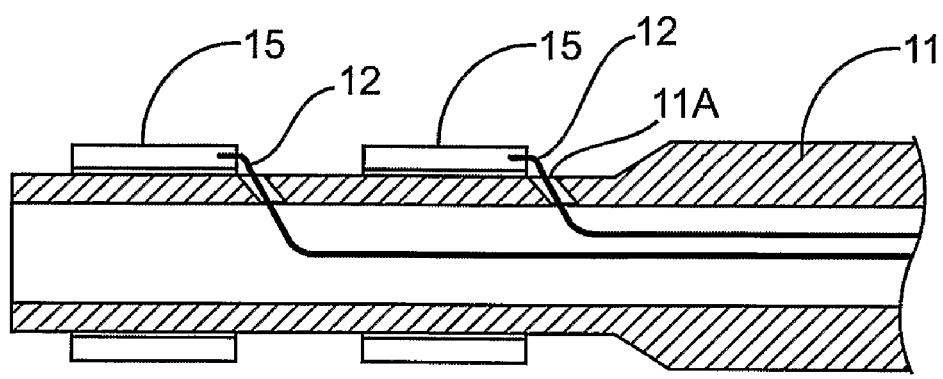
FIG. 8 shows the proximal construction of a guide wire embodiment of the invention.

FIG. 8 shows the proximal construction of a guide wire embodiment of the device. The hypotube 11 has laser drilled holes 11A. The conducting wires 12 are pulled out of those holes, stripped and welded to conducting rings 15. Electrical connection is then made with equipment that would analyze the strain gauge signal.

Figure 9:
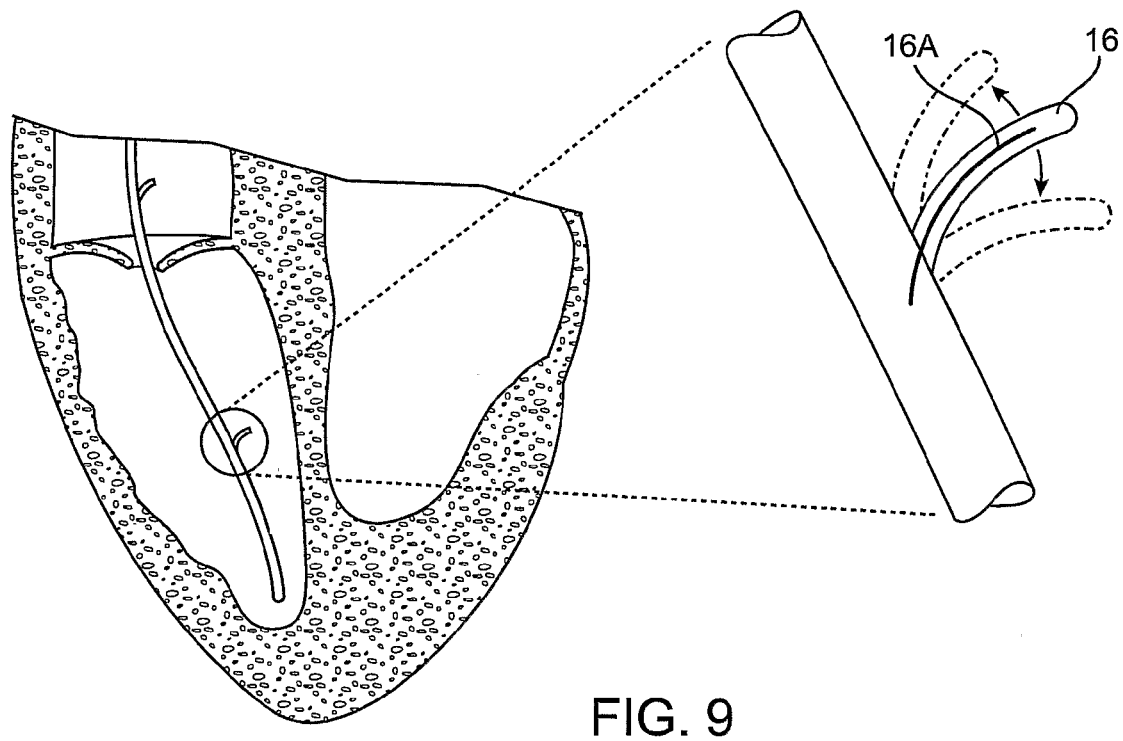
FIG. 9 shows strain gauges to measure blood flow and timing measurement along the length of a catheter.

FIG. 9 provides an additional device configuration using strain gauges to measure blood flow which then provides a timing measurement along the length of a catheter. When combined with a calibration of the force required to deflect the flap 16 with the strain gauge, this configuration provides an alternate method of measuring blood flow from the current devices, such as a Swan-Ganz catheter. In this inventive configuration, the catheter is provided with small flaps 16 where a strain gauge 16A is located in the middle of the flap. As the blood flow goes past the small flaps 16, small flaps 16 would move the strain gauge, producing a signal which provides the clinician with an indication of blood flow and blood pressure. Additionally, through calibration, the clinician will have the opportunity determine the direction of blood flow.

Figure 10:
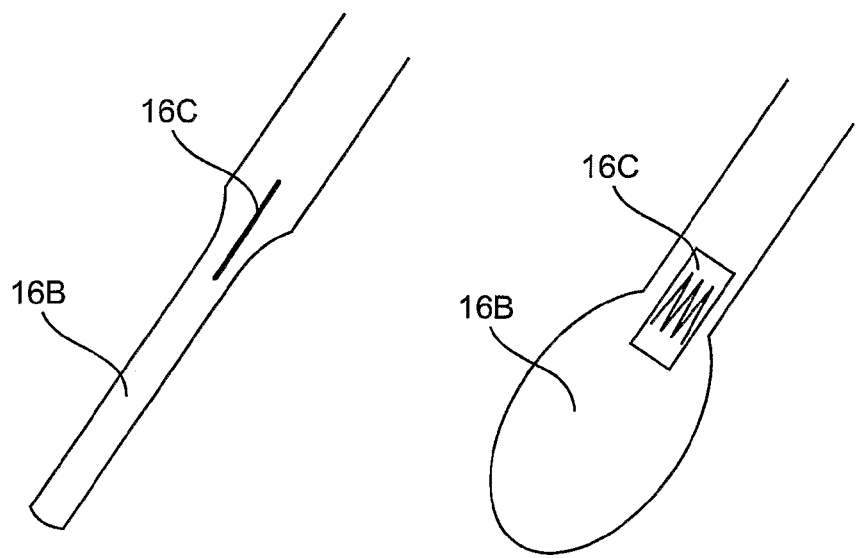
FIG. 10 shows a device with a wider section of the catheter and lower bending stiffness.

FIG. 10 provides an alternate design for that device which has a wider section of the catheter that has a lower bending stiffness. In this case, strain gauges 16C are implanted in a wider section of material that would work as a paddle 16B. With this configuration, the strain gauge will move as the blood flow moves the wider section of the catheter. This configuration provides the user with timing of blood flow and magnitude and direction of blood flow. The above embodiments provide a general description of the strain measuring of cardiac timing.

Figure 11:
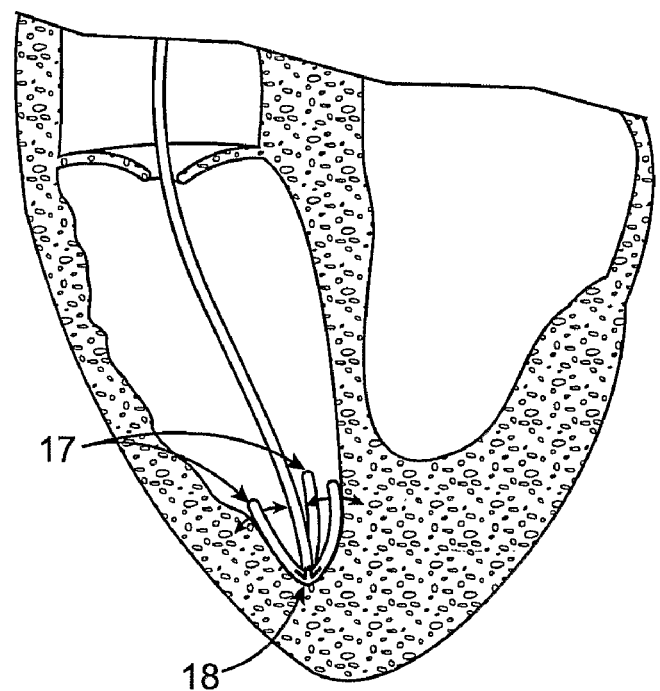
FIG. 11 shows a lead with an umbrella pattern of tines.
Figure 12:
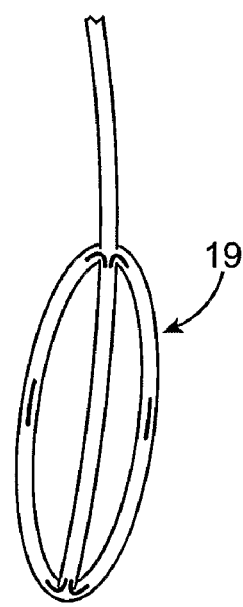
FIG. 12 shows lead with an umbrella pattern of tines forming a basket.

FIGS. 11 and 12 provide an additional embodiment of the device wherein the device is formed into an umbrella array that extends to contract the heart chamber. There are a large number of shape and configuration variations that are obvious and would perform the same functions. These shapes include S bends, corkscrews, umbrella patterns and baskets. These patterns can be mechanically deployed for temporary use. Alternatively, they can be formed into permanent shaped cardiac timing devices for implant applications. These embodiments allow the placement of stain gauges at multiple locations in the cardiac chambers to provide timing of local wall motion. Pacing and other sensors could be included on these devices.

For cardiac motion sensing, strain gauges at multiple wall locations can provide a higher degree of granularity for detecting non-uniform wall motions. In addition, non-synchronous motion of the left ventricle can be detected by strain gauges in contact with the inter-ventricular septum.

FIG. 11 describes a lead with an umbrella pattern of tines 17. These long tines are typically formed of silicone or polyurethane. Strain gauges are inserted either at the base 18, mid section, or distal section of the tines 17, providing contact on multiple walls inside the cardiac chamber. In this view, the strain gauges are located at the apex of the heart, but would not be limited to that location.

FIG. 12 shows a similar type of structure, where a basket 19 is formed of silicon, polyurethane, or metallic members. The basket 19 can either be formed prior to the procedure in manufacturing to conform to the inside shape of the cardiac chambers. Alternatively, a wire can be pulled to extend the basket to create contact with the inside surface 19 of the cardiac chamber. Those features may contain strain gauges at the connection points with those to the main body or in the mid section of the arms that are extended out.

FIG. 13 provides an additional embodiment for measuring timing of tissue motion with the strain gauge by incorporating strain gauges into a coil that would be screwed into the tissue of the heart. By example, the strain gauges may be screwed into the apex of the heart or in to the septal wall between the right and left ventricle. Many other locations are also useful targets for attachment. The affixing coil 20 is typically similar in size to pacing tip coils that are well known in the industry. In one fabrication approach, a series of strain gauges 22 on a flexible substrate 21 can be inserted inside the coil 20 after it has been formed. The coil can be filled with a material to couple the strain gauges to the motion of the coil. That material could be a polymer material like epoxy. Additional sensors 23 can be attached to the flexible substrate and incorporated into the construction. These sensors could be pressure sensors, chemical sensors or other sensors that would provide clinically useful information. The tip of the coil can be sealed by welding if there is not a sensor at the tip. The tip of the coil can be kept open if there is a sensor that required contact with blood or tissue. The area around the sensor can be sealed with a polymer or a low melting temperature glass. During use, the coil is screwed into the tissue so that it is embedded or, for a design with a sensor, it could be made long enough so the sensor was protruding through the other side of the tissue wall. In one embodiment the sensor could extend into the left ventricle by being screwed in through the right ventricle.

FIG. 14 provides a view where the coil 20 is welded and sealed at the end, and subsequently welded to a cap. The cap houses the connections of the strain gauges 21 to conductor wires that exited the body of the catheter. The strain gauges 21 are mounted on a flexible substrate. This assembly can then be potted with an epoxy or other suitable material. As a result, strain gauges 21 will experience a strain that the coil was experiencing as it was screwed into the tissue.

Compression, tensile and shear stresses in the tissue wall would produce a timing signal to be registered by the strain gauges. This provides a specific, very localized measurement of tissue motion deeper into the tissue. A multiplicity of strain gauges 21 provide a reading indicating the direction of that motion and the magnitude of that motion, in addition to timing. This device configuration, in combination with a pacing electrode the outside of the corkscrew device may be constructed similar to a screw tip pacing electrode that was made out of platinum iridium and then coated with coatings that are know in the industry, iridium oxide.

In addition, this device may be provided with a pressure sensor located at the tip, and the device screwed through the septal wall to measure left side pressures as an implant device. Strain gauge 21 is located in the center of the coil, which is then provided with filling 22, such as epoxy or other suitable material. This filling 22 provided within coil 20, which can be formed of such materials as platinum iridium, producing a fine coil of similar dimensions to pacing tips. At the tip, strain gauges 21 can be provided in a multiplicity of locations. Strain gauges 21 may be fabricated on a flex circuit that is typical construction for strain gauges. A pressure sensor 23 of FIG. 13 can optionally be incorporated on that flex chip and then exposed at the tip. A pressure sensor in this case is exemplary only, as many other sensors could be usefully incorporated as well.

FIG. 15 provides a view of a minimalist configuration where the whole sensor is scaled down to a smaller diameter by producing the coil from a good strain gauge material, e.g., from platinum alloys, such as Pt-10% Ir or Pt-8% W. The device is filled with a conductor that then makes electrical connection at the tip. The net result is a very tiny pacing tip 26 that can also serve as a strain gauge. This is accomplished by using the coil itself to measure the change in resistance as it experiences the tidal forces of the contractions of the cardiac tissue.

From the physicians perspective this device would appear exactly the same as screw tip pacing leads that are in common use. It would provide additional strain or timing data for the pacing tip in addition to providing electrical signals at the screw tip.

As such, designs for localized measurement of cardiac timing is described in FIGS. 13, 14, and 15. In these configurations, strain gauges are incorporated into a screw tip similar to screw in pacing tips for cardiac pacing leads that are well understood for artisans. These representative embodiments produce timing signals at the local site where the device is screwed into the cardiac tissue. In addition, these configurations allow timing of the motion of internal tissue. These configurations are of great advantage for measuring the motion of the thick cardiac ventricular septum. It is understood that measuring the timing of the motion of the cardiac septum is of great value for improving the timing between the right and left cardiac ventricle. The screw tips also have the capability to serve dual purpose as a pacing and sensing electrode.

Figure 16A:
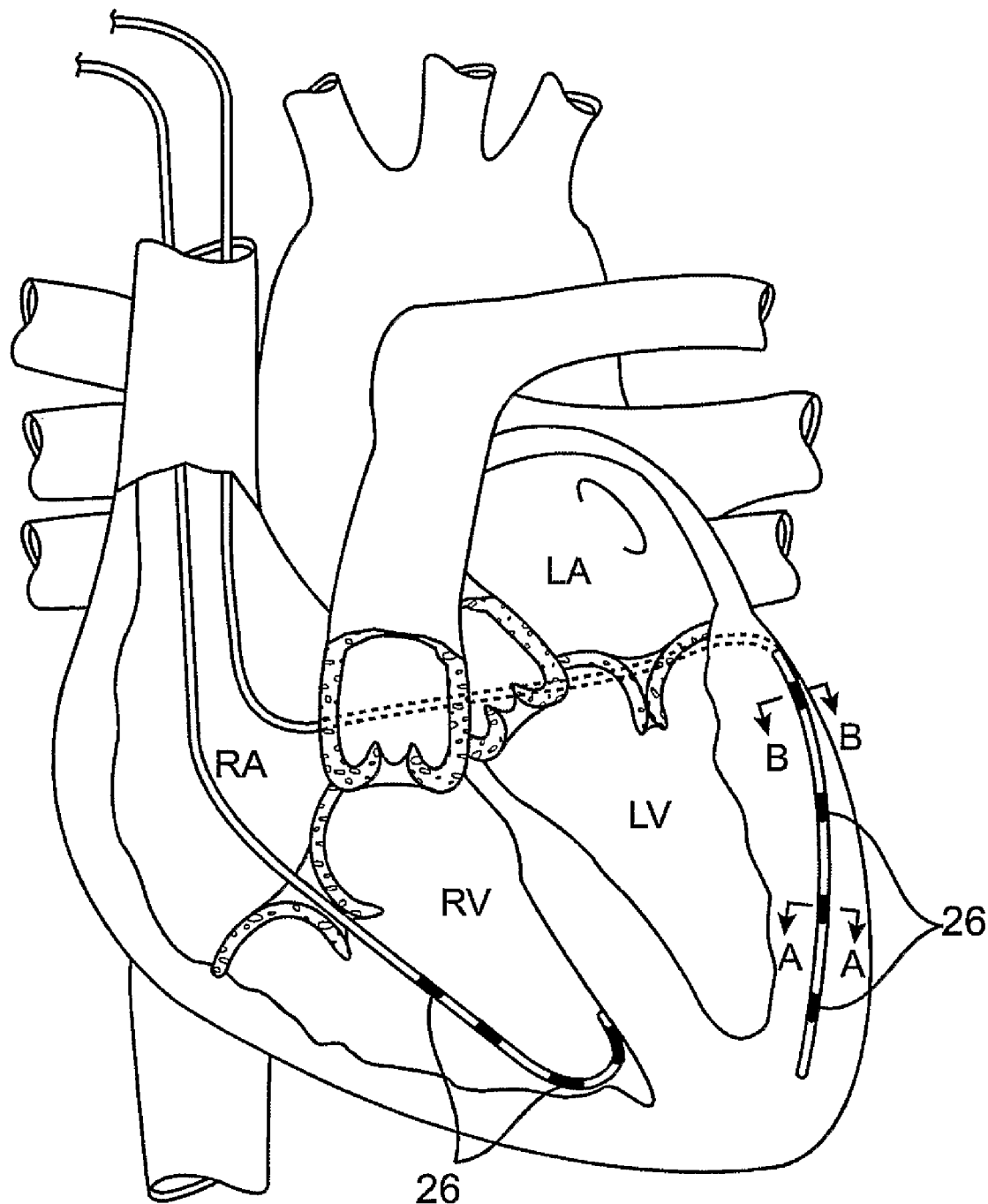
FIGS. 16 A to E show various placements of the device in the heart and alternate configurations.
Figure 16B:
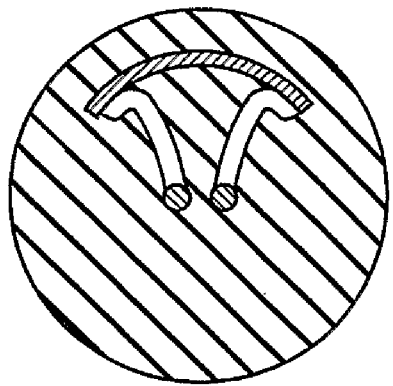
Figure 16C:
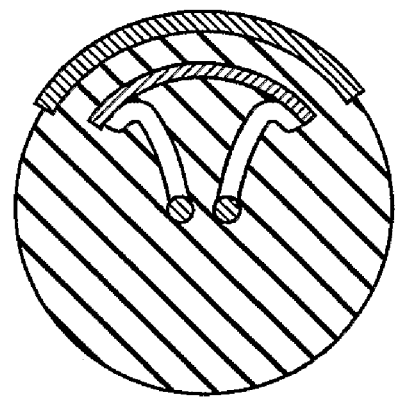
Figure 16D:
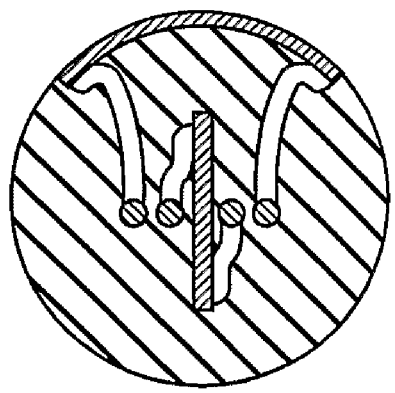
Figure 16E:
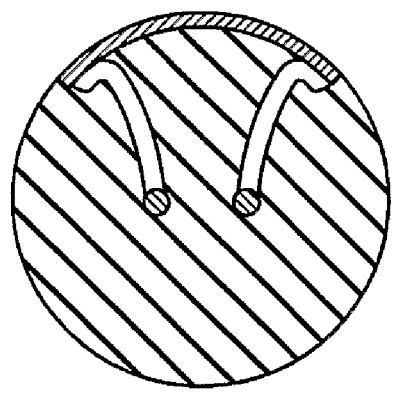

FIG. 16A refers to the general description of the inventive device in the general embodiment of the device showing in this example a lead with an descending down the descending venous structure with strain gauges 26 at a multiplicity of locations to provide timing information for cardiac motion along a long segment of left sided, left ventricle tissue. In addition, a U-shaped lead device can be placed inside the right ventricle or it could be placed in the pericardial space. FIGS. 16B, 16C 16D and 16E provide generalized placements of strain gauges in the body of the device.

Figure 17A:
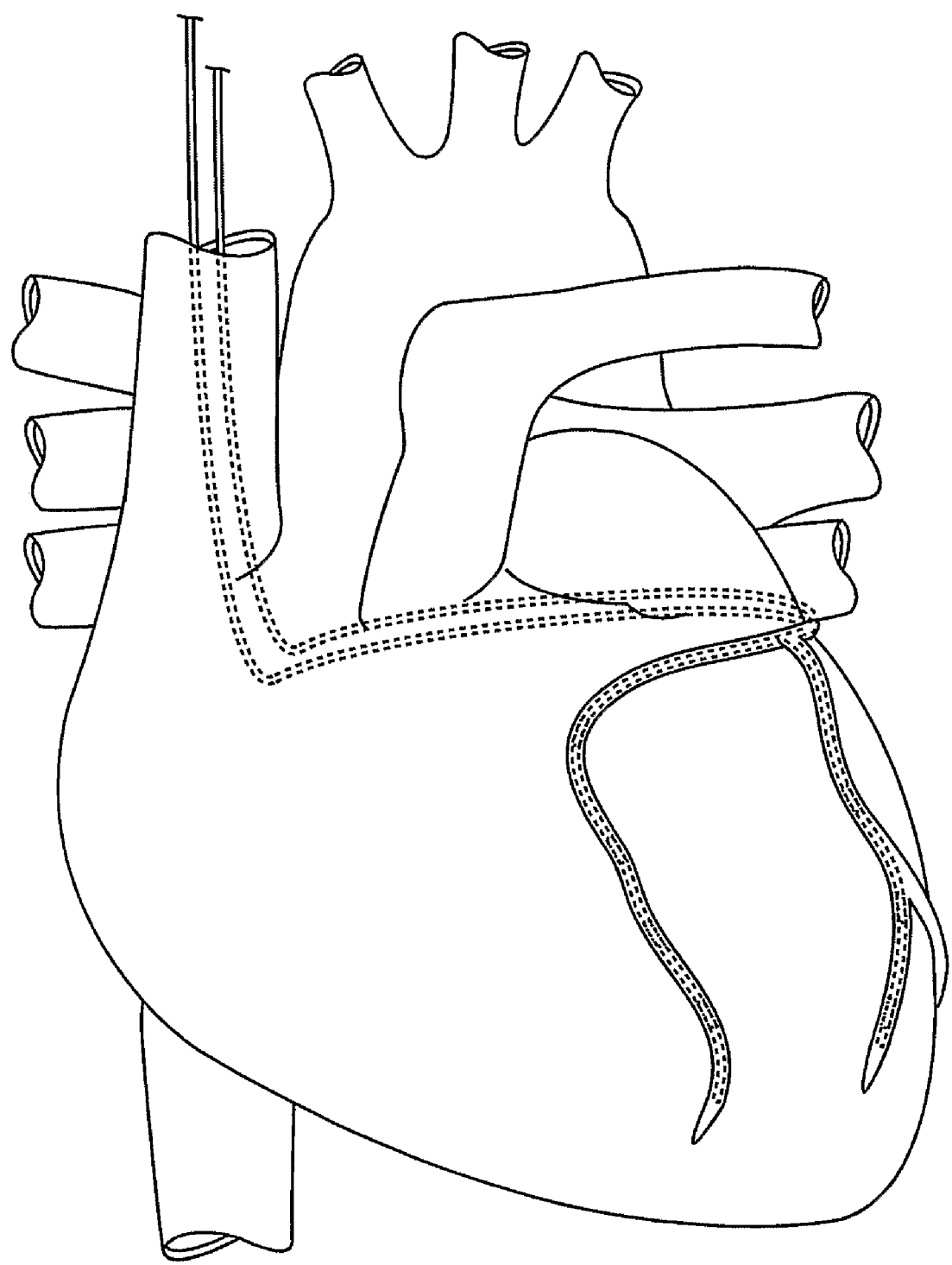
FIGS. 17A to C show various device placements, with FIG. 17D showing a stent embodiment.
Figure 17B:
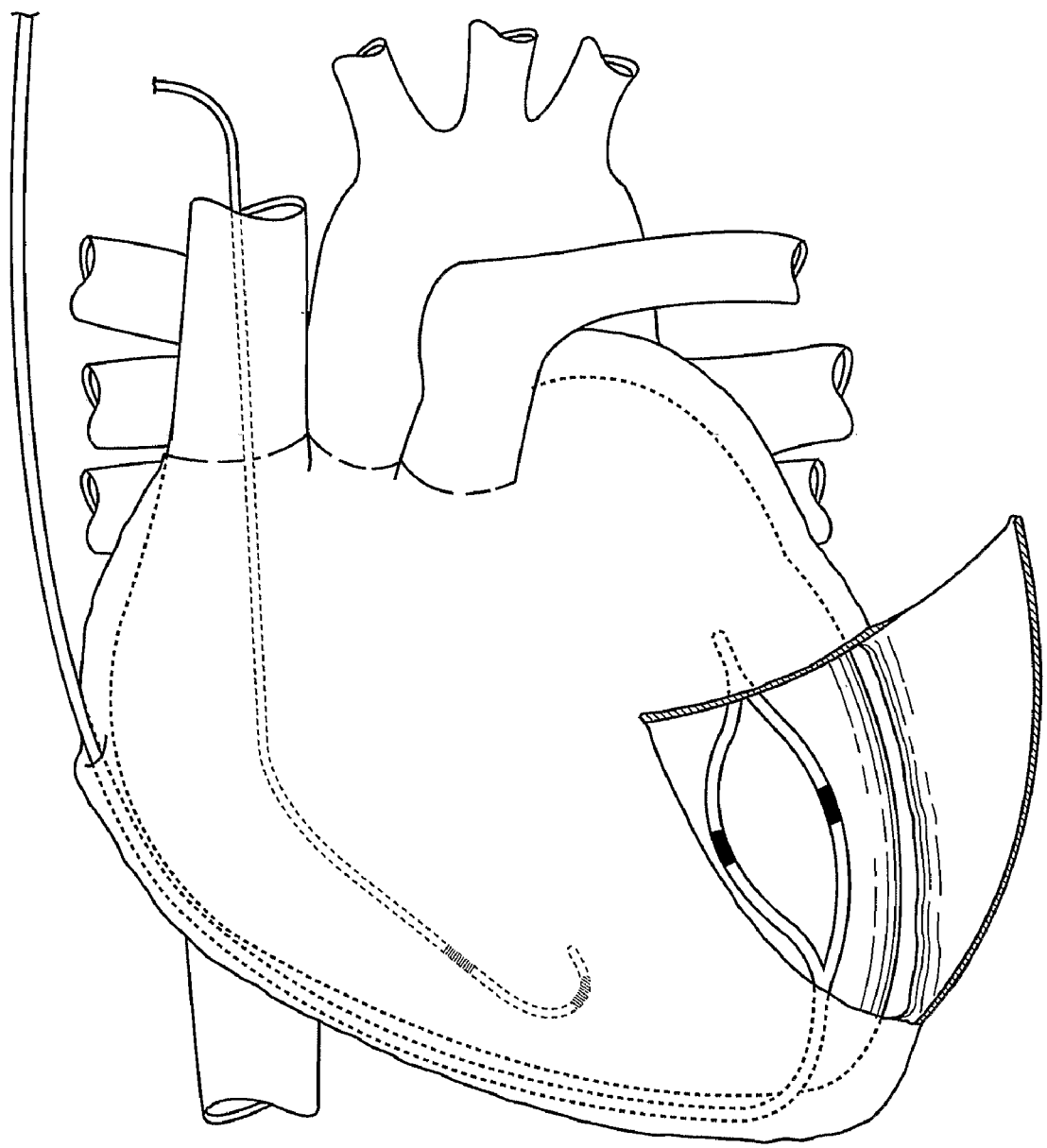
Figure 17C:
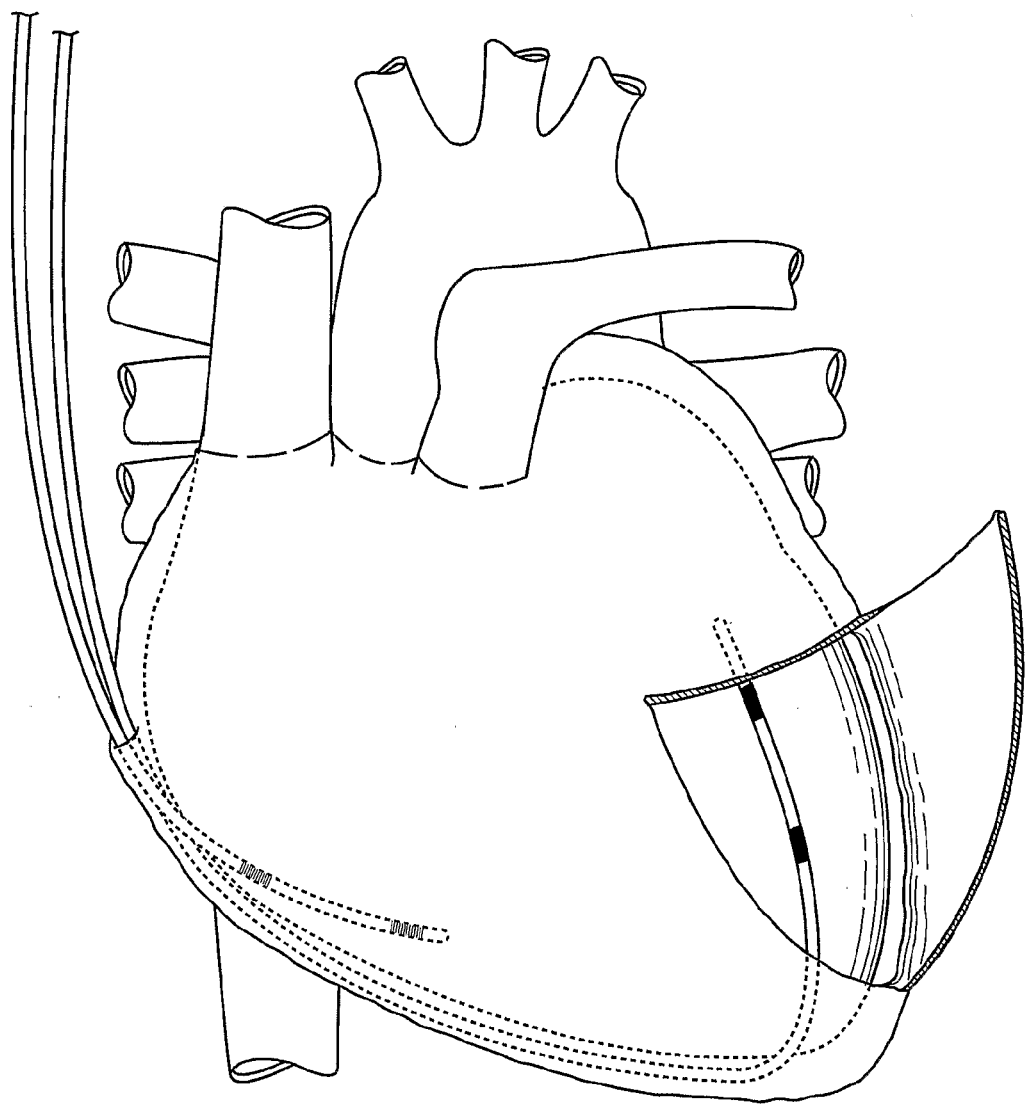

FIG. 17A shows two devices used simultaneously in the descending venous system after passing the coronary sinus vein. FIG. 17B shows a device placed in the right ventricle and another device placed on the outside of the epicardial and under the pericardial sack. The device under the pericardium can have a multiplicity of sections each with a strain gauge to measure motion timing of the left ventricle. FIG. 17C shows two devices, both of which are placed between the pericardial sack and the epicardium.

This device has obvious uses beyond cardiac timing measurement. It can be used for measuring contractions in the stomach to provide a feedback loop for stomach pacing devices. Stomach contractions could be measured by this device and pacing for control of obesity could be turned on at the appropriate time.

This device could also be used to measure diaphragm motion for devices that are used to pace the diaphragm. This device of similar construction could be used to measure contractions during labor. Additionally, the inventive device could be used in other parts of the body where an electrical signal may not be available but timing could be determined from the sensing of motion. In yet another application, this device when implanted in the bladder can detect the extension of the bladder to allow for timing of electrical signals to the sphincter to allow for control of incontinence.

Figure 17D:
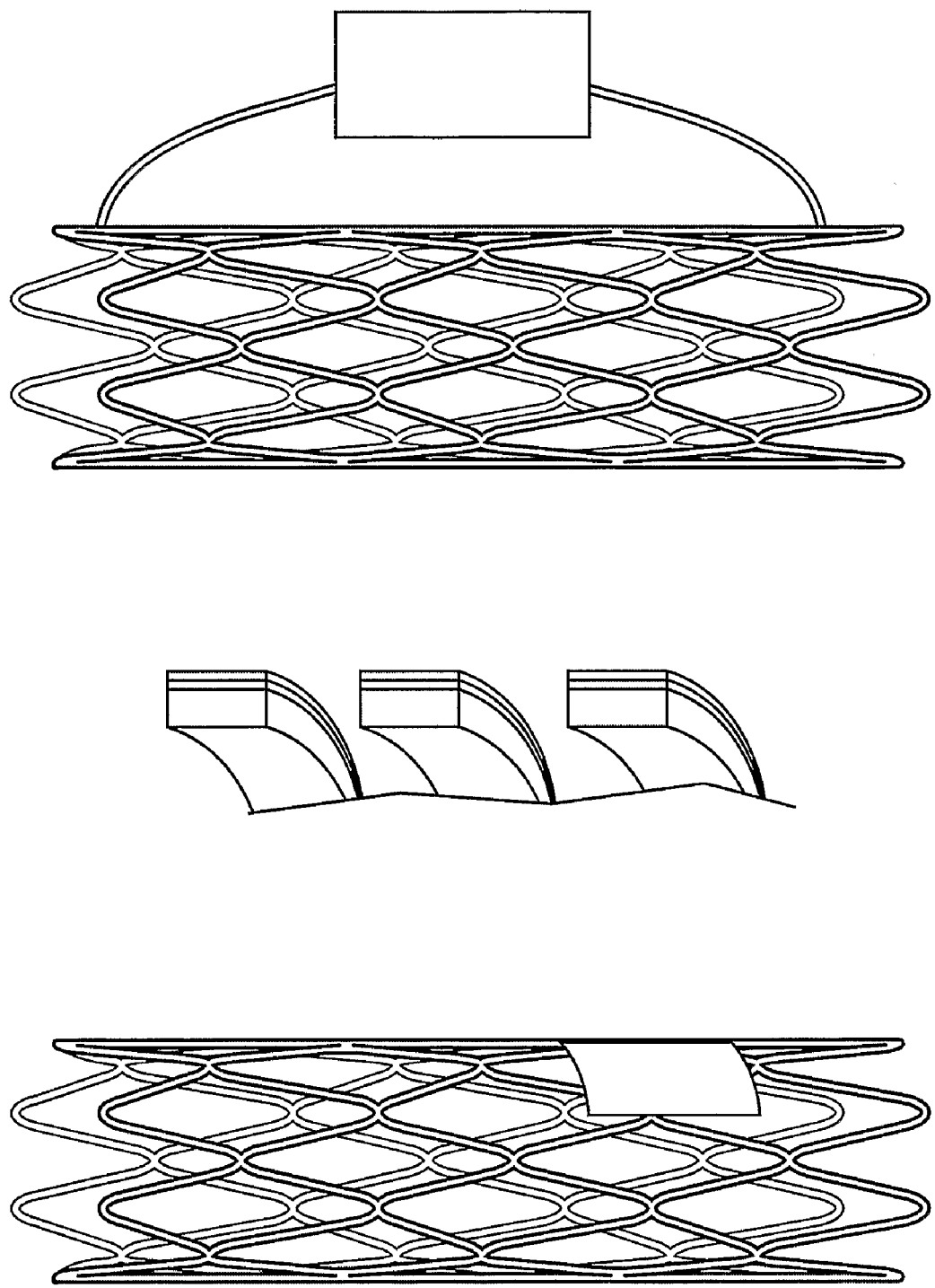

An alternate embodiment of the invention incorporates strain measurements into the body of a stent or stent graft, as is shown graphically in FIG. 17D. A metallic vascular stent is typically constructed of high yield point metals for a high fatigue life. Those same alloys, due to their composition, enable them to act as a strain gauge. The use of these devices in this entirely novel capacity allows the structure of the device itself to work as a strain sensor. This would also the device to provide timing and motion data.

The strain gauge can also be provided as a film applied to the surface of the device separated from the body of the device by a polymeric or ceramic insulator. The polymeric insulator would typically be polyimide, PEEK. The ceramic insulator would typically be SiN or $SiO_2$. The strain gauge can be sputtered or plated Pt, Pt-10Ir, Ni—Cr, Pt-8W or other suitable metal. The strain measurements can be taken over the length of the device or in multiple locations along the length or around the circumference.

This device provides measurements of blood flow timing and blood pressure. In addition, this device can provide information on aneurisms. After an aneurism is stented or has a stent graft is implanted the strain measurements provides such clinically important information, such as if the aneurism continues to expand.

Figure 18A:
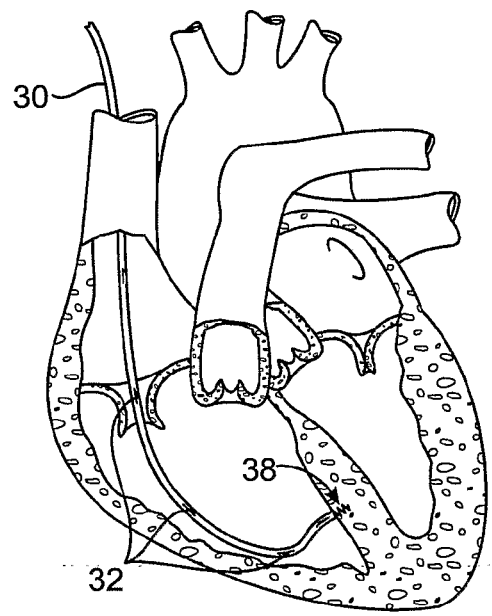
FIGS. 18A to F show a variety of placement options with various device configurations.

FIG. 18A provides a cross-sectional view of a strain gauge lead embodiment of the inventive cardiac timing device. Strain gauge lead 30 is placed in the right ventricle of the heart with an active fixation helix 38 at the end which is embedded into the cardiac septum. In this view, the strain gauge lead 30 is provided with one or multiple strain gauges 32. The distal tip of the strain gauge lead 30 is provided with an active fixation helix 38 which is screwed into the mid-septum.

Strain gauge lead 30 is placed in the heart in a procedure similar to the typical placement procedures for cardiac right ventricle leads. Strain gauge lead 30 is placed in the heart using the standard cardiac lead devices which include introducers, guide catheters, guidewires, and/or stylets. Strain gauge lead 30 is inserted into the clavicle vein, through the superior vena cava, through the right atrium and down into the right ventricle. Strain gauge lead 30 is positioned under fluoroscopy into the location the clinician has determined is clinically optimal and logistically practical for fixating the strain gauge lead 30 and obtaining motion timing information for the cardiac feature area surrounding the attachment site. Under fluoroscopy, the active fixation helix 38 is advanced and screwed into the cardiac tissue to secure strain gauge lead 30 onto the septum.

Once the strain gauge lead 30 is fixed on the septum, strain gauge lead 30 provides timing data for the regional strains and/or deformation of the septum. The strain gauges 32 which are located more proximally along strain gauge lead 30 provide timing data on the regional strains in those areas of the heart. By example, a strain gauge 32 situated near the AV valve, which spans the right atrium in the right ventricle, provides timing data regarding the closing and opening of the valve. Furthermore, strain gauges 32 situated along other portions of the lead provide local blood flow data. Such information is important in provided cardiac timing determinations.

In a preferred embodiment, strain gauge lead 30 is constructed with the standard materials for a cardiac lead such as silicone or polyurethane for the lead body, and MP35N for the coiled or stranded conductors connected to the strain gauges 32. Alternatively, these device components can be connected by a multiplex system, as describe above, to the proximal end of strain gauge lead 30. The proximal end of strain gauge lead 30 connects to a bridge completion module for strain gauges 32, an amplifier, and other such display units to provide timing data from the various strain gauges 32.

The strain gauge lead 30 is typically fabricated of a soft flexible lead with the capacity to conform to the shape of the heart chamber. The only fixation point in this embodiment of the present cardiac timing device is the active fixation helix 38 which is attaching the strain gauge lead 30 to the cardiac septum.

Figure 18B:
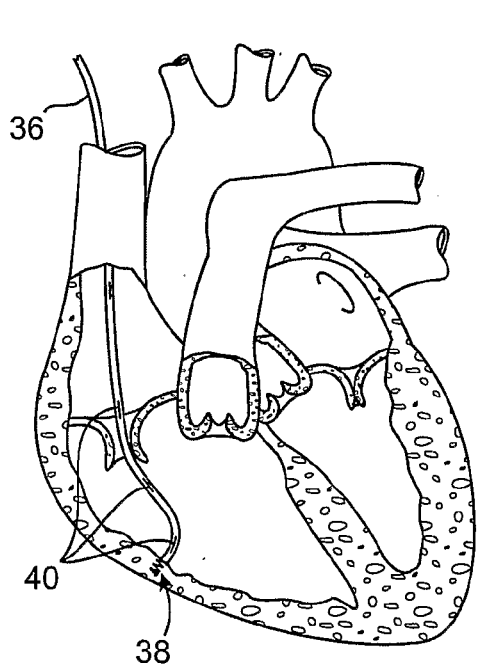

FIG. 18B provides a view of a strain gauge lead 36 with an active fixation helix 38 on its distal end, but with a different site of attachment. Strain gauge lead 36 has one or more strain gauges 40 embedded along its length. Strain gauge lead 36 is physically identical to strain gauge lead 30 shown in FIG. 18A. The primary difference between these two views is that in this the distal end of the strain gauge lead is screwed into the lateral wall of the right ventricle.

The clinical motivation for these fixation alternatives is to provide cardiac timing information via strain gauge leads 36 and 30 about the regional strains or motions of the cardiac tissue where they are fixated. In FIG. 18A, the strain gauge lead 30 attached to the septum will provide cardiac timing data primarily for septal motion. In FIG. 18B, strain gauge lead 36 is attached to the lateral wall of the right ventricle, and will give cardiac timing data primarily regarding the motion of that portion of the heart.

Figure 18C:
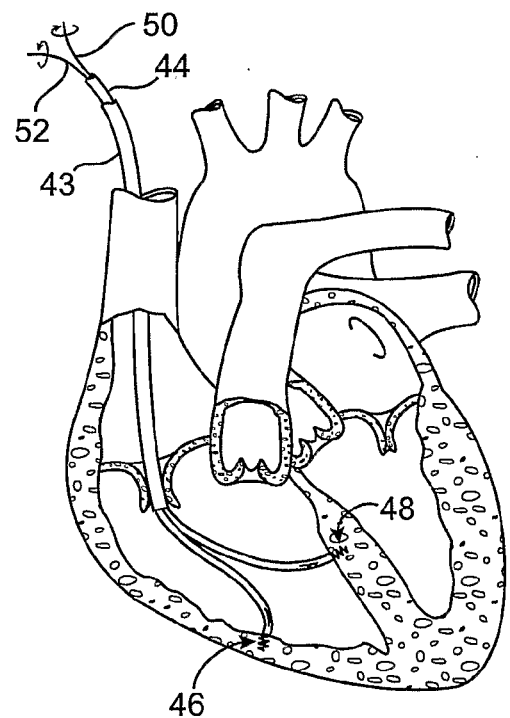

FIG. 18C provides a view of a bifurcated strain gauge lead 44 being placed with a guide catheter 43. In order to place the bifurcated strain gauge lead 44, the guide catheter 43 tip is first placed into the right ventricle and then the bifurcated strain gauge lead 44 is slowly advanced through the guide catheter 43. As the bifurcated strain gauge lead 44 enters into the right ventricle, it is released from the laterally confining guide catheter 43, and unfurls into its intrinsic bifurcated shape. Under fluoroscopy, bifurcated strain gauge lead 44 is advanced until the two distal tips 46 and 48 are in the desired location on the heart such as right lateral wall location 46 and septal wall location 48. Once distal tips 46 and 48 are in a desired position, torque wires 50 and 52 are used to advance the active fixation helixes and screw them into the tissue. Alternatively, passive fixation with tines can be employed to stabilize bifurcated strain gauge lead 44.

The inventive embodiment described in FIG. 18C enjoys number of advantages over the non-bifurcated embodiments. The bifurcated configuration of the inventive cardiac timing device allows, in a single deployment procedure, the placement of two active fixation helixes on two different regions of the heart. Thus, a considerable increase in cardiac timing information can be obtained in a single procedure. An additional advantage of this device configuration is that there is a more controlled reference position between distal tips 46 and 48 than would be available with individual placement. Also, for accelerometers which are measuring motion within the ventricle, the bifurcated type placement allows more predicable and stable positioning.

Figure 18D:
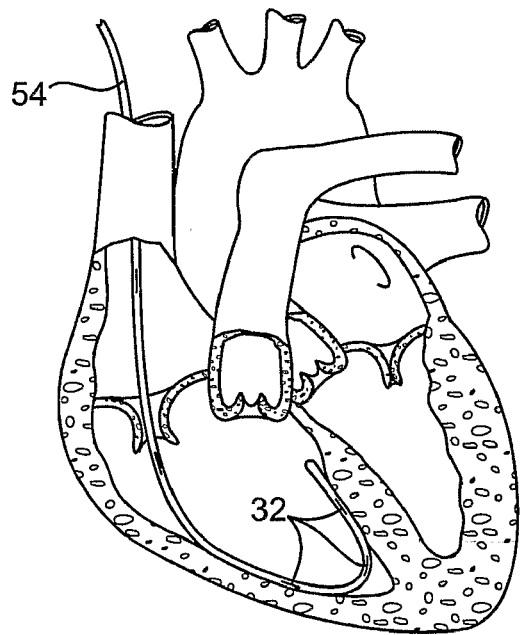

FIG. 18D provides a view of a U-shaped strain gauge lead 54. This diagram shows the position of U-shaped strain gauge lead 54 after deployment in the right ventricle. U-shaped strain gauge lead 54 is provided with one or more strain gauges 32 along its length. The main motivation for U-shape configuration is to guarantee contact of the strain gauge lead with two walls of the heart, such as the septal wall and the right ventricle lateral wall.

U-shape strain gauge lead 54 is deployed using a guide catheter which would be placed into the right ventricle. The straightened U-shape strain gauge lead 54 is then slowly advanced out of the guide catheter. As it exits the guide catheter, U-shape strain gauge lead 54 assumes its intrinsic U-shape within the right ventricle. Alternatively, a straight stylet placed within U-shape strain gauge lead 54 can be used to hold the lead in a straight position during initial right ventricle placement. Once the lead is placed in the right ventricle, the stylet is removed and U-shape strain gauge lead 54 assumes its intrinsic U-shape.

The fabrication of the U-shape can be accomplished through a number of known methods. By example, the silicone lead body can be molded as a U-shape during the processing. Alternatively, the metal conductor coils or strands within the lead body can be shape set into a U-shape using various heat treatment methods.

U-shaped strain gauge lead 54 may optionally include an active fixation helix (not shown) along the length of the lead to fixate it as shown in the figures above. However, such additional fixation need only be provided when there is an unusually demanding cardiac feature target area preferred for fixation, or the point of attachment needs to be highly precise. In a representative embodiment, U-shaped strain gauge lead 54 does not require an active fixation, but by the nature of its U-shape holds this position within the ventricle chamber of the heart. In operation of certain embodiments, during systole and diastole of the heart, the U-shaped strain gauge lead 54 flexes back and fourth and shifts slowly up and down. One of the advantages of the U-shape is that it gives a direct correlation of timing and strain with the contraction timing and magnitude the septal and right ventricle walls.

Figure 18E:
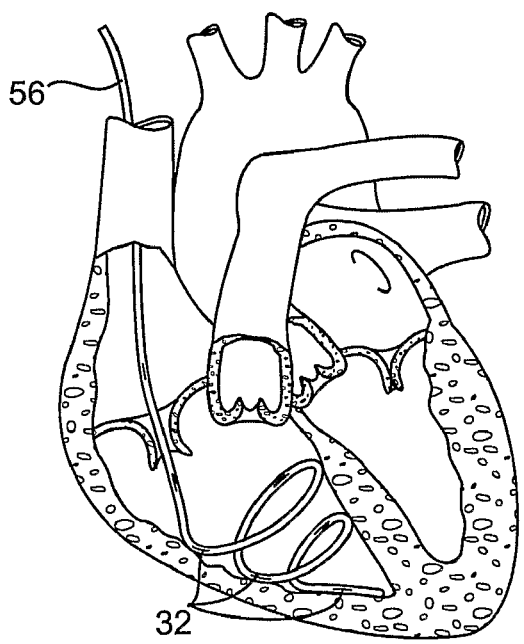

FIG. 18E provides a view of spiral strain gauge lead 56. As with the examples above, spiral strain gauge lead 56 includes one or more strain gauges 32 embedded along its length. Spiral lead 56 is deployed using similar guide catheter and stylet methods as described for the U-shape strain gauge lead 54. As with U-shaped strain gauge lead 54, the primary purpose of the spiral shaped lead is to guarantee contact with the side walls of right ventricle chamber. In this case when the chamber contracts, the spiral lead flexes and a strain would be measured on its one or more strain gauges. The strain gauges provide regional timing and strain information at the various positions where the strain gauges come in contact with the right ventricle walls. Another option is to have an active fixation helix on the distal tip, but in the preferred embodiment shown in FIG. 18E, there is no active fixation.

Figure 18F:
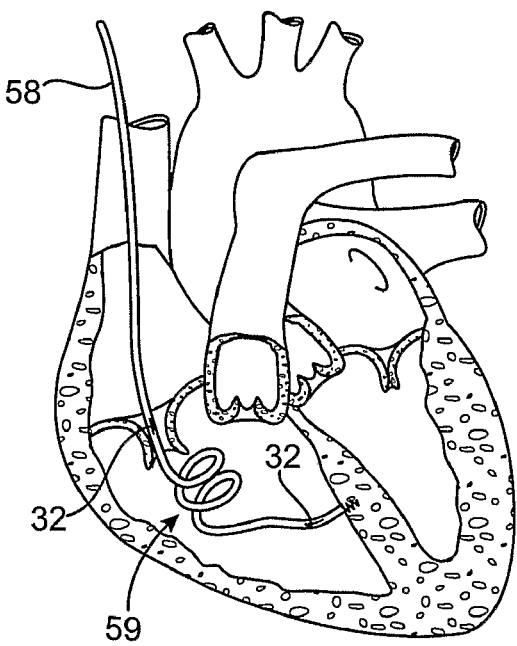

FIG. 18F shows strain gauge lead 58 with coil segment 59. In this view, the strain gauge lead 58 has been installed within the right ventricle and right atrium. The strain gauges 32 are separated from one another by coil segment 59 on the strain gauge lead 58. The function of coil segment 59 is to create independent or free floating segments of the lead which can flex without influencing each other. By example, in some of the previous configurations, there is the potential for direct influence of movement of one portion of lead on another simply due to the natural stiffness of the lead. The main goal of the embodiment shown in FIG. 18F is to isolate these segments using a very flexible coiled segment 59 in the strain gauge lead 58. One of the advantages of a multiple coil device configuration is that multiple coiled segments provide substantial mechanical isolation of the different strain gauges 32 from each other. The cardiac timing data then received from the various strain gauges 32 then give highly accurate data specific for regional motions or strains in the heart along the strain gauge lead 58.

In the inventive configurations of FIGS. 18A to 18F, the lead is described as being embedded with strain gauges. In another embodiment of these configurations, piezoelectric films can be used in place of strain gauges. Such piezoelectric sensors provide cardiac timing data by sensing deformation at each location where the piezoelectric film sensors are embedded. One of the advantages of using a piezoelectric film, such as polyvinylidenefluoride (PVDF), is that such devices would not need to be powered. Piezoelectric films have the capacity to generate a voltage when they are deformed. The voltage which is generated is proportional to the rate of deformation of the sensor.

Figure 19A:
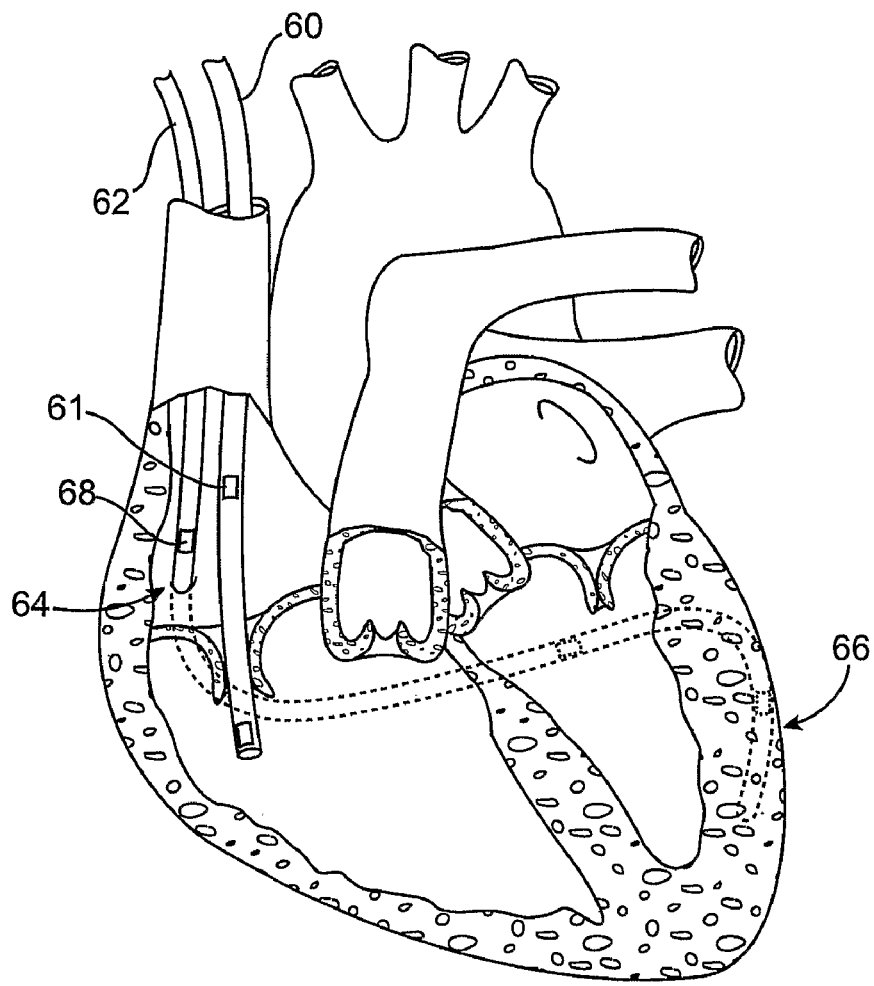
FIGS. 19A and B depict a strain gauge guide catheter.

FIG. 19A depicts a strain gauge guide catheter 60 which can also be in the form of an introducer, sheath, sleeve or other catheter type component of a catheter delivery system. FIG. 19A shows the guide catheter 60 which has been placed into the right ventricle. The guide catheter 60 is embedded with one or more strain gauges 61 along its length. There is also a second strain gauge guide catheter 62 which has been placed through the coronary sinus 64 and into the cardiac vein 66. Also embedded along guide catheter 62 are one or more strain gauges 68.

The guide catheters 60 and 62 are used as part of the delivery system for cardiac leads in the right ventricle or in the right atrium, as well as in the coronary sinus and cardiac vein. During such procedures, it is advantageous for the clinician to monitor regional timing and strains of cardiac contractions along guide catheters 60 and 62 in the right atrium, the coronary sinus, the cardiac vein, and the right ventricle.

Figure 19B:
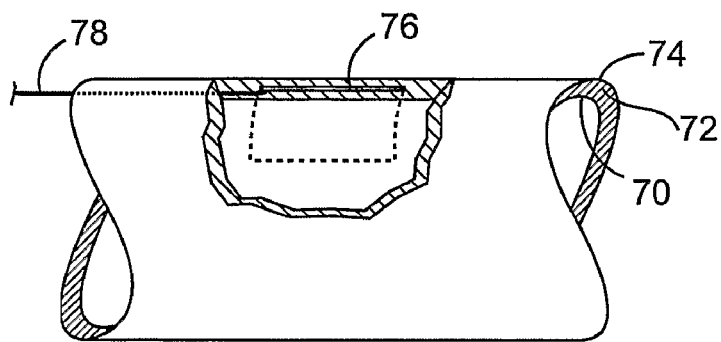

The main construction of a strain gauge guide catheter can be accomplished using well known techniques for guide catheters. Such standard fabrication methods typically involve a triple layer construction, as depicted in FIG. 19B. Typically provided is a PTFE liner 70 on the inside surface. A stainless steel braid wire 72 is placed over the PTFE liner 70. Over this construct, a nylon or other plastic material sleeve 74 is thermoformed into place. In one embodiment of the present invention, a fourth element would be placed within those layers in the form of a strain gauge 76 or piezoelectric film. In some inventive embodiments, the strain gauge 76 is placed between the stainless steel braided construction and the nylon sleeve. The strain gauge 76 would typically be provided at least two wires 78 which would connect to electrical connectors on the proximal end of the guide catheters 60 and 62.

The guide catheter which is placed into the coronary sinus can also involve a smaller strain gauge guide catheter which can then be advanced much further beyond the coronary sinus and into one of the cardiac veins. This would allow measurements of timing and strain of regional contractions near the cardiac vein and left side of the heart. Such measurement would ideally be provided by sensors situated along lateral wall of the left ventricle. The strain gauges placed on the guide catheter introduced into the right ventricle provide information about contractile timing of the lateral wall of the right ventricle and the septal wall. During the delivery of the cardiac leads, the strain gauge guide catheters are used for measuring interventricular and intraventricular dyssynchrony and thereby used to optimize cardiac resynchronization therapy variables such as location of pacing leads and pacing parameters.

Other embodiments of the inventive strain gauge guide catheter involve a strain gauge introducer, a strain gauge sheath, or strain gauge sleeve, all of which can make part of the delivery system of cardiac leads. One advantage of these configurations is the simplicity of integrating strain gauges into these catheter type devices. Another advantage is that these strain gauge catheters are compatible with already existing implantable cardiac pacing systems.

In another embodiment where there is a need for a permanently implanted strain gauge, a strain gauge sleeve is provided which is slid over a standard cardiac lead for permanent implantation.

Figure 20A:
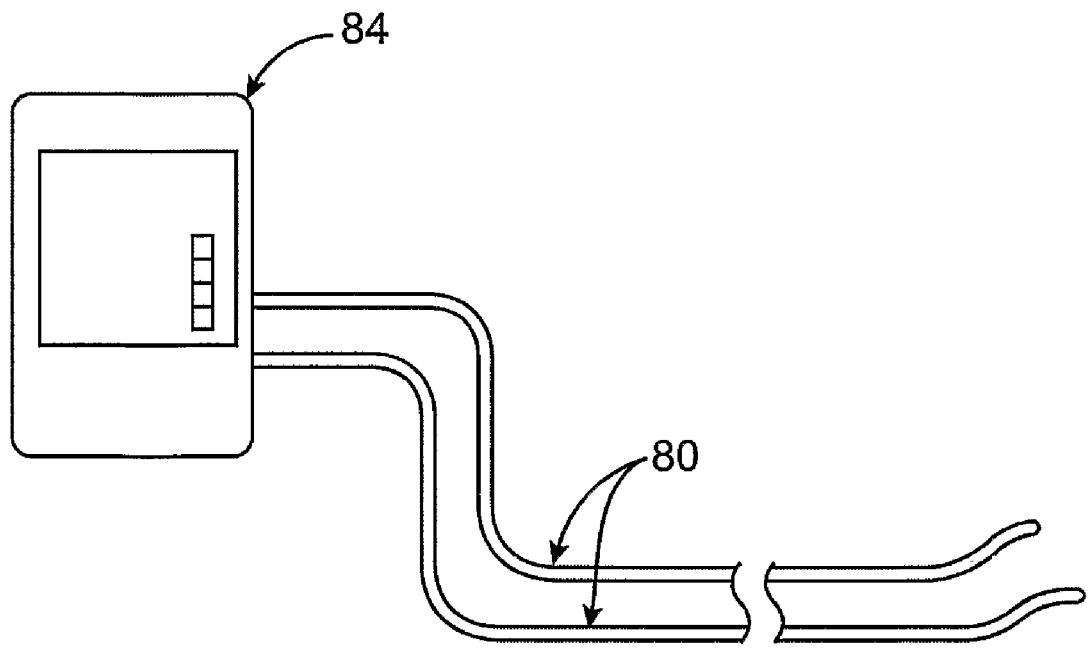
FIGS. 20A and 20B provide a view of the proximal end of strain gauge guide wire.
Figure 20B:
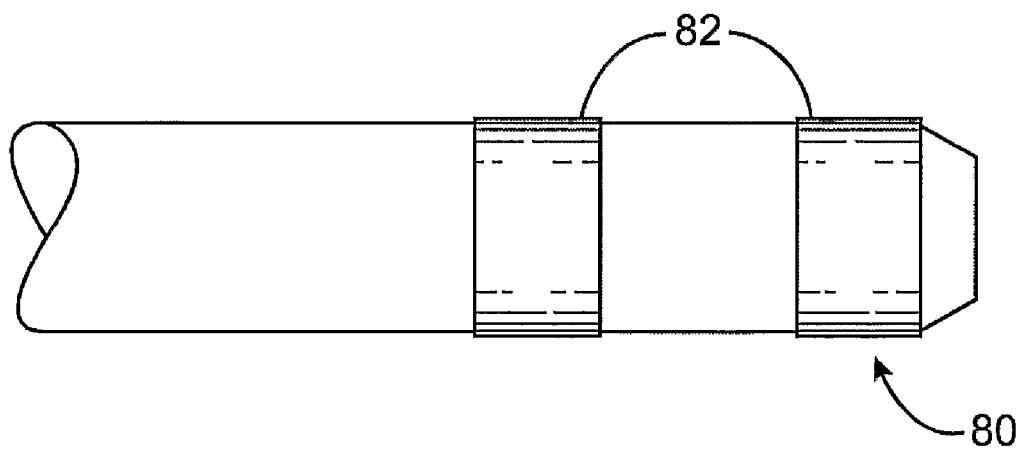

FIGS. 20A and 20B provides a graphic view of the proximal end of strain gauge guide wire 80 with two electrical contacts 82. The two electrical contacts 82 on the proximal end of strain gauge guide wire 80 are no larger in diameter than the rest of the guide wire. This dimensional configuration is important in order for the construct to be compatible with standard cardiac leads. In order to be able to insert proximal portion of the guide wire 80 into the lead and pull it all the way through, it must have a maximum diameter no larger than the cardiac lead lumen for guidewires. FIG. 20A also shows a display unit 84 that is connected to the strain gauge guide wires 80. The two strain gauge wires proximal electrical connectors are inserted into the display unit 84. On display unit 84 is shown a synchrony index display screen which would be used to optimize the cardiac resynchronization therapy of a heart failure patient. The display unit 84 also includes strain gauge completion bridge modules, amplifiers, electronics and batteries. Once the clinician is finished optimizing the pacing regimen of the patient, the guide wire 80 is disconnected from the display unit and the guide wires 80 removed from the cardiac leads.

In another embodiment of the present cardiac timing device, the same display unit 84 is connected to electrical connectors on the proximal end of the strain gauge guide catheter, strain gauge introducer, strain gauge sheath, or strain gauge sleeve shown in FIG. 19A.

Optical Strain Gauge Embodiments

Figure 21A:
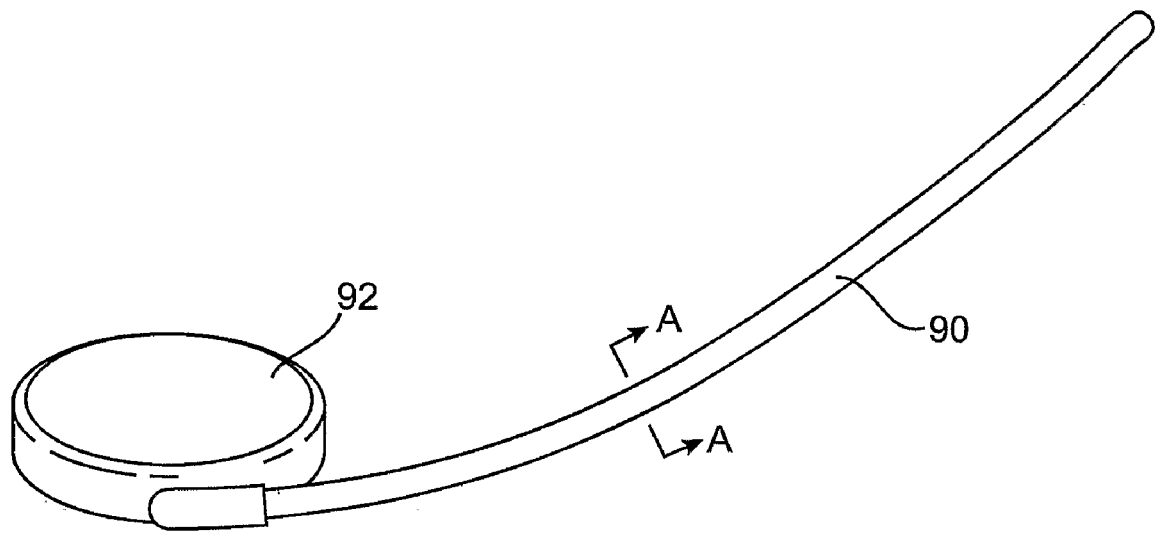
FIGS. 21A and 21B provide a view of an optical strain gauge device according to an embodiment of the invention.
Figure 21B:
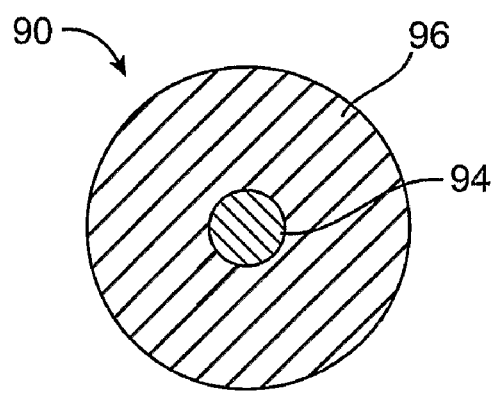

FIGS. 21A and 21B provides a view of an embodiment of the present cardiac timing device as a guide wire location, with particular application to optical strain gauge use. This embodiment provides special opportunities for installation of the inventive device. In FIG. 21A, a very narrow diameter wire is instrumented in the manner of the present invention. The device is positioned in a typical guide wire location in the cardiac vein. This application is particularly appropriate for small sensors, such as fiber optic strain sensors.

Device installation is accomplished using a standard lead standard guide wire. After installation is completed, the standard lead guide wire may be withdrawn and replaced with a guide wire instrumented with strain gauges of a variety of types, augmented as appropriate with other sensors.

In an additional embodiment, a guide wire that is already instrumented is used to cannulate the coronary sinus and the cardiac vein. The lead is then slipped over that guide wire, a typical current approach for other procedures, and left in place. The guide wire thus positioned is available to acutely re-synchronize the heart in the initial catheter. It can then be withdrawn or left in the heart for a long period of time as an implant. In the latter case, the device is available for and re-synchronize the heart for years afterward. The design described above could be used for both acute or long term use.

FIG. 21A is a schematic drawing of lead 90 that runs from the pacemaker can 92. In the cross sectional view along lines A-A of the lead 90 is shown the location of the guide wire 94 which is typically situated at the center of the lead body 96, as shown in FIG. 21B. The location of the guide wire 94 is normally in the center of the lead 90. However, in embodiments not illustrated, guide wire 94 is positioned off-center, or in many potential locations within the circumference of lead 90.

For the purposes of measuring the bending of the axis of lead 90, it is not critical that the sensors be centered or off-axis, so long as the sensing element is measuring bending forces and not stretching forces. If the sensing element is measuring stretching, being at the center of lead 90, it is a potential disadvantageous design. The confounding factor is that the center line typically does not stretch unless the ends are pinned and, as a result, change the radius of curvature. An important consideration in such designs is that if guide wire 94 slides within the lead, it will not stretch. If guide wire 94 is pinned at the ends, it will undergo a stretching force between the places where it is pinned. These approaches represent an improvement upon the basic initial design of a guide wire that does slide within a lead. An additional design embodiment is to crimp or otherwise restrain the guide wire 94 within lead 90 after it is installed in order to generate a stress within the guide wire 94.

Figure 22A:
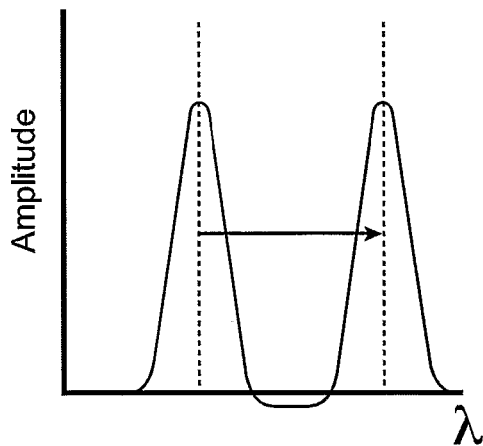
FIGS. 22A to 22C provide another view of the device depicted in FIGS. 21A and B, as well as signals that might be obtained from the strain gauge sensor elements of the devices, FIGS. 23A to C and 24 provide various views of optical strain gauge embodiments of the invention and results obtainable therewith.
Figure 22B:
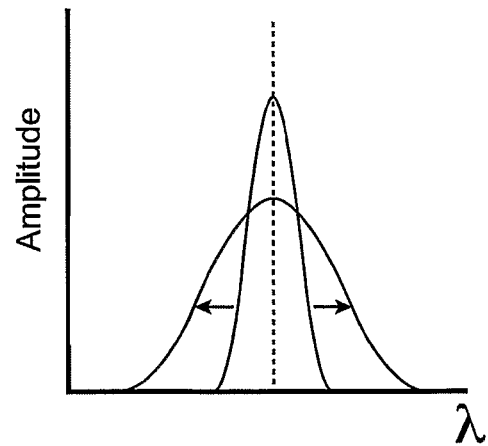
Figure 22C:
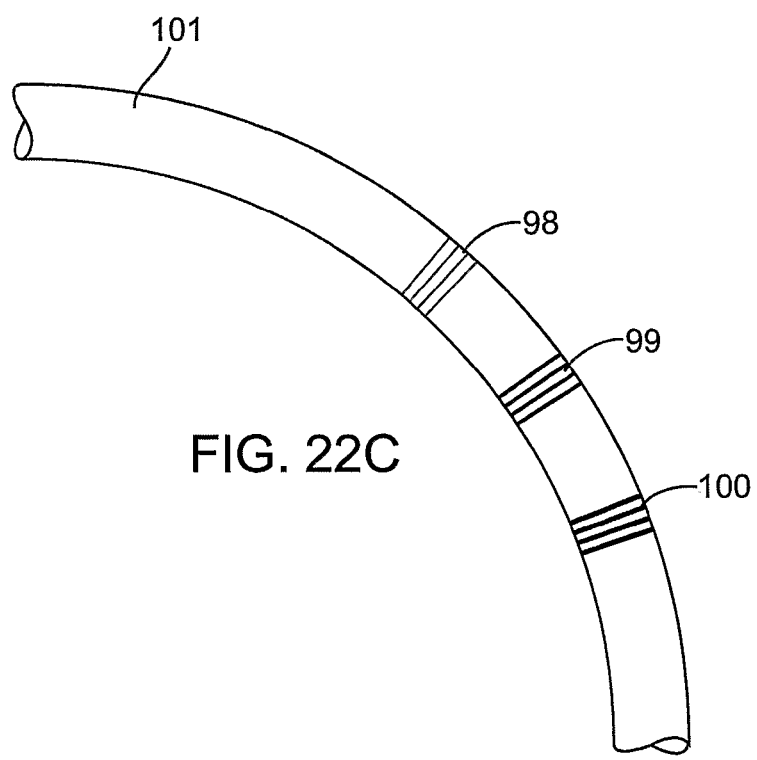

FIG. 22C provides a view of optical strain sensors 98 to 100 associated with a cardiac lead 90 that is of a dimension appropriate for installation in the cardiac vein. The sensors can be located inside of guide wire 94, located inside lead 90, or next to lead 90. Strain sensors 98-100 can be selected from fiber optic strain or bending sensors, where multiple embodiments are available. One embodiment of optical strain sensors 98-100 is birefringent fibers. The characteristics and sensing capability of birefringent fibers are well-known to the ordinary skilled artisan. See e.g., Young, *Fundamentals of Waves, Optics, and Modern Physics*, McGraw-Hill, New York, N.Y., 1976, pp 107-110.

In the inventive embodiment employing optical sensors shown in FIG. 22C, the optical strain sensors 98-100 are composed of one complete fiber 101 that is provided with a mirror surface at the end, not illustrated in this view, through polishing or with a metal overlay. Light passes from the pacemaker can 92 through the length of the fiber 101, returning to pacemaker can 92 with cardiac timing data. When a polarized light is used, the polarization of the light rotates as is goes through the birefringent areas of the fiber 101. In some configurations, it is advantageous to provide an optical element at the end of the fiber 101 in order to accomplish an appropriate phase shift of the light. In other design configurations, various types of phase shifters and polarization filters are provided at the entrance of the fiber.

If birefringent fiber is employed for fiber 101 in the entire length of lead 90, the birefringent fiber is sensitive to bending forces throughout its length. In this configuration, bending anywhere along lead 90 is measured and reported, potentially confounding the desired data signal. Therefore, in some inventive configurations, it is advantageous to employ an optical fiber that is made of two parts. In the two-part optical fiber configuration of the inventive cardiac timing device, the first part is constructed of a coupling fiber that is not sensitive to bending in any way. The second section of the optical fiber is constructed of a birefringent fiber. While there will be, at times, some reflections at that interface between the coupling fiber and the birefringent fiber of this construct, these reflections can be filtered out by means well know to the skilled artisan.

The cardiac timing data is converted through the signal received from the optical sensor device. The light passes through the birefringent fiber, and returns through the same fiber. In this way only the region of the fiber that is birefringent is sensitive to bending in that area, and can provide clear data regarding the cardiac features to which it is adjacent.

In another embodiment of the inventing cardiac timing device, a single optical fiber is a starting material. By preferentially doping certain segments of that single fiber, characteristics are selectively changed to produce birefringence. An important benefit of this fabrication approach is reflection, which can occur when two fibers are welded together.

For some applications, the above fabrication approach produces a cardiac timing device which provides measurement of bending at different locations within lead 90, allowing data generation from discreet cardiac features, and areas on those features. In an additional iteration, multiple fibers are provided, each with a birefringent region. These fibers are then bundled together. In this configuration, each of the fibers measures the bending at a different location down the length of the lead 90.

In another inventive cardiac timing device configuration that allows the measurement of bending, stressor strain is detected in a fiber by the use of fiber Bragg gratings as strain gauge features. In this implementation of the present invention, the fiber is selected from those that, when exposed to an intense amount of light, and chosen for that fiber, will change its index of refraction. During fabrication, if a mask is used that has lines in a certain pitch to expose alternating regions of that fiber, a sequence of regions that are varying in the index of refraction is created. This is called a fiber Bragg grating (FBG).

In practice, a protective material is provided for one length of fiber, all with the same pitch. Once the mask fabrication has been accomplished, the fiber reflects colors that have a wavelength related to that pitch and determined by the index of refraction of the exposed region and the unexposed region. While somewhat complex, a well known formula describes this phenomena, and would be employed to select the preferred wave length reflectance for this application.

Measuring strain with a fiber Bragg grating derives from the characteristic of such fibers that, if they are stretched or bent, the pitch of the grating will change. If the fiber is stretched, the pitch becomes longer, which changes the wavelength directly. If the fiber is bent, then some areas of the fiber get a little longer and some areas get a little narrower. In this manner, forces on the fiber tend to change the reflectivity at a given wavelength, and broaden the reflective signal.

Using the above approach, linear strain is measured by ascertaining a shift in the reflective wavelength. Typically, the band width of the reflected light will not change and the center frequency shifts with linear strain. In this manner, the inventive cardiac timing device measures bending at the same time by looking at the changes in the width of the reflected signal. In the case of pure bending, center frequency does not shift, but the bandwidth increases. At a lower frequency, some wavelengths at a lower wavelength would be reflected and some wavelengths at a higher wavelength would be reflected. The amplitude at the center frequency would be reduced.

In this embodiment, a broader signal is provided. Bending is measured by the width at half height. FIG. 22A shows a graphic demonstration of that wavelength of the reflected light. In the case where white light is sent down fiber 101, only those wavelengths that correspond to that encoded by the fiber Bragg grating in pressure sensor positions 98, 99 and 100, are reflected and amplified. The remaining wavelengths are eliminated by a device at the end of the fiber. This device prevents reflection of any other wavelengths. The reflected light that comes back to the can 92 is a function of the wavelengths that are coded in the various fiber Bragg gratings. In this example, the fiber Bragg gratings in position 98 correspond to green wavelengths, position 99 correspond to blue wavelengths, and 100 correspond to red wavelengths.

If fiber 101 stretches, the wavelength that is reflected shifts because the pitch of the various fiber Bragg gratings changes. If the fiber 101 bends, the width in wavelength terms of the reflected light reflected broadens. This phenomena is shown in FIG. 22B, which shows the effect of fiber 101 being bent. Some light at different frequencies and/or different wavelengths are reflected back due to the variation in the period over the diameter of the fiber optic. As a result, there are two independent measurements, one measuring linear strain and the other measuring bending.

By providing different grading periodicities in the inventive cardiac timing device, different wavelengths are caused to be reflected at different locations on fiber 101. Those locations are sensitive to bending or stretching. This configuration allows the use of a single fiber to measure the strain or bending at various locations along the fiber's length. In practice, a light generator is provided with the capacity to send out appropriate inquiring light signals, and other features are also provided to accomplish excitation and signal recovery through circuitry.

Figure 23A:
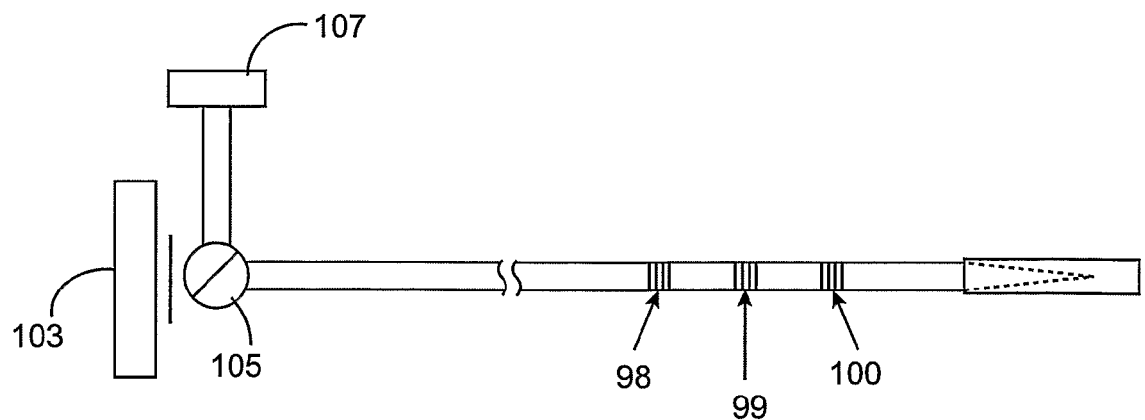

FIG. 23A shows one embodiment of the excitation and detection systems for such a multiple fiber Bragg grating strain bending sensor system. Shown on the left of FIG. 23A is a vertical cavity surface emitting laser (VCSEL) 103. VCSEL 103 can be of a basic design to those VCSELs which are typically used in the telecommunication industry to generate light of varying wavelengths. A controlling chip (not shown) is provided which sends appropriate signals to VCSEL 103 to generate a very short or brief pulse of light at a wavelength. VCSEL 103 would then emit the pre-designated light, which then proceeds into beam splitter 105.

Beam splitter 105 functions to modify the light beam so that much of the light goes through the fiber optic. When this is accomplished in the region, light is sent in the region of one of the fiber Bragg grating positions 98, 99 and 100. Thus, in position 99 where blue is being queried, wavelengths are sent at a little bit less and a little bit more than blue. The returning light is then measured while the emitted light is scanned for the light through the blue region. A similar approach is used in some cases for infra-red region for example. Various other common color communication types of wavelength are also used.

The light reflected from the fiber Bragg grating returns to beam splitter 105. The beam splitter 105 functions to return half of the light to a pin detector, 107. Pin detectors are standard devices in the telecommunications industry. In the case, the pin detector measures the amplitude of the reflected light. VCSEL 103 generates light of different wavelengths which are sent as pulses down the fiber optic. Some of this light is reflected back by the various fiber Bragg gratings at positions 98, 99 and 100. The amplitude of these light signals is recorded on pin detector 107.

Figure 23B:
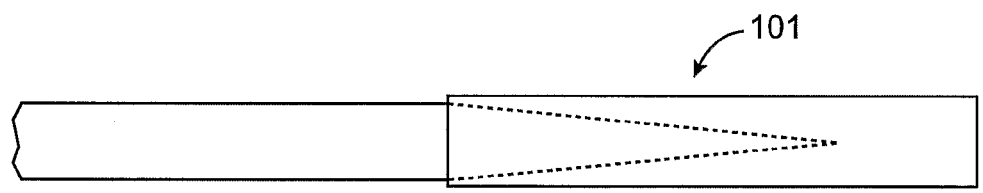
Figure 23C:
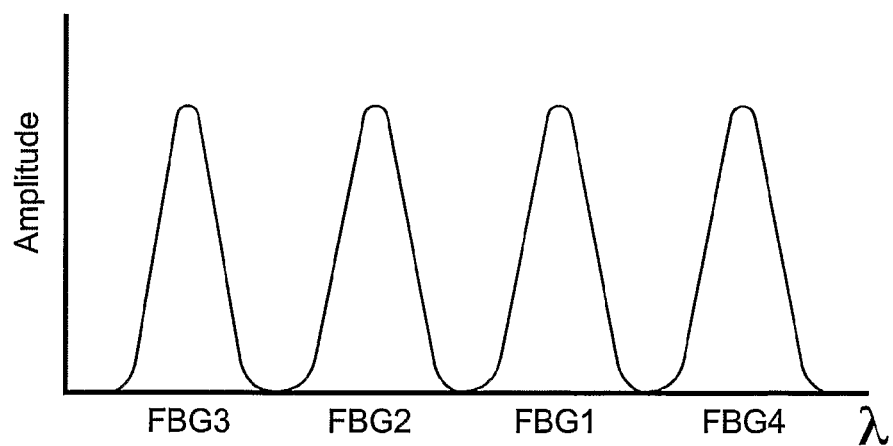

The data thus generated by the inventive cardiac timing device provides, essentially, a drawing as in FIG. 23C, which shows the amplitude at various wavelengths of light. Each of the reflected wavelengths correspond to a different fiber Bragg grating. In FIG. 23C, the first peak corresponds to the reflections in fiber Bragg grating 3, the second peak corresponds to fiber Bragg grating 2, the third peak corresponds fiber Bragg grating 1, the fourth peak, fiber Bragg grating 4. The order of the various peaks may not correspond to the order of the fiber Bragg grating positions 98, 99 and 100 because the order, or location, where these fiber Bragg gratings are along the fiber is not critical to obtaining data; the light signals will be reflected regardless of where they are located. The amplitudes and widths of these reflected signal are then used to determine the strain at that location of the fiber.

FIG. 23B shows a schematic of the end of optical fiber 101, specifically showing that the cladding of the fiber 101 is progressively removed. In this manner, more and more of the energy is dissipated into the surrounding, ambient environment. There are a number of means to defeat the reflectance of a fiber optic cable. These are well known in the industry, and can be selected to optimally defeat the fiber's reflectance. Proper selection of this means essentially destroys the reflection of all of the unwanted frequencies, i.e., those frequencies not reflected by the fiber Bragg grating. Alternatively, one can select a means that attenuates the reflection so much that these reflections do not affect the quality of the signal significantly.

Figure 24:
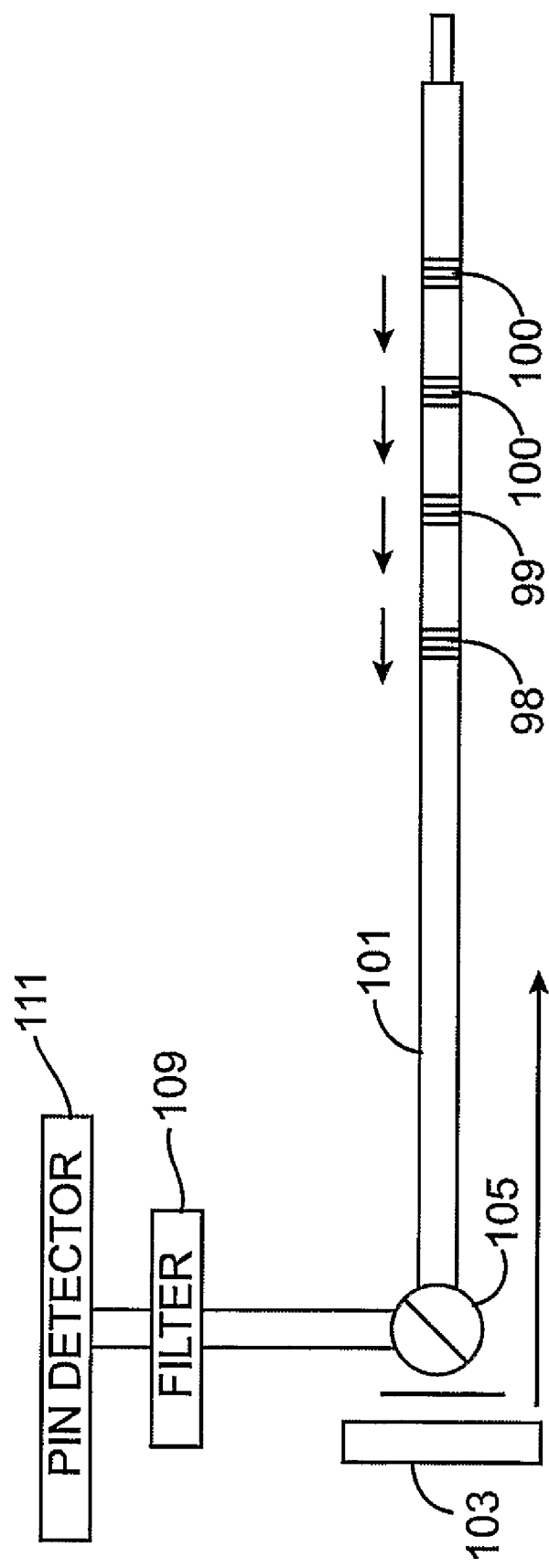

FIG. 24 shows another embodiment of the present cardiac timing device. This embodiment can accomplish the same function as the above device, but with a different design. In this case, the reflectivity at different amplitudes of light going down the fiber optic encodes for strain or bending. In this configuration, a white light or a broad band light generator is used to broadcast light into beam splitter 105 that is coupled into the fiber 101. This white light is transmitted down the length of the fiber 101 as white light. Only those colors that are encoded by the fiber Bragg gratings at positions 98, 99 and 100, as determined by fiber 101 state of stress and bending are reflected. The other wavelengths are dissipated at the end of fiber 101. All of those reflected lights return, going through the beam splitter 105. Part of that light is then sent down the perpendicular pathway to the filters 109. These filters 109 are optical filters which allow only narrow bandwidths of light to pass through.

In some iterations of this embodiment of the inventive cardiac timing device, MEMS filter 109, such as a Fabry-Perot cavity, are provided where the distance between plates is modulated to select for a given wavelength of light. This programmable filter 109 is then scanned over the wavelengths of interest. The light flows through programmable optical filter 109, and impinges upon a diode detector 111 which measures how much amplitude returns. In this case, a broadband light source 103 and a programmable light filter 109 checks how much reflection is at each of the wavelengths.

In both cases, these different designs produce a system such as shown schematically in FIG. 23C. These systems provide the amplitude at various wavelengths and the shape and amplitude of those peaks determines the stress and bending of the device, of the lead 90.

Figure 33A:
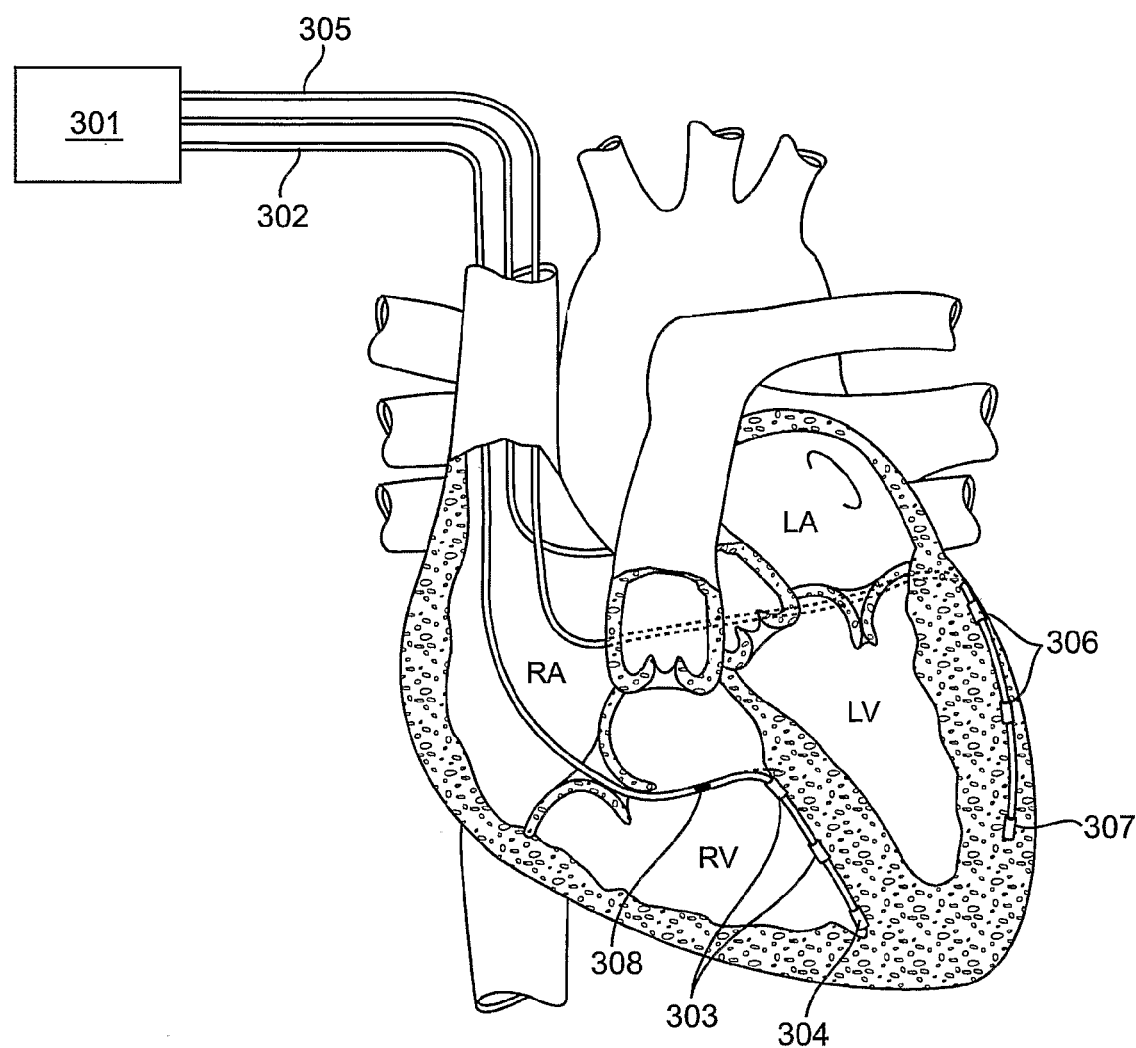
FIG. 33A illustrates the location of a number of fiberoptic strain gauges in accordance with an embodiment of the present invention.

One embodiment of the present invention provides a cardiac motion detection system which includes a number of fiberoptic strain gauges coupled with each other through a single optical fiber. FIG. 33A illustrates the location of a number of fiberoptic strain gauges in accordance with an embodiment of the present invention. As shown in this example, communication means 301 provides the extracardiac communication and calculation means for the overall system. In more complex configurations, communication means 301 may provide a means for communicating data and light source from a completely external or extracorporeal location.

Right ventricular lead 302 emerges from communication device in communication means 301, and travels from the preferentially subcutaneous location of communication means 301 via the subclavian venous access through the superior vena cava through the right atrium and then through the tricuspid valve to a position along the right ventricle. This location is preferentially located along its distal portion in close association with the intraventricular septum terminating distally with fixation in the right ventricular apex.

Particular to distal aspect of right ventricular lead 302 are fiberoptic strain gauges 303 and 304. In other embodiments of the present invention, an additional number or smaller number of fiberoptic strain gauges may be employed.

Additionally emerging at the proximal aspect of communication means 301 is left ventricular lead 305. Left ventricular lead 305 starts by following the same route as right ventricular lead 302 via subclavian vein through the superior vena cava into the right atrium. At this point, left ventricular lead 305 is placed via the coronary sinus around the posterior aspect of the heart and thence into cardiac vein draining into said sinus.

FIG. 33A further depicts left ventricular lead 305 in a position likely to be advantageous for biventricular pacing located along the lateral aspect of the left ventricle. Fiberoptic strain gauges 306 and 307 in the left ventricular are analogous to gauges 303 and 304 which are previously described.

Right ventricular lead 302 may optionally be provided with pressure sensor 308 which is located in the right ventricle. Pressure sensor 308 provides a pressure signal which can also simultaneously be obtained with wall motion data. Note that adding active devices to said lead such as pressure sensor 308 is facilitated through the use of a multiplexing system Principle of operation of fiberoptic strain gauges 303, 304, 306, and 307 is that communication means 301 will communicate with each of the sensors. Cardiac movement signals detected by each gauge are then timed.

Figure 33B:
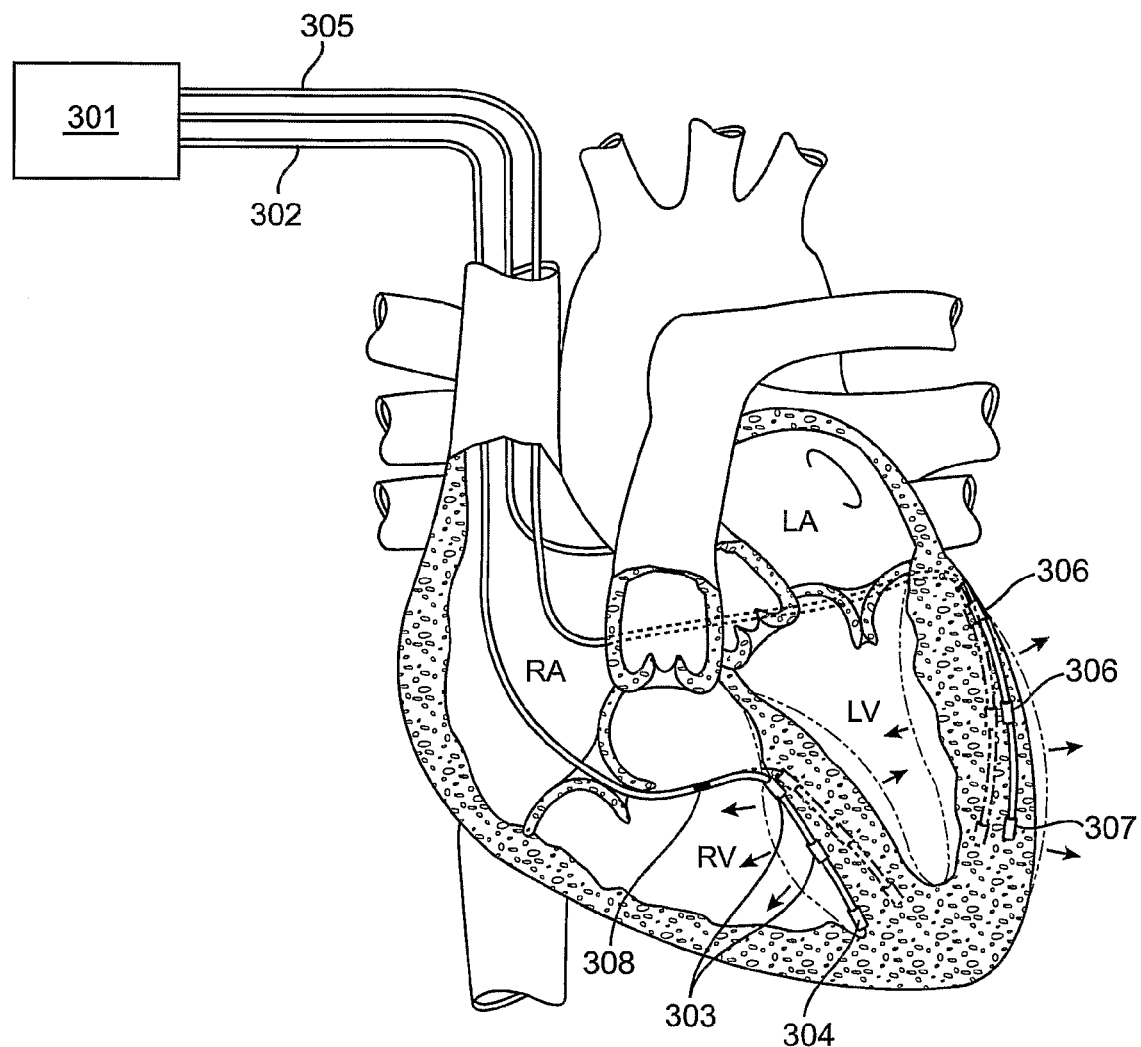
FIG. 33B illustrates the location of a number of fiberoptic strain gauges showing additionally the cardiac motion in accordance with an embodiment of the present invention.

FIG. 33B illustrates the location of a number of fiberoptic strain gauges showing additionally the cardiac motion in accordance with an embodiment of the present invention. As shown in FIG. 33B, right ventricular lead 302 and left ventricular lead 305 are provided in close association with the wall of the heart. As the wall of the heart moves via 3D cardiac cycle, so do the catheters in a proportionate amount. As these catheters bend at certain locations with the cardiac contractions, the fiberoptic strain gauges detect the corresponding motion and position of the tissue at question which vary over the course of the cardiac cycle. This variation is indicative of their movement and the timing thereof.

The cardiac motion data together with an optional pressure signal or signals is used to optimize cardiac resynchronization therapy where the goal is to maximize the contractility of the left ventricle. This goal is obtained by encouraging effectively simultaneous contraction of the bulk of the muscle of the left ventricle. In many congestive heart failure patients, such contractility is impaired with dyskinetic contraction, which typically occurs with a septal contraction against a relaxed left ventricle followed by ventricular contraction against a relaxing septum. The result is inefficiency with regards to the blood being moved around the ventricle rather than constrictively expelled from the ventricle as in a normal case.

Current systems provide biventricular pacing on an empiric basis only where optimization is attempted. It is generally a time-consuming process based on external cardiac ultrasound. A physician typically attempts to visualize wall motion. Conventionally, with the aid of tools in an ultrasonic machine, the physician calculates a synchronicity index based on the wall motion just described. In contrast, the present cardiac motion detection system provides such data in real time and in a numeric format useable by both the implanting physician and by an automated pacing system such as a CRT device.

A fiberoptic strain gauge provided in one embodiment of the present invention detects abnormalities in wall motion associated with ischemia or arrhythmia and other cardiac abnormalities including progression of underlying disease states such as congestive heart failure. If connected to an external or fully implanted real time monitor, such abnormalities can trigger an alarm. This alarm alerts the patient or a physician of the advent of these abnormalities.

Figure 33C:
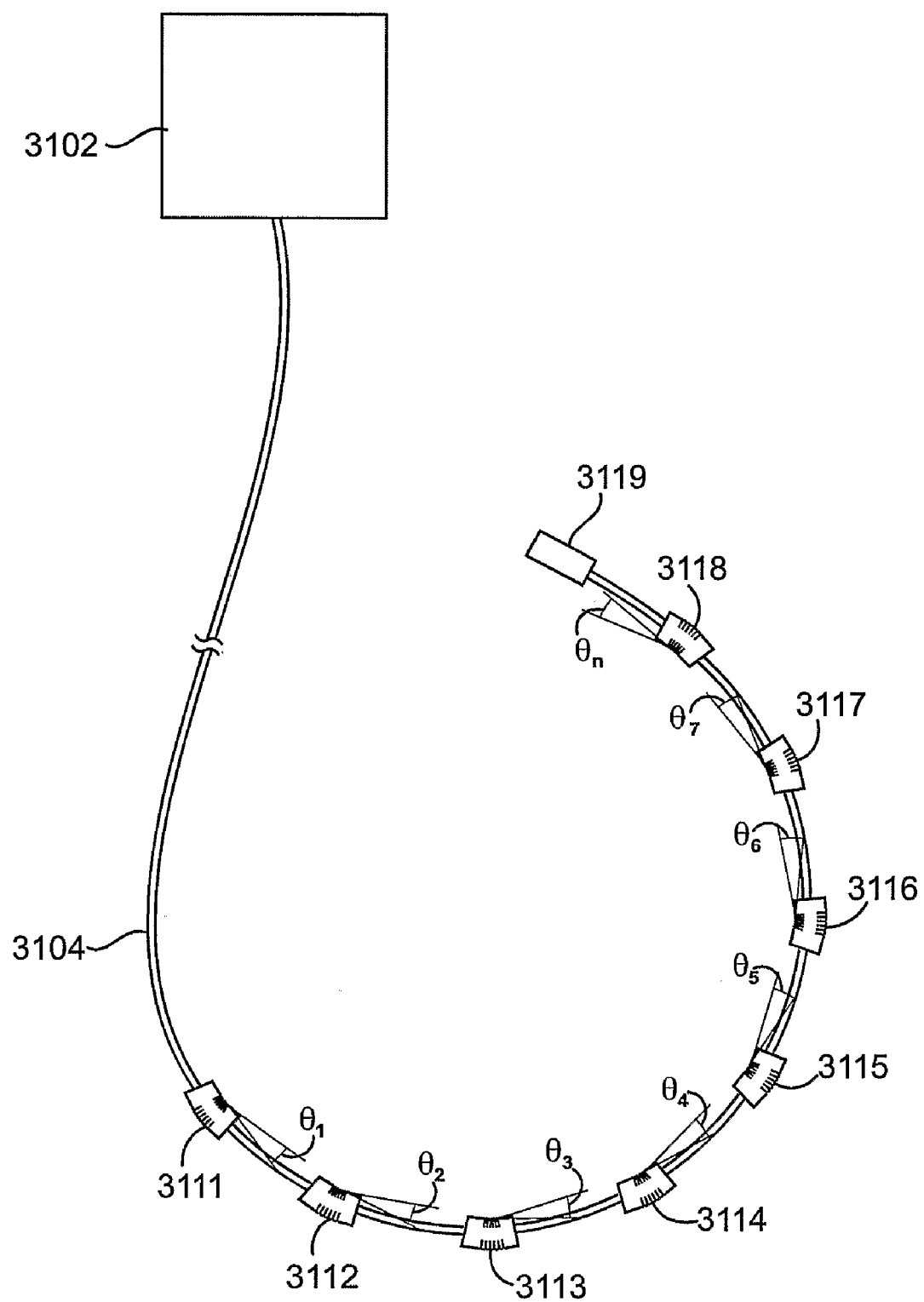
FIG. 33C illustrates an exemplary configuration of a cardiac motion detection system involving a number of fiberoptic strain gauges in accordance with an embodiment of the present invention.

FIG. 33C illustrates an exemplary configuration of a cardiac motion detection system involving a number of fiberoptic strain gauges in accordance with an embodiment of the present invention. In one embodiment of the present invention, a control module 3102 is coupled to a main optical fiber 3104. Control module 3102 transmits light signals into optical fiber 3104, which is coupled to a number of fiberoptic strain gauges 3111-118. As explained in later sections, each fiberoptic strain gauge is constructed using a MEMS-based structure which couples two pieces of optical fibers, namely an input fiber and a reflection/pass-through fiber.

When a fiberoptic strain gauge is in a normal, unbent state, the light signals entering the input fiber of the strain gauge are transmitted and coupled into the reflection/pass-though fiber. The reflection/pass-through fiber contains a fiber Bragg grating, which reflects light signals at a given wavelength (i.e., the Bragg wavelength) back to the input fiber and allows light signals at other wavelengths to pass through. When the strain gauge is bent, the amount of reflected light at the Bragg wavelength varies. In addition, the amount of pass-through light also varies due to the coupling loss. In this way, by transmitting a number of wavelengths into fiber 3104, and by detecting the amount of reflected light at different Bragg wavelengths corresponding to each strain gauge, control module 3102 can determine the amount of bending incurred at each strain gauge. Furthermore, control module 3102 can monitor the timing of cardiac contractions based on the timing of variations of the reflected light. Note that the system illustrated in FIG. 33C may optionally include an attenuator 3119 at the end of fiber 3104 to reduce the amount of reflected light.

In representative embodiments, the strain gauges include fiber Bragg gratins, as indicated above. Fiber Bragg gratings can be manufactured in a number of ways. One type of fiber Bragg gratings contain gratings external to the core, which are placed in the cladding as described in the article "A single mode fiber evanescent grating reflector" by Sorin and Shaw in *IEEE Journal of Lightwave Technology*, vol. 3, pp. 1041-1045 (1985), and in U.S. patents by Schmadel (U.S. Pat. No. 4,268,116, issued May 19, 1981), Ishikawa (U.S. Pat. No. 4,622,663, issued Nov. 11, 1986), and by Sorin (U.S. Pat. No. 4,986,624, issued Jan. 22, 1991). These designs involve periodic gratings which operate in the evanescent field within the cladding layer proximal to the core of the fiber.

A second class of fiber gratings involves internal gratings fabricated within the core. One technique involves modulating the core refractive index. In-core fiber gratings were disclosed by Hill et al. in "Photosensitivity in optical fiber waveguides: Application to reflected filter fabrication" in *Applied Physics Letters*, vol. 32, pp. 647-649 (1978). These gratings are written internally by interfering two counter propagating electromagnetic waves within the fiber core, one of which is produced from the reflection of the other from the fiber end face. Meltz et al. further showed how to write gratings externally by the split-interferometer method involving side-illumination of the fiber core by two interfering beams produced by a laser, as described in "Formation of Bragg gratings in optical fibers by a transverse holographic method" in *Optics Letters*, vol. 14, pp. 823-825 (1989).

If the refractive index within the fiber grating's core is plotted as a function of distance that is measured along the core's length, the resulting curve would have a periodic variation. Correspondingly, the core has a nominal or average index of refraction, and the core's actual refractive index varies from this average value.

Mathematically, the Bragg wavelength $\lambda_B$ of a fiber grating is described as:

$$\lambda_B = 2 \cdot P \cdot n$$

where P is the grating period and n is the nominal or average refractive index of the core.

As shown by the above equation, the Bragg wavelength $\lambda_B$ of a fiber grating is shifted by a change in the grating period P, and/or by a change in the average refractive index n of the core. In general, the grating period and the average index of refraction change when the fiber grating is subjected to a change in strain (e.g., the fiber grating is stretched lengthwise), a change in length that is caused by a temperature change, or to a change in length that is caused by pressure, all of which can be collectively defined as photoelastic and thermo-optic effects.

Both the peak reflectivity and the spectral bandwidth of reflected light at a Bragg wavelength are functions of the fiber grating's length and the amount of refractive index variation that is present at each periodic index variation. Conventionally, as a result of these above properties, a fiber grating can be used as a strain sensor, a temperature sensor, and a pressure sensor. In each case, the strain, temperature, and/or pressure is measured by determining a shift in the fiber grating's Bragg wavelength from a calibration point, or by measuring the absolute value of the Bragg wavelength.

Figure 34A:
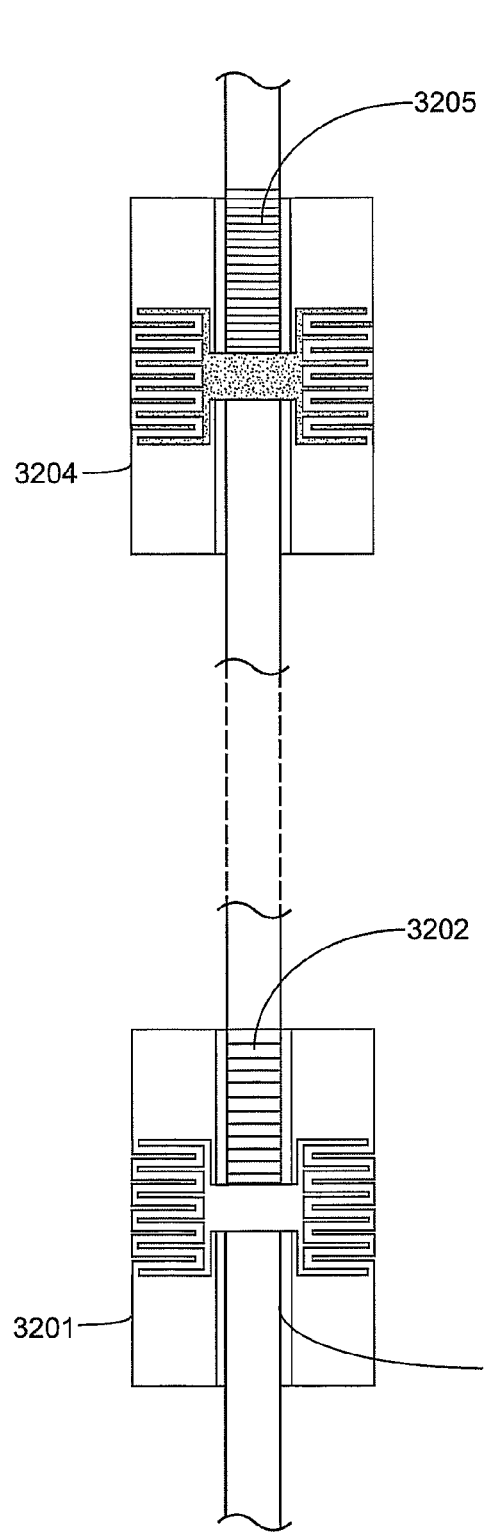
FIG. 34A illustrates an exemplary cardiac motion detection system including two fiber Bragg gratings coupled to a main optical fiber with two MEMS folded spring structures in accordance with an embodiment of the present invention.

The fiberoptic strain gauge provided in one embodiment of the present invention detects strain or bending imposed upon the gauge based on the amount of light reflected by a fiber Bragg grating, instead of the shift of Bragg wavelength. This design significantly increases the sensitivity and dynamic range of the strain gauge. FIG. 34A illustrates an exemplary cardiac motion detection system including two fiber Bragg gratings coupled to a main optical fiber with two MEMS folded spring structures in accordance with an embodiment of the present invention.

As shown in FIG. 34A, a MEMS folded spring structure 3201 couples an input fiber 3203 to a fiber Bragg grating 3202. When the strain gauge is in its regular, unbent position, input fiber 3203 is aligned with grating 3202. As a result, when a light beam is transmitted into fiber 3203, a significant amount of light at grating 3202's Bragg wavelength is reflected back to input fiber 3203. However, other wavelength components of the input light can pass through grating 3202 with much less reflection.

MEMS folded spring structure 3201 maintains a gap between fiber 3203 and grating 3202. Because of the flexibility of the folded springs, the strain gauge enjoys certain degree of freedom when there is a lateral strain. When such a lateral strain is present, the alignment between fiber 3203 and grating 3202 is disturbed. Consequently, the amount of reflected light at grating 3202's Bragg wavelength is reduced. Therefore, by detecting the amount of reflected light at grating 3202's Bragg wavelength, the system can easily determine when the strain gauge is bent. Furthermore, the system can also determine the amount of bending based on the coupling loss. Note that because the bending also increases the coupling loss of light at other wavelengths, the amount of pass-through light is reduced when the strain gauge is bent. One advantage of this strain gauge design is that, unlike previous designs which require detection of optical signals at an output fiber, the detection of reflected signals occurs at the input fiber. This one-port operation significantly reduces the complexity of the cardiac motion detection system. In addition, because there is no looped double-fiber configuration, the entire system can be constructed with a considerably reduced form factor.

Also shown in FIG. 34A shows a second strain gauge which includes a MEMS folded spring structure 3204 and a fiber grating 3205. This second strain gauge takes the fiber which contains grating 3202 as its input fiber. Grating 3205 has a Bragg wavelength different from that of grating 3202 and reflects a different wavelength. Hence, by detecting the amount of reflected light at the two Bragg wavelengths which correspond to gratings 3202 and 3203 respectively, the system can tell how much bending each strain gauge is subject to.

Figure 34B:
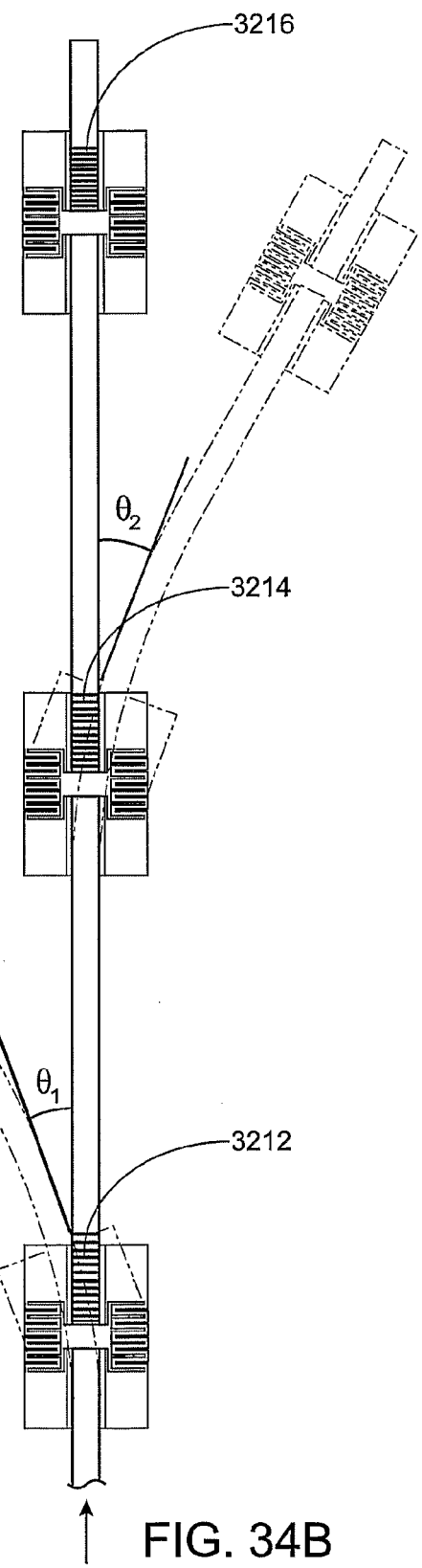
FIG. 34B illustrates an exemplary mode of operation of the cardiac motion detection system in accordance with an embodiment of the present invention.

FIG. 34B illustrates an exemplary mode of operation of the cardiac motion detection system in accordance with an embodiment of the present invention. In this example, three fiberoptic strain gauges, containing gratings 3212, 3214, and 3216, respectively, operate jointly. Each grating has a different Bragg wavelength. Also shown in dashed lines are potential bending positions for the first and second strain gauges. When the first strain gauge is bent at an angle $\theta_1$, there is a misalignment between the input fiber and grating 3212. Consequently, the amount of reflected light at grating 3212's Bragg wavelength is reduced. Similarly, when the second strain gauge is bent at an angle $\theta_2$, there is a misalignment between the input fiber and grating 3214, and the amount of reflected light at grating 3214's Bragg wavelength is reduced.

Note that when an upstream strain gauge is bent, the pass-through light coupled to the downstream strain gauges suffers from the coupling loss caused by the bend at the upstream gauge. When light is reflected by a downstream strain gauge, the reflected light must go through the same upstream gauge and hence experience once again the coupling loss. These coupling losses dictate that the absolute amount of loss of reflected light at different Bragg wavelengths may not be equal.

However, the absolute amount of losses at different Bragg wavelengths is of less significance to the present cardiac motion detection system. The present system detects cardiac motions based on the relative variation of losses at each Bragg wavelength instead of the absolute values of these losses. Hence, as long as the system uses detectors with a sufficiently large dynamic range, the bending of different strain gauges can be successfully detected. In one embodiment, the dynamic range of a detector used by the system is larger than about 30 dB, such as larger than about 50 dB, including larger than about 70 dB.

An alternative approach to reduce the cumulative coupling losses experienced by different strain gauges and to accommodate detectors with smaller dynamic range is to adjust the power of the input light at each Bragg wavelength. For example, the power of the input light at the Bragg wavelength corresponding to the most upstream strain gauge can be set at the lowest level, while the power of the input light at Bragg wavelengths corresponding to down stream strain gauges can be set at progressively higher levels. In this way, detectors with smaller dynamic range can still detect loss variations for all the Bragg wavelengths. Note that this configuration would require individual power adjustments at different wavelengths. A broadband light source typically does not provide such individual power adjustability at specific wavelengths.

In most cases, it is beneficial to minimize the unnecessary coupling and reflection losses between the input fiber and the Bragg grating fiber. Excessive coupling loss occurs when a light beam exiting the input fiber diverges quickly due to the refractive index difference between the fiber core and the air. Such quick divergence prevents efficient coupling of light into the core of the reflection/pass-through fiber. Moreover, the fiber-air index difference also causes light to reflect back at a fiber's end face. A reduction of such losses helps improve the sensitivity of the strain gauge. One approach to reduce these unnecessary losses is to fill the gap between two fibers with an index-matching material, such as a polymer. Ideally, the index of this material matches the index of the fiber core.

Figure 34C:
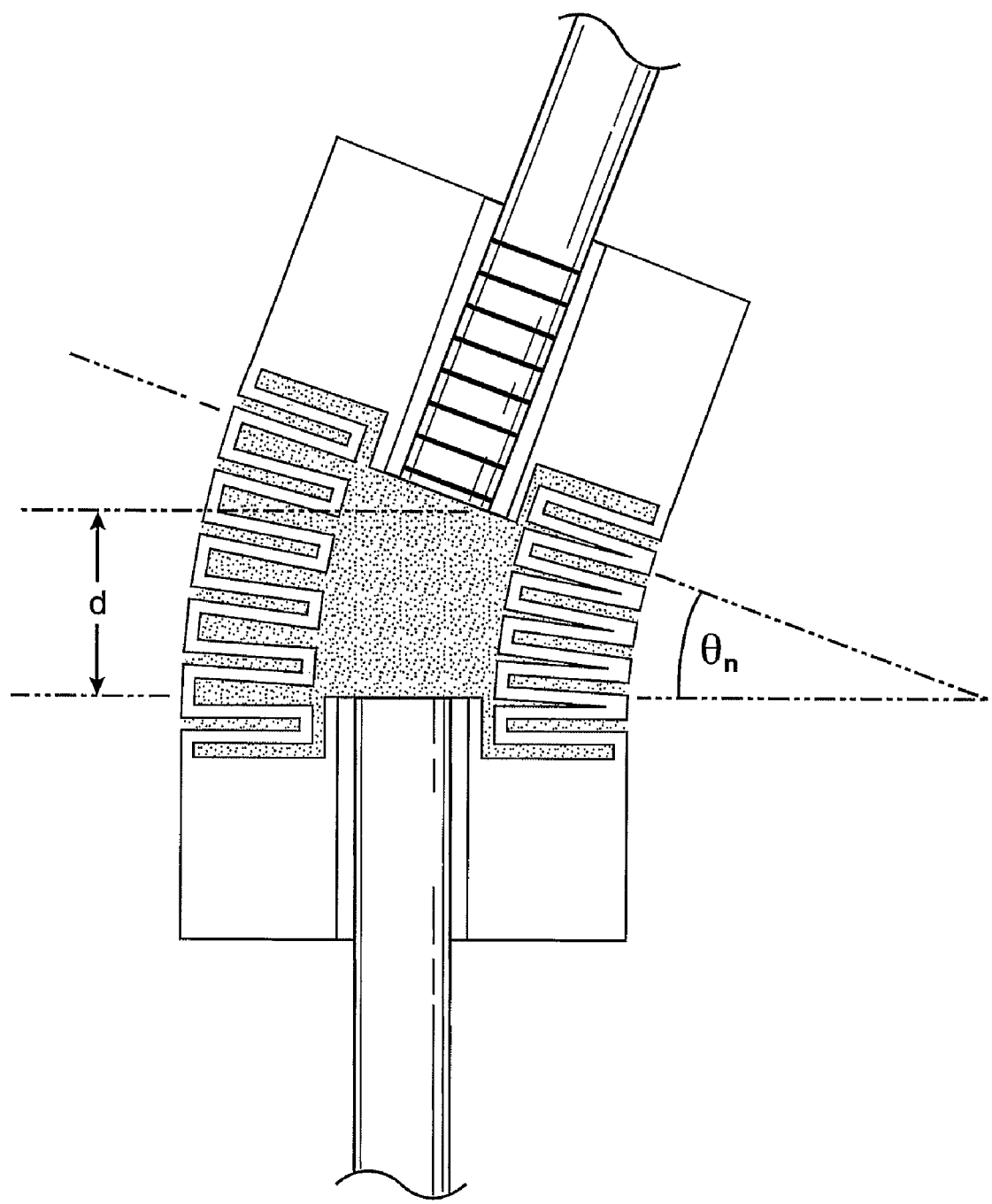
FIG. 34C illustrates a fiberoptic strain gauge containing index-matching material in accordance with an embodiment of the present invention.

FIG. 34C illustrates a fiberoptic strain gauge containing index-matching material in accordance with an embodiment of the present invention. As shown in FIG. 34C, the strain gauge is bent at an angel $\theta_n$, and the gap between the input fiber and the reflection/pass-through fiber is of distance d. An index-matching material, such as a polymer, is used to fill the gap. The use of index-matching material helps mitigate the light divergence and hence reduces the coupling loss between the two fibers. Furthermore, excessive reflection loss at a fiber end face is reduced when the gap is filled with index-matching polymer. Note that the index-matching material can be in the form of gel or fluid.

Ideally, the range of bending of a strain gauge is sufficiently large so that a loss caused by cardiac motion can be detected. At the same time, the bending of a gauge is limited so that the gauge is not over-bent and that the light is not completely lost for downstream strain gauges. The range of bending can be controlled through the catheter in which the strain gauge resides, or through controlling the stiffness of the MEMS folded spring structure.

Figure 34D:
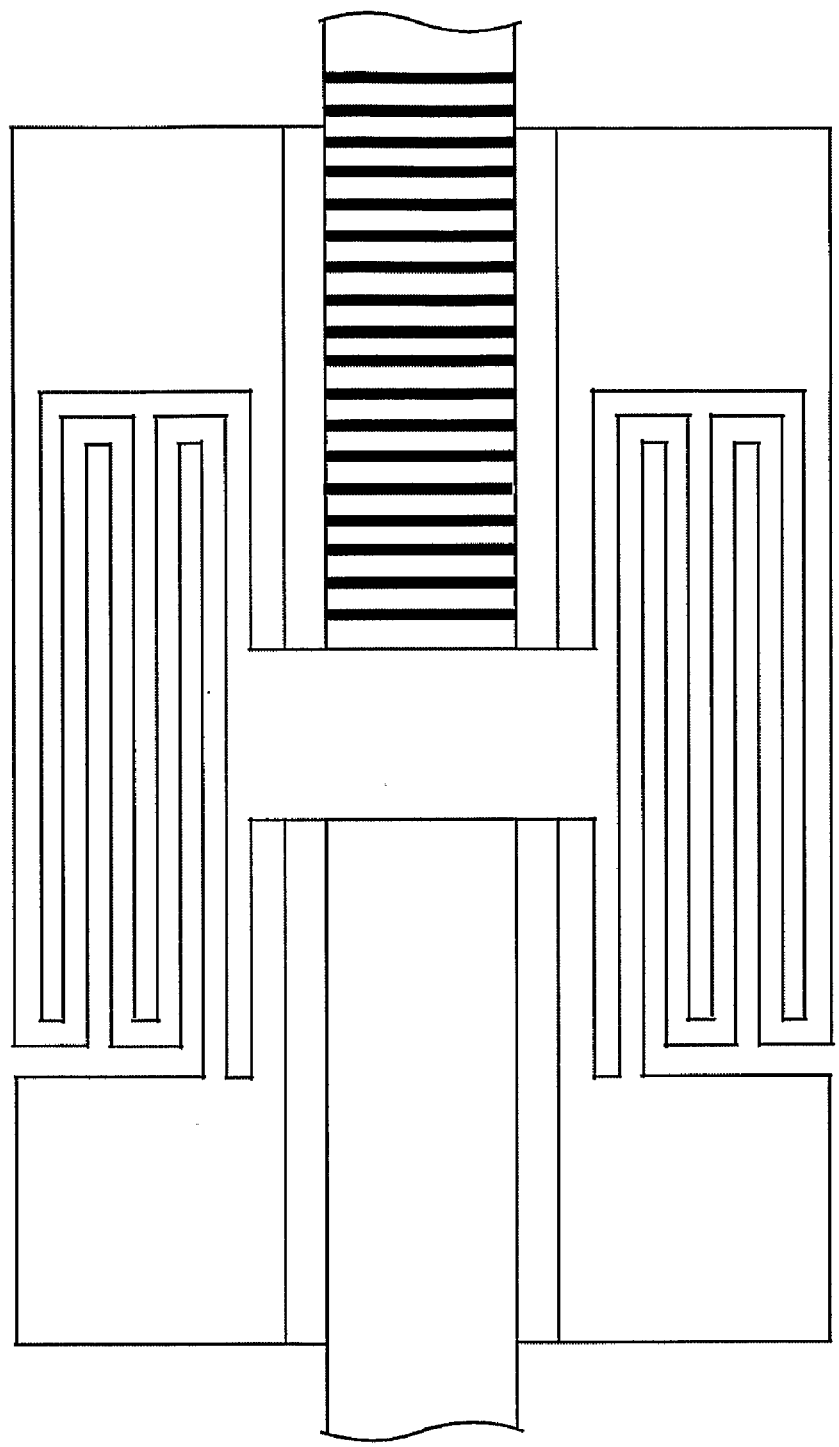
FIG. 34D illustrates an exemplary design of MEMS folded spring structure wherein the torsion beams are parallel to the optical fibers in accordance with an embodiment of the present invention.

Although in previous examples, the MEMS folded spring structure includes folded torsion beams perpendicular to the axis of the fiber, a large variety of folded spring designs can be used in different embodiments of the present invention. FIG. 34D illustrates an exemplary design of MEMS folded spring structure wherein the torsion beams are parallel to the optical fibers in accordance with an embodiment of the present invention. In this example, the MEMS folded springs include torsion beams parallel to the axis of the optical fibers. This configuration allows side movements of the structure. Note that the folded spring design in FIG. 34D is only one of many designs that can be used for the MEMS folded spring structure. These different designs are well known to one skilled in the art.

Figure 35A:
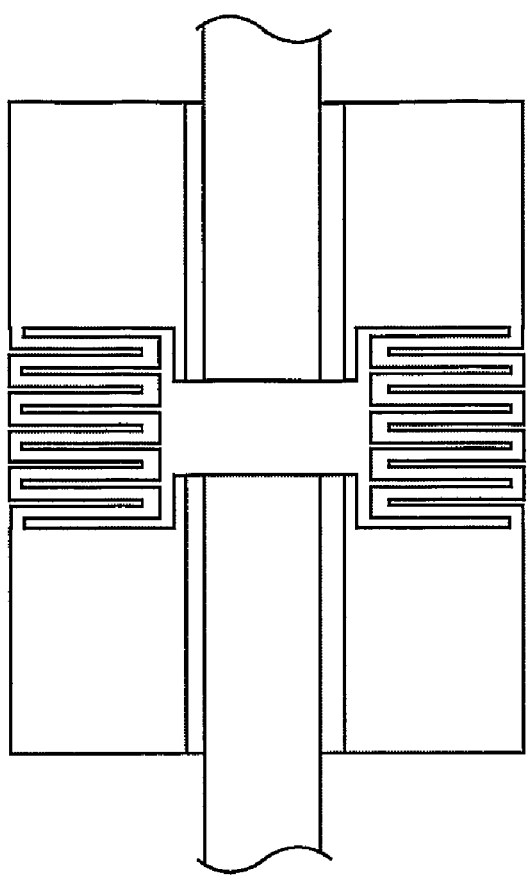
FIG. 35A illustrates a top view of a fiberoptic strain gauge in accordance with an embodiment of the present invention.
Figure 35B:
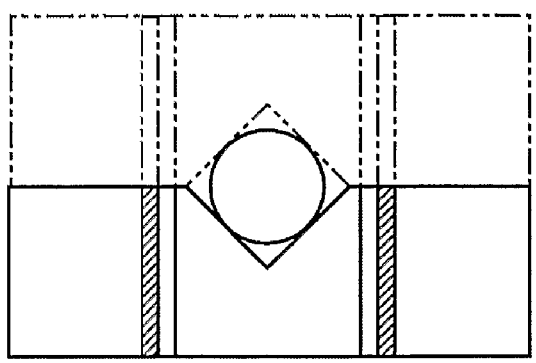
FIG. 35B illustrates a cross-section view of a fiberoptic strain gauge showing a V-groove for fiber alignment in accordance with an embodiment of the present invention.

In one embodiment of the present invention, the input fiber and the reflection/pass-through fiber are held and aligned by a pair of V-grooves. FIG. 35A illustrates a top view of a fiberoptic strain gauge in accordance with an embodiment of the present invention. FIG. 35B illustrates a cross-section view of a fiberoptic strain gauge showing a V-groove for fiber alignment in accordance with an embodiment of the present invention.

The structure shown in FIG. 35A can be fabricated by first etching a V-groove using bulk micromachining techniques and then etching the gap and folded springs using surface micromachining techniques. Bulk micromachining is commonly used to fabricate V-grooves. This fabrication technique is especially advantageous for structures which have characteristic dimensions up to several hundred micrometers and with lengths of up to 20 mm, but nevertheless require an alignment accuracy of better than 1 μm.

During bulk micromachining of the V-groove, first a mask defining the area of the top opening for the V-groove is laid. Next, the silicon wafer is etched anisotropically. Both dry and wet anisotropic etching techniques can be used. These techniques include potassium hydroxide (KOH) etching, tetramethyl ammonium hydroxide (TMAH) etching, ammonia/hydrogen peroxide/water (AHW) etching, ethylenediamine/pyrocathecol/water (EDP) etching, chemical vapor etching, and plasma etching, among others. In one embodiment of the present invention, a V-groove is fabricated on a [100]-silicon wafer with KOH etching.

Once a V-groove is fabricated on a silicon wafer, a gap needs to be cut in the middle of the V-groove and folded springs needs to form on both sides of the gap. This can be achieved by etching through the entire wafer with surface micromachining techniques, such as deep reactive ion etching (DRIE). The etching can be performed either from the front side (the side with the V-groove) or from the back side. In one preferred embodiment of the present invention, the patterning and etching of the gap and folded springs are performed on the back side of the silicon wafer.

As shown in FIG. 35B, in one embodiment, a strain gauge includes two identical MEMS folded spring structures. The upper part and lower part are attached to each other to improve the mechanical reliability of the device. Furthermore, by enclosing the fiber in a top V-groove and a bottom V-groove, the device can ensure that the fiber does not accidentally move out of the V-groove.

Figure 35C:
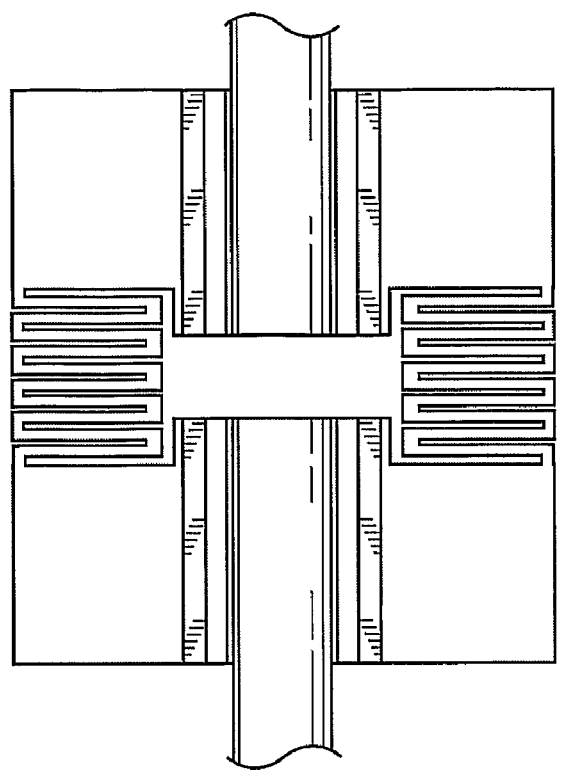
FIG. 35C illustrates a top view of a fiberoptic strain gauge which can bend in two lateral directions in accordance with an embodiment of the present invention.
Figure 35D:
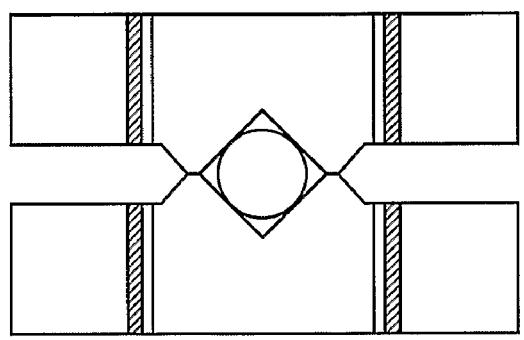
FIG. 35D illustrates a cross-section view of a fiberoptic strain gauge which can bend in two lateral directions in accordance with an embodiment of the present invention.

In one embodiment of the present invention, the thickness of the torsion beams for the folded springs is the same as that of the wafer. This design allows the strain gauge to bend in one lateral direction (i.e., left and right as shown in FIG. 34C and FIG. 35A). However, it is very difficult for the strain gauge to bend in a direction perpendicular to the wafer plane (i.e., in and out of the paper plane in FIG. 35A). This constraint limits the moving range of the strain gauge. One way to mitigate the aforementioned limitation is to reduce the thickness of the torsion beams. FIG. 35C illustrates a top view of a fiberoptic strain gauge which can bend in two lateral directions in accordance with an embodiment of the present invention. FIG. 35D illustrates a cross-section view of a fiberoptic strain gauge which can bend in two lateral directions in accordance with an embodiment of the present invention. As shown in FIG. 35D, the thickness of the folded spring is less than the thickness of the wafer. When an upper structure and a lower structure enclose the fiber, the upper spring and the lower spring do not contact each other. As a result, this design allows the strain gauge to bend around two axes.

The two-axis design allows a strain gauge to be more sensitive to cardiac motions. However, the system cannot tell around which axis is the strain gauge bent. Sometimes it may be desirable to limit the bending of a gauge to only one direction. If this is the case, the single-axis design shown in FIGS. 35A and 35B can be used. Alternatively, two single-axis detection systems can be used simultaneously, so that exact directions of cardiac motions can be accurately detected.

Note that it is also possible to extend the region of folded springs to the space above and below the gap without interfering the light coupling between fibers. Doing so may help further reduce the size of the MEMS holding structure by providing more spring tension using less material for the holding structure.

Figure 36A:
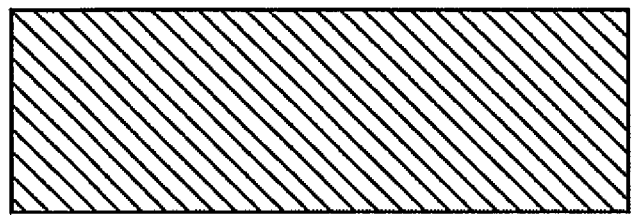
FIGS. 36A-36C illustrates an exemplary fabrication process of a MEMS folded spring structure in accordance with one embodiment of the present invention.
Figure 36B:
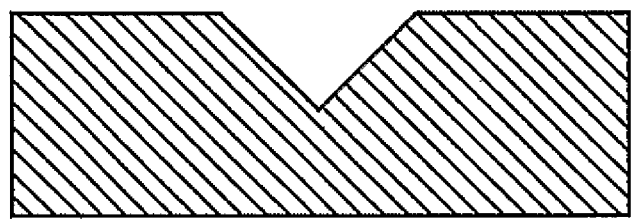
Figure 36C:
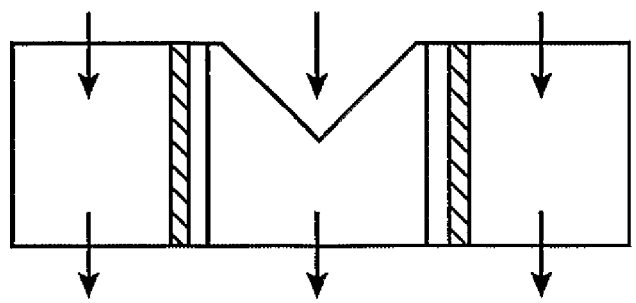

FIGS. 36A-36C illustrate an exemplary fabrication process of a MEMS folded spring structure in accordance with one embodiment of the present invention. FIG. 36A shows an unetched wafer. FIG. 36B shows the V-groove after the wafer is patterned and anisotropically etched. FIG. 36C illustrates a DRIE etching process which produces a gap which turns the V-groove into two separate V-grooves. Furthermore, the DRIE etching also produces folded springs on both sides of the gap allowing the strain gauge to bend laterally.

Figure 37A:
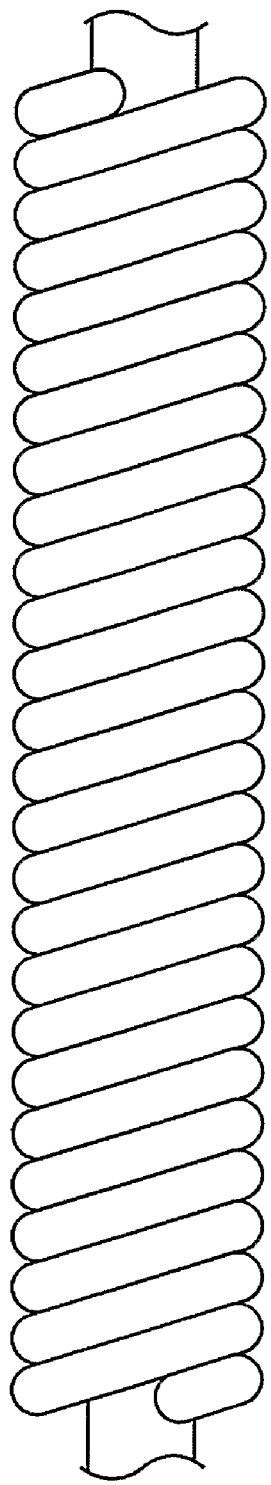
FIG. 37A illustrates an external view of a fiberoptic strain gauge housed in a guide-wire metal coil in accordance with an embodiment of the present invention.

Because of the unprecedented small sizes of the fiberoptic strain gauges, it is possible to place the present cardiac motion detection system within a metal coil which is typically part of a cardiac guidewire. FIG. 37A illustrates an external view of a fiberoptic strain gauge housed in a guide-wire metal coil in accordance with an embodiment of the present invention. In one embodiment, the outer diameter of the metal coil is about 0.025 to 0.6 mm, such as from about 0.1 to 0.5 mm, including from about 0.25 to 0.40 mm. The metal coil can be made of an inert material, which may include stainless steel, platinum, nickel, cobalt, chromium, or an alloy thereof, among others.

Figure 37B:
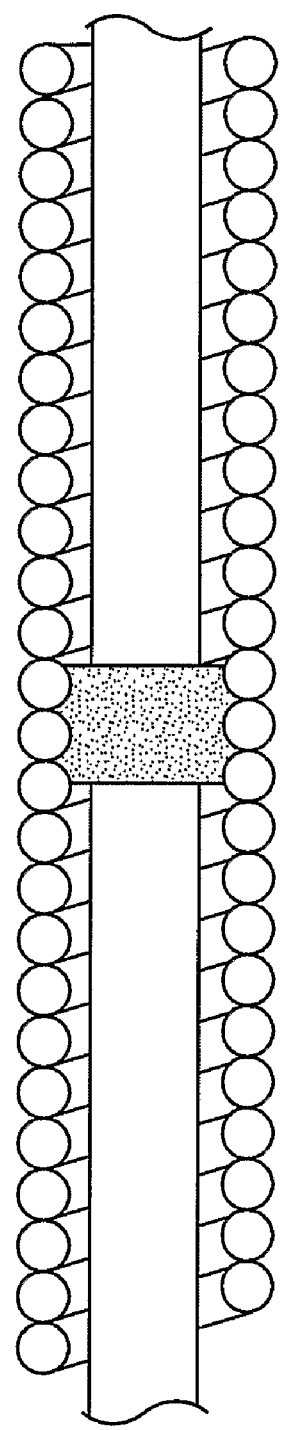
FIG. 37B illustrates an internal view of a fiberoptic strain gauge housed in a guide-wire metal coil in accordance with an embodiment of the present invention.

FIG. 37B illustrates an internal view of a fiberoptic strain gauge housed in a guide-wire metal coil in accordance with an embodiment of the present invention. As shown in FIG. 37B, an input fiber and a reflection/pass-through fiber are enclosed in the metal coil. Between the two fibers is a MEMS folded spring structure submerged in an index-matching material.

Figure 38A:
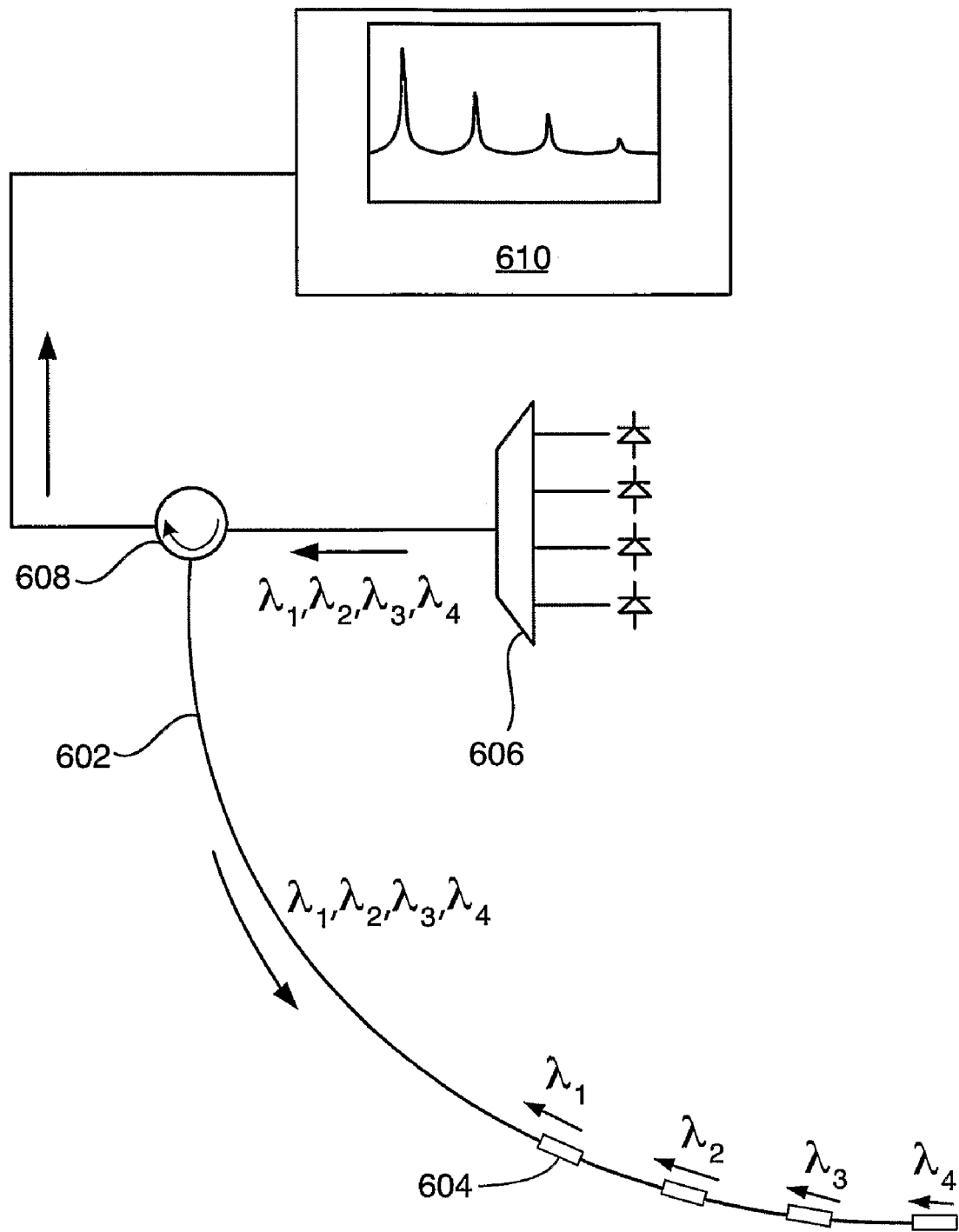
FIG. 38A illustrates a wavelength-division multiplexed (WDM) operation of a number of fiber-optic strain gauges in accordance with an embodiment of the present invention.

FIG. 38A illustrates a wavelength-division multiplexed (WDM) operation of a number of fiber-optic strain gauges in accordance with an embodiment of the present invention. In this example, a main fiber 602 is coupled to four fiberoptic strain gauges, including strain gauge 604. The head end of main fiber 602 is coupled to a number of multiplexed light sources and a spectrum analyzer 610 through an optical circulator 608. As shown in FIG. 38A, four light sources, providing input light at $\lambda_1$, $\lambda_2$, $\lambda_3$, and $\lambda_4$, respectively, are multiplexed by a wavelength-division multiplexer 606. Circulator 608 allows the input light to be coupled to main fiber 602, and allows the light reflected back from the fiberoptic strain gauges to be coupled through a third port to spectrum analyzer 610. Spectrum analyzer 610 displays in real time the intensity of reflected light at different Bragg wavelengths corresponding to each strain gauge. In this way, a physician can time the cardiac motions at locations where each strain gauge is positioned.

FIG. 38A illustrates only one way to implement the present cardiac motion detection system. Alternatives to this embodiment work equally well. For example, the light sources can be lasers or LEDs. Furthermore, the light sources can be individual lasers, or a vertical cavity surface emitting laser (VCSEL) array which is monolithically fabricated and is capable of providing light sources at a number of wavelengths simultaneously.

In another embodiment, instead of multiple individual light sources, one or more tunable lasers can be used. In this case, a tunable laser can be tuned to the Bragg wavelength of a given fiberoptic strain gauge so that its reflected light signals can be monitored. Alternatively, a broadband light source can be used. The use of a broadband light source eliminates the need for a multiplexer. Because each strain gauge reflects only at its Bragg wavelength, the spectrum analyzer can detect these peaks and can therefore easily distinguish the signals corresponding to different strain gauges. Note that a broadband light source does not typically allow adjustment of the output power at specific wavelengths. However, the total output power of the broadband light source can be adjusted for signal-reading of each individual strain gauge to compensate for its accumulated losses.

If individual light sources are used for different Bragg wavelengths, it is possible to automatically adjust the power input at these wavelengths to compensate for the accumulated coupling losses and to fully utilize the dynamic range of the detectors. In one embodiment, the spectrum analyzer is also interfaced with a control module which monitors the absolute power of each of the Bragg wavelengths. If the power at a specific Bragg wavelength is too low, the control module can automatically adjust the power of the light source at that wavelength. As a result, the light detector's dynamic range can be better utilized and a physician can more easily observe the signal variation at that wavelength.

On the signal-detection end, the system alternatively can use a tunable filter coupled with a broadband light detector, such as a PIN diode. This configuration significantly reduces the system cost by avoiding using an expensive spectrum analyzer. During operation, a physician can tune the filter to the Bragg wavelength associated with a specific strain gauge. In another embodiment, the system can also use a demultiplexer and a number of light detectors for each Bragg wavelength.

Figure 38B:
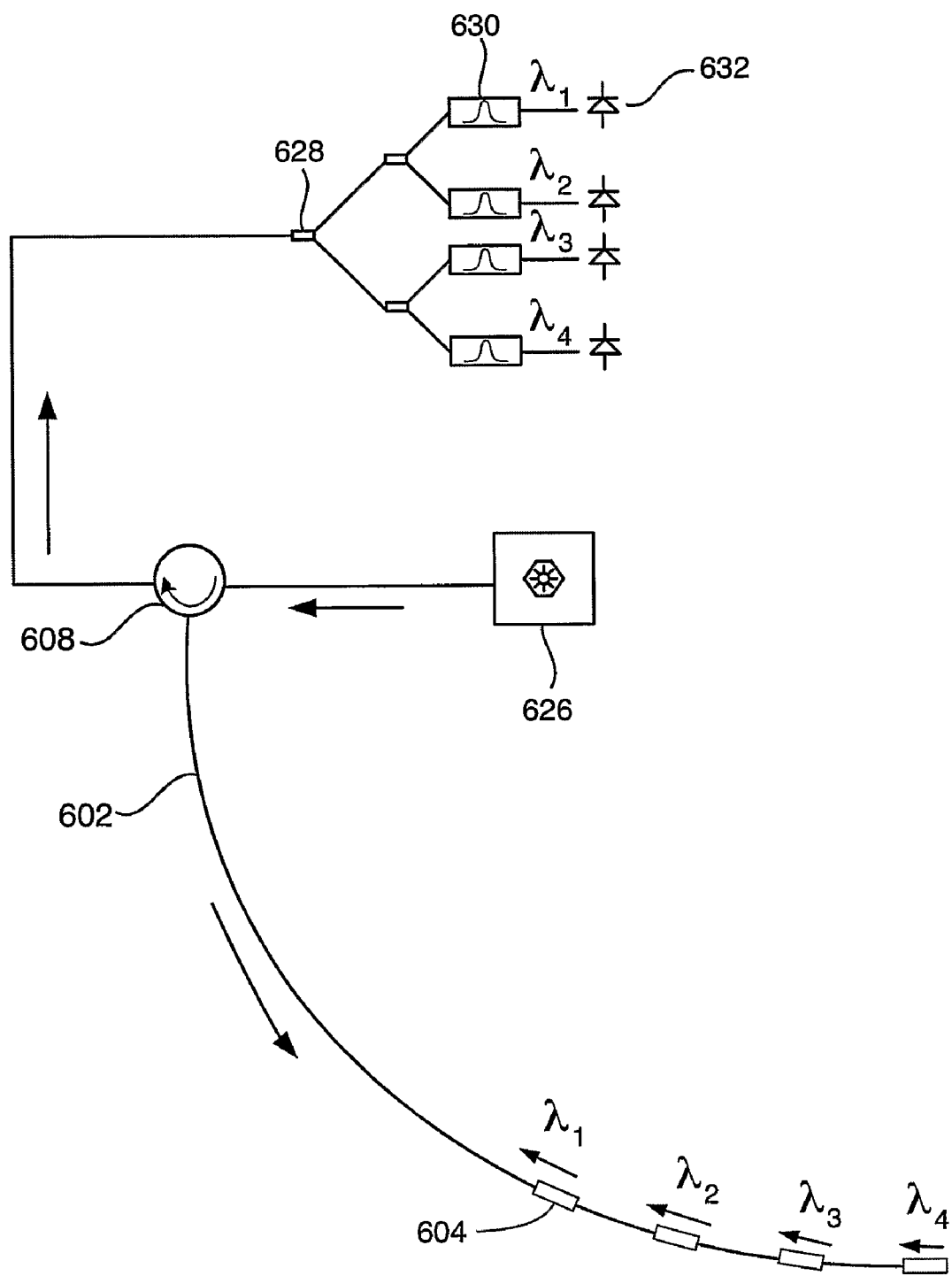
FIG. 38B illustrates a WDM operation of a number of fiber-optic strain gauges with multiple broadband light detectors in accordance with an embodiment of the present invention.

FIG. 38B illustrates a WDM operation of a number of fiber-optic strain gauges with multiple broadband light detectors in accordance with an embodiment of the present invention. In this example, a broadband light source 626 is coupled to main fiber 602 through circulator 608. On the receiving end, a number of 1×2 optical splitters, such as splitter 628, distribute the received signals to four filters, such as filter 630. Each filter selects the Bragg wavelength corresponding to a different strain gauge. Coupled to the filters are four broadband light detectors, such as detector 632, which detect the four Bragg wavelengths.

Figure 39A:
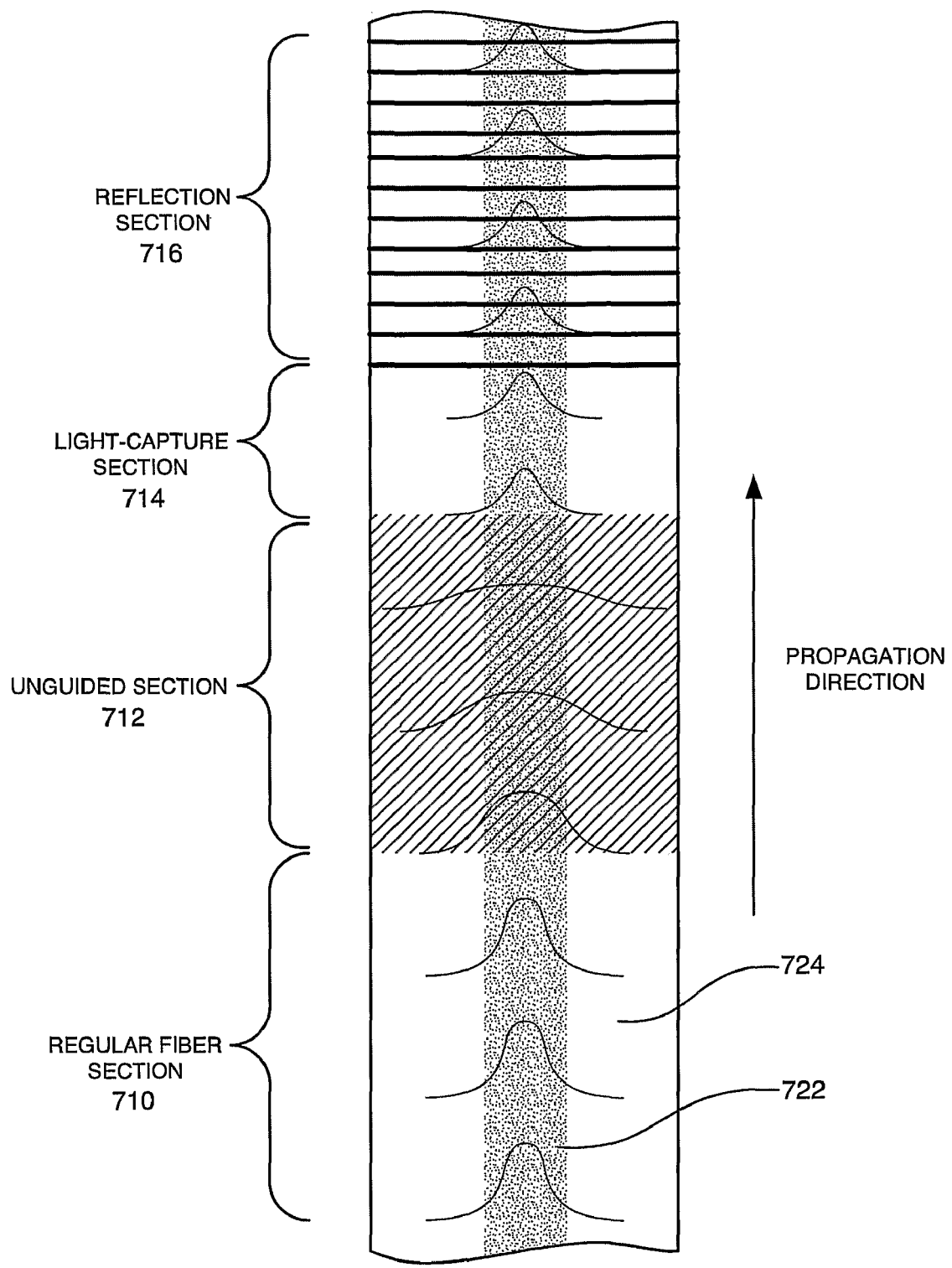
FIG. 39A illustrates a design of fiber-optic strain gauge without a MEMS holding structure in accordance with an embodiment of the present invention.

FIG. 39A illustrates a design of fiber-optic strain gauge without a MEMS holding structure in accordance with an embodiment of the present invention. As shown in FIG. 39A, a fiber-optic strain gauge can be fabricated within one single continuous strand of fiber without any MEMS holding structures. The operation principle of this design, nevertheless, is similar to the aforementioned designs. The fiber in this example has a core 722 and a cladding layer 724. As light enters the regular fiber section 710, its power is well constrained within core 722.

Following regular fiber section 710 is an unguided section 712. In this section, the index of the fiber is changed and the core can no longer fully constrain the power of the propagating wave. The power profile of the light spreads out as light travels forward. At the end of unguided section 712 is a light-capture section 714, which recaptures the spread light. The amount of recaptured light typically depends on the bending incurred on unguided section 712. The more the fiber is bent, the less light can be recaptured.

Following light-capture section 714 is a light reflection section 716. Reflection section 716 contains a fiber Bragg grating which reflects the light at its Bragg wavelength. In this way, by detecting the amount of signal loss at a given Bragg wavelength, the system can detect the amount of bending incurred on the fiber. Note that, in a degenerate design, light-capture section 714 can also be incorporated into reflection section 716 wherein the Bragg grating region also serves to recapture the spread light.

The unguided section can be fabricated using an exposure process similar to that used for fabricating Bragg gratings using the same mask. Alternatively, the exposure process for the unguided region can be a separate process using a different mask. In general, the distance between the Bragg grating and the unguided section is not critical. Therefore, the separate-exposure approach can also enjoy a larger tolerance.

Figure 39B:
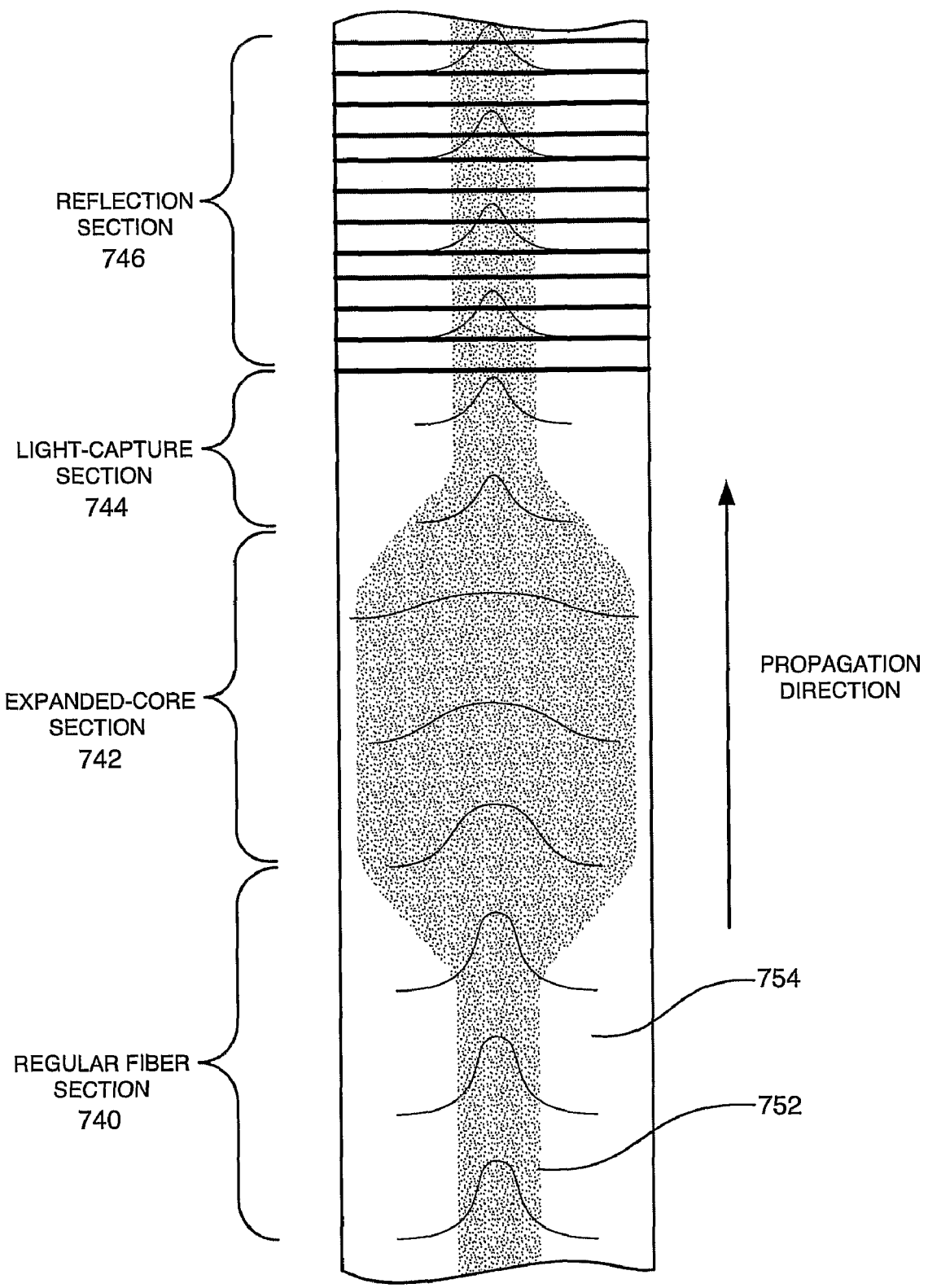
FIG. 39B illustrates another design of fiber-optic strain gauge without a MEMS holding structure in accordance with an embodiment of the present invention.

FIG. 39B illustrates another design of fiber-optic strain gauge without a MEMS holding structure in accordance with an embodiment of the present invention. The fiber in this example has a core 752 and a cladding layer 754. As light enters the regular fiber section 740, its power is well constrained within core 742.

Following regular fiber section 740 is an expanded-core section 742. In this section, the core is expanded and the power of the propagating light spreads out accordingly. This tapered-core structure can be obtained by exposing the fiber to a high-intensity laser. The temperature change induced by the exposure in the targeted region typically expands the core to a tapered shape as shown in FIG. 39B. At the end of expanded-core section 742 is a light-capture section 744, which recaptures the spread light. Following light-capture section 744 is a light reflection section 746. Reflection section 746 contains a fiber Bragg grating which reflects the light at its Bragg wavelength. This design may further reduce the complexity of fabrication of the strain gauge by avoiding an exposure process for the unguided section.

Resonant Marker Band Bending Sensor

Since electrically conductive platinum marker bands are inherently integral components of a catheter-based system, these bands make ideal candidates for elements of a simple strain measurement device. In one embodiment of the present invention, a marker band 200 is created that contains two metal rings 201 and 202 separated by either a compliant insulator or a piezoelectric material 203 as shown in FIG. 25A. The ring structure is then slid over the outside of a catheter 204 and glued in place. Electrical connection to the marker band can be accomplished in a number of ways well know to the ordinary skilled artisan, such as made via wires embedded in the catheter wall.

The marker band is then driven into resonance by either electrostatic attraction between the metal components or by piezoelectric actuation of the piezoelectric material. The resonant frequency of the band shifts as the catheter is bent and the shape of the compliant insulator/piezoelectric material changes, as shown in FIG. 25B.

Piezoelectric Resonant Bending Sensor and Other Piezoelectric Embodiments

In two additional embodiments of the present invention, a piezoelectric approach is provided. In the first approach, strain is sensed by monitoring the shift in the resonant frequency of a piezoelectric crystal 210 mounted in the catheter/guidewire 212, as shown in FIGS. 26A and 26B. In the second instance, strain is sensed by measuring the voltage generated by a piezoelectric material that is put under stress due to bending of the catheter/guidewire. Both embodiments rely upon a bulk piece of piezoelectric material molded or mounted into the catheter/guidewire such that it is stressed when the catheter is bent, as shown in FIGS. 26A and 26B.

For the first piezoelectric approach, the piezoelectric crystal is driven into resonance by an AC voltage source. Bending the crystal will change its resonant frequency, regardless of position in the device. The resonant frequency may be measured using a frequency counter.

A second piezoelectric approach utilizes a bulk piece of piezoelectric material. When a mechanical stress is applied to a piezoceramic element in the longitudinal direction (parallel to polarization), a voltage is generated which tries to return the piece to its original thickness. That voltage may be measured by an AND after it has been amplified and filtered.

Both approaches promise a greater signal to noise ratio which means the crystal does not need to be mounted off of the neutral axis (something that must be done for other strain gauges). More common piezoresistive elements should be located at the place of maximum strain, such as the outer edge of the device. Positioning a strain sensor in the outer wall of a catheter or guidewire may prove difficult as this location is typically used for wire coils or other catheter/guidewire components. The sensor element could be mounted closer to the neutral axis of bending in the lumen of a catheter or guidewire and still produce a measurable response.

Both approaches also promise simpler sensor construction. Unlike resistive strain gauges, there is not a need to etch precision resistors. Both approaches require relatively simple measurement so the practitioner's choice between the two ideas depends on material cost, power requirements and signal to noise ratio.

Capacitive Marker Band Bending Sensor

Since electrically conductive platinum marker bands are already integral components of a catheter-based system, the bands make ideal candidates for elements of a simple strain measurement device. Two marker bands 221 and 222 could be placed in close proximity on a catheter as shown FIG. 27A, and the resulting capacitance between the two bands could be measured. This capacitance will change as the catheter is bent, indicating motion of catheter, as shown FIG. 27B. The marker bands could be either a single conductor or segmented. The single conductor versions would use the change in capacitance in the fringe fields surrounding the bands. The segmented versions, as shown in FIGS. 28A, B and C, are able to indicate direction of bending as well as magnitude. In the segment version, bands 231 and 232 are positioned around guidewire 230, where each segmented band includes marker band metal regions 234 separated by insulator regions 236.

Coupling Strain Gauge Timing Measurements with Mechanical Measurements at a Second Location In certain embodiments, the subject methods and system include employing strain gauges to determining timing of tissue movement at a first location or series of locations, and then employing a second movement characterization element, such as a mechanical characterization element, at a second tissue location. For example, certain embodiments including using strain gauges to detecting timing of tissue movement a left ventricle wall location and an inductive sensing element at a septal wall location, such as is described in U.S. Provisional Patent Application Ser. No. 60/638,947 filed Dec. 22, 2004 titled "Septal Dynamics Measurement Device." In these embodiments, a magnetic coil septal dynamic measurement apparatus provides data which is used synergistically with cardiac wall motion data retrieved from a string of strain gauges.

The magnetic coil septal dynamic measurement apparatus includes a transmitter coil and a receiver coil in an inductive coupling relationship. The transmitter coil is positioned on one surface of the septal wall, e.g., the right ventricular surface. In representative embodiments, the transmitter coil has 0.1 to 1 cm, such as 0.5 cm diameter. The receiver coil has a spiral configuration, and is threaded through the septal wall from a location close the right ventricular surface to a location close to the left ventricular surface, such that the overall length of the spiral receiver coil changes as a function of septal wall thickness. As such, when the septal wall is relaxed, the spiral receiver coil has an extended configuration such that all of the turns in the receiver coil can pick up magnetic flux from the transmitter coil. However, in the contracted state, only a fraction of the turns, e.g., half of the turns, are available to pick up magnetic flux. In representative embodiments, the number of coils ranges from about 5 to about 15, such as 10. As such, the voltage in the receiver coil varies detectably between the relaxed and contracted states, and detection of this variation is readily employed to determine timing of contraction and relaxation of the septal wall. Any convenient approach may be employed to detect the change in voltage, such as a sliding contact connection, where the coil ends to be contacted are insulated but for the distal end, which has a sufficiently large diameter exposed tip to provide for current flow across any resistive medium, e.g., tissue, separating the ends. For implantation of the coils, biodegradeable coatings that provide for desired stiffness during delivery but then degrade to leave a flexible coil may be employed.

In a first embodiment of such a system, the septal dynamic measurement apparatus provides data which is used synergistically with data retrieved from a string of strain gauges inserted into the venous system of the left ventricle outer wall. The strain gauge date is leveraged and informed by the inductive contraction measuring device. The inductive contraction measuring device is inserted into the septum by a catheter, in some cases passing through the vena cava.

When the heart goes from diastole to systole, the heart muscles contract producing a thickening of the ventricular wall and the septum. The contraction reduces the overall size of the heart introducing therefore increased curvature into the outer walls of the heart. The string of strain gauges in the left ventricular venous system in the present invention measure their curvature. When that curvature is followed over time, this data allows observation of the timing of the contraction of the ventricular wall and, in particular, the observation of the timing of the maximum and minimum contractions.

To measure left ventricular efficiency, a second measurement is made at a second site, e.g., a site on the cardiac septum. The inductive muscle contraction monitor is inserted into the second site, e.g., the septal site. Septal wall motion contraction is then monitored. From this data, the time course of the contraction of the septum can be easily determined on an on-going real time basis.

The signals from the two sensing devices, i.e., the strain gauges and the septal wall monitor, can be compared and their degree of synchrony established. When the resynchronization theory is optimal, ideally the contraction of the ventricular wall and the septum will be synchronous, or a least enjoy a clinically useful increase in synchrony.

Based on the data obtained with these two sensing systems, a biventricular stimulation system will have appropriate reference points where the relative timing of the left and right ventricular stimuli can be varied until maximum synchrony is obtained.

An alternative embodiment of the present inventive cardiac wall timing system would have an inductive muscle contraction monitor inserted into the outer wall of the right ventricle. In certain embodiments, muscle contraction monitors are provided in both the septum and the right ventricular wall. This inventive orientation allows comparison of contractility of the right ventricular outer wall with the contractions of the left ventricular wall as measured by the string of strain gauges.

The timing of the contractions is the important parameter to be extracted from the observations of the signals from the strain gauges and the muscle contraction monitors. These observations can be used in turn to optimize the stimulus parameters.

In a representative embodiment, a string of strain gauges is positioned along the left ventricular wall such that they extend down the wall of the left ventricle. A muscle contract monitoring device, e.g., as described above, is inserted in the septal wall. In a variation of this configuration, an additional muscle contraction monitor is inserted into the right ventricular wall Utility The subject methods of evaluating tissue location movement find use in a variety of different applications. As indicated above, an important application of the subject invention is for use in cardiac resynchronization, or CRT, also termed biventricular pacing. As is known in the art, CRT remedies the delayed left ventricular mechanics of heart failure patients. In a desynchronized heart, the interventricular septum will often contract ahead of portions of the free wall of the left ventricle. In such a situation, where the time course of ventricular contraction is prolonged, the aggregate amount of work performed by the left ventricle against the intraventricular pressure is substantial. However, the actual work delivered on the body in the form of stroke volume and effective cardiac output is lower than would otherwise be expected. Using the subject approach, the electromechanical delay of the left lateral ventricle can be evaluated and the resultant data employed in CRT, e.g., using the approaches reviewed above and/or known in the art and reviewed at Col. 22, lines 5 to Col. 24, lines 34 of U.S. Pat. No. 6,795,732, the disclosure of which is herein incorporated by reference.

In a fully implantable system the location of the pacing electrodes on multi electrode leads and pacing timing parameters are continuously optimized by the pacemaker. The pacemaker frequently determines the location and parameters which minimizes intraventricular dyssynchrony, interventricular dyssynchrony, or electromechanical delay of the left ventricle lateral wall in order to optimize CRT. This cardiac wall motion sensing system can also be used during the placement procedure of the cardiac leads in order to optimize CRT. An external controller could be connected to the cardiac leads and a skin patch electrode during placement of the leads. The skin patch acts as the reference electrode until the pacemaker is connected to the leads. In this scenario, for example, the optimal left ventricle cardiac vein location for CRT is determined by acutely measuring intraventricular dyssynchrony.

The subject methods and devices can be used to adjust a resynchronization pacemaker either acutely in an open loop fashion or on a nearly continuous basis in a closed loop fashion.

Other uses for this system could be as an ischemia detector. It is well understood that in the event of acute ischemic events one of the first indications of such ischemia is akinesis, i.e., decreased wall motion of the ischemic tissue as the muscle becomes stiffened. A Wall motion system would be a very sensitive indicator of an ischemic process, by ratio metrically comparing the local wall motion to a global parameter such as pressure; this has been previously described in another Proteus patent. One can derive important information about unmonitored wall segments and their potential ischemia. For example, if an unmonitored section became ischemic, the monitored segment would have to work harder and have relatively greater motion in order to maintain systemic pressure and therefore ratio metric analysis would reveal that fact.

Another application of such position indicators that record wall motion would be as a potentially superior arrhythmia detection circuit. Current arrhythmia detection circuits rely on electrical activity within the heart. Such algorithms are therefore susceptible to confusing electrical noise for an arrhythmia. There is also the potential for misidentifying or mischaracterizing arrhythmia based on electrical events when mechanical analysis would reveal a different underlying physiologic process. Therefore the current invention could also be adapted to develop a superior arrhythmia detection and categorization algorithm.

Additional applications in which the subject invention finds use include, but are not limited to: the detection of electromechanical dissociation during pacing or arrhythmias, differentiation of hemodynamically significant and insignificant ventricular tachycardias, monitoring of cardiac output, mechanical confirmation of capture or loss of capture for autocapture algorithms, optimization of multi-site pacing for heart failure, rate responsive pacing based on myocardial contractility, detection of syncope, detection or classification of atrial and ventricular tachyarrhythmias, automatic adjustment of sense amplifier sensitivity based on detection of mechanical events, determination of pacemaker mode switching, determining the need for fast and aggressive versus slower and less aggressive anti-tachyarrhythmia therapies, or determining the need to compensate for a weakly beating heart after therapy delivery (where these representative applications are reviewed in greater detail in U.S. Pat. No. 6,795,732, the disclosure of which is herein incorporated by reference), and the like.

In certain embodiments, the subject invention is employed to overcome barriers to advances in the pharmacologic management of CHF, which advances are slowed by the inability to physiologically stratify patients and individually evaluate response to variations in therapy. It is widely accepted that optimal medical therapy for CHF involves the simultaneous administration of several pharmacologic agents. Progress in adding new agents or adjusting the relative doses of existing agents is slowed by the need to rely solely on time-consuming and expensive long-term morbidity and mortality trials. In addition, the presumed homogeneity of clinical trial patient populations may often be erroneous since patients in similar symptomatic categories are often assumed to be physiologically similar. It is desirable to provide implantable systems designed to capture important cardiac performance and patient compliance data so that acute effects of medication regimen variation may be accurately quantified. This may lead to surrogate endpoints valuable in designing improved drug treatment regimens for eventual testing in longer-term randomized morbidity and mortality studies. In addition, quantitative hemodynamic analysis may permit better segregation of drug responders from non-responders thereby allowing therapies with promising effects to be detected, appropriately evaluated and eventually approved for marketing. The present invention allows for the above. In certain embodiments, the present invention is used in conjunction with the Pharma-informatics system, as described in U.S. Provisional Application Ser. No. 60/676,145 filed on Apr. 28, 2005 and U.S. Provisional Application Ser. No. 60/694,078; the disclosures of which are herein incorporated by reference.

Non-cardiac applications will be readily apparent to the skilled artisan, such as, by example, measuring the congestion in the lungs, determining how much fluid is in the brain, assessing distention of the urinary bladder. Other applications also include assessing variable characteristics of many organs of the body such as the stomach. In that case, after someone has taken a meal, the present invention allows measurement of the stomach to determine that this has occurred. Because of the inherently numeric nature of the data from the present invention, these patients can be automatically stimulated to stop eating, in the case of overeating, or encouraged to eat, in the case of anorexia. The present inventive system can also be employed to measure the fluid fill of a patient's legs to assess edema, or other various clinical applications.

Embodiments of the present invention may also be used for orthopedic procedures, wherein the strain gauges can detect how bones are bending or stretching. For example, the present inventive fiber-optical strain gauges can be used in FES or stimulation of muscles. The advantage herein is that a physician can place a single strand of fiber that runs along the length of a leg and measures various parameters. In other applications, the present inventive strain gauges can be placed in facial bones for plastic surgical purposes which allow observation of changes in dimension over time.

In other applications, the present inventive strain gauges can be used for spinal surgery to assist examination of fused parts of the spine and to detect residual motion between fused parts in which case the fusing has to be redone. Additional applications of embodiments of the present invention include use of the fiber-optical strain gauges within or in the vicinity of organs such as bladders, lungs, and stomachs. By placing multiple strain gauges around the periphery of these organs, a physician can determine the change in their sizes. Embodiments of the present invention allow measurement at multiple points with a single strand of fiber.

Computer Readable Medium

One or more aspects of the subject invention may be in the form of computer readable media having programming stored thereon for implementing the subject methods. The computer readable media may be, for example, in the form of a computer disk or CD, a floppy disc, a magnetic "hard card", a server, or any other computer readable media capable of containing data or the like, stored electronically, magnetically, optically or by other means. Accordingly, stored programming embodying steps for carrying-out the subject methods may be transferred or communicated to a processor, e.g., by using a computer network, server, or other interface connection, e.g., the Internet, or other relay means.

More specifically, computer readable medium may include stored programming embodying an algorithm for carrying out the subject methods. Accordingly, such a stored algorithm is configured to, or is otherwise capable of, practicing the subject methods, e.g., by operating an implantable medical device to perform the subject methods. The subject algorithm and associated processor may also be capable of implementing the appropriate adjustment(s).

Of particular interest in certain embodiments are systems loaded with such computer readable mediums such that the systems are configured to practice the subject methods.

Kits

As summarized above, also provided are kits for use in practicing the subject methods. In certain embodiments, the kits at least include a computer readable medium, as described above. The computer readable medium may be a component of other devices or systems, or components thereof, in the kit, such as an adaptor module, a pacemaker, etc. The kits and systems may also include a number of optional components that find use including but not limited to, implantation devices, etc. In addition, the kits may include various systems or components thereof, as described above.

In certain embodiments of the subject kits, the kits will further include instructions for using the subject devices or elements for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

The following examples are offered by way of illustration and not by way of limitation.

EXPERIMENTAL

I. Introduction

The goal of the strain gauge studies described herein was to demonstrate that strain gauge leads placed in various locations of the heart can provide direct mechanical contractile timing information of the heart. This information is very valuable for the optimization of cardiac resynchronization therapy for heart failure patients.

II. Leads

In a first lead that was used in the following experiments, two strain gauges were placed at the distal end of the strain gauge lead, 3 or 5 cm apart. The first strain gauge was a 120 ohms resistive strain gauge. The strain gauge was constructed by embedding a foil measuring element into the carrier. The overall thickness of the strain gauge was approximately 30 µm. The carrier dimension was 4×1.5 mm and the foil grid was 1.0×0.7 mm. The strain gauge was attached to two conductor wires. The entire resulting construct was inserted into the lumen of an extruded polyurethane tube.

A second strain gauge with conductor wires was also inserted into the polyurethane tubing such that there was spacing of 3 or 5 cm between the strain gauges. A flexible adhesive was injected into the lumen of the polyurethane tubing in order to hold the strain gauges fixed in place. The polyurethane tubing was equivalent to a 5 French catheter which has outer diameter of 1.7 mm. On the most distal tip of the strain gauge lead was a radio opaque marker which was a platinum iridium band adhered into place using a flexible adhesive.

The distal tip of the strain gauge lead was a rounded cap of soft UV stable adhesive. With this construction any deflection of the lead caused the strain gauges, which were embedded within the lumen of the lead, to deflect and display a strain signal.

Another set of strain gauge leads was constructed using Oscor permanent pacing leads with active fixation or screw in tips. These leads were modified by integrating two strain gauges as described above onto the distal portion of the Oscor permanent pacing lead. These leads are referred to as screw in strain gauge leads.

III. Methods

Porcine animal models were used for these studies in a catheterization laboratory with the animals anesthetized. Pressure sensor catheters were placed in both the left ventricle and right ventricle via the femoral artery and the femoral vein. The catheter in the left ventricle was also able to measure volume.

Under fluoroscopy, the radioopaque marker was shown to be placed in the right vectricle. The placement of the strain gauge lead in the right ventricle provides mechanical contractile timing information of the right ventricle free wall and septum.

The screw in strain gauge lead was observed under fluoroscopy to be located in the right ventricle and was fixated on the right ventricle free wall. This placement was set to isolate the mechanical contractile timing information of the right ventricle free wall. A screw in strain gauge lead was also placed on the septum for isolating the mechanical contractile timing information of the septum. A guide catheter was placed into the coronary sinus to provide the placement of a strain gauge lead into one of the cardiac veins of the left ventricle. This placement gives information about contractile activity occurring on the left ventricle free wall.

Once all the pressure and volume sensing catheters and strain gauge leads were placed in the heart, they were connected to a data acquisition system which included LabView Software and National Instrument equipment. Data was sampled at 500 Hertz. The strain gauge signals were filtered using a 100 hertz low pass filter. Strain, pressure, volume, and EKG were all recorded simultaneously.

IV. Results

Figure 29:
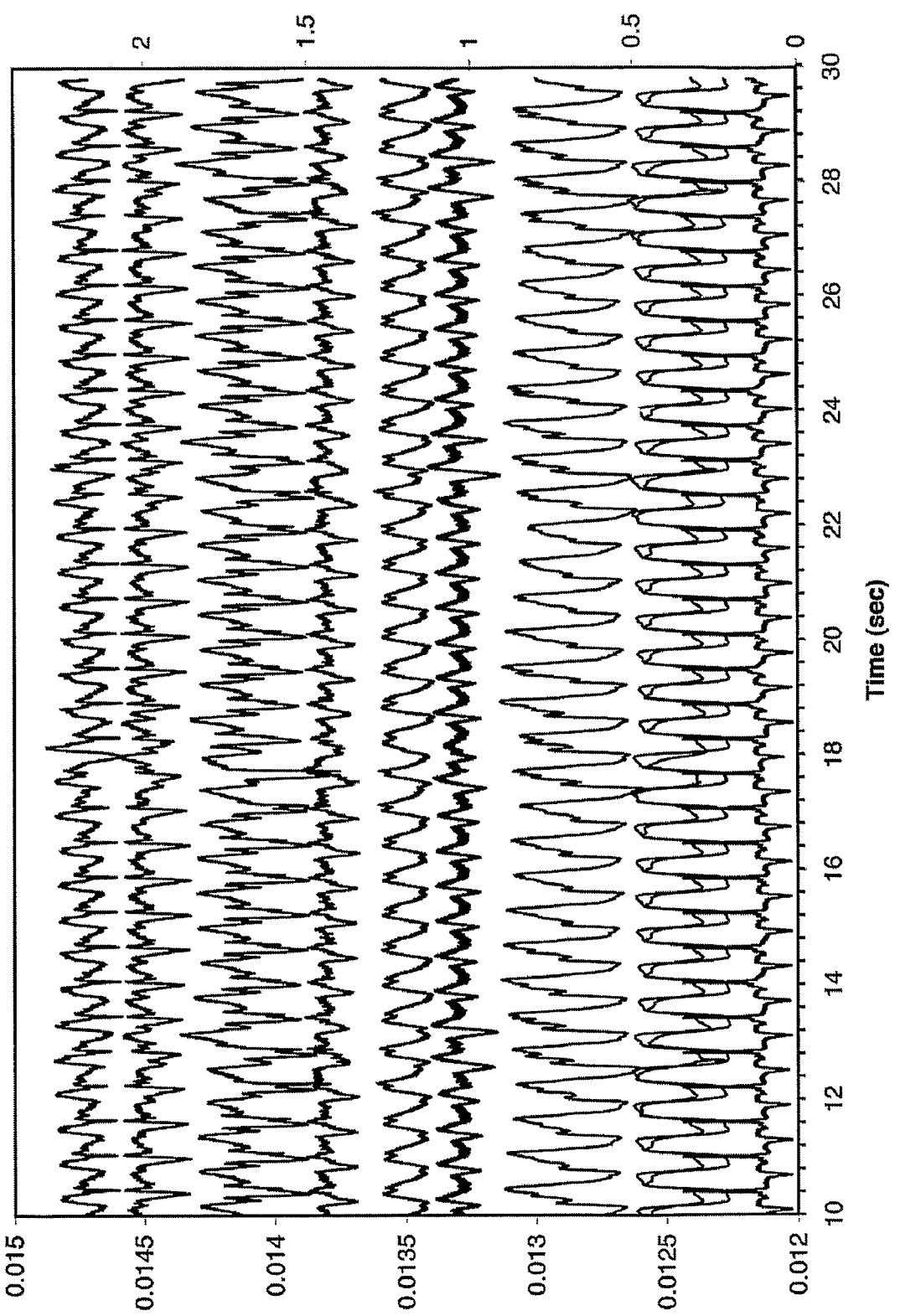
FIGS. 29 to 32 provide graphical results obtained from a strain gauge embodiment of the invention, as reported in the Experimental Section of the application.

FIG. 29 shows the base line results for the strain signals, pressure, volume and EKG vs. time. Looking from the top to the bottom of the chart the curves are defined as follows:
 1. The left ventricle distal strain gauge signal.
 2. The left ventricle proximal strain gauge signal.
 3. The right ventricle distal strain gauge signal.
 4. The right ventricle proximal strain gauge signal.
 5. The right ventricle distal screw in strain gauge signal.
 6. The right ventricle proximal screw in strain gauge signal.
 7. The left ventricle volume (LVV).
 8. The right ventricle pressure (RVP) and the left ventricle pressure (LVP).
 9. The EKG signal.

The results show that all the strain gauges show very repeatable deflections with each cardiac cycle and the periodicity of all the strain gauge signals are clearly tied to the periodicity of the EKG, pressure, and volume signals. Overlaid on top of these curves is the respiration of the pig, which is set at 5 second period by the respirator and shows up as a slight change in amplitude of the strain signals every 5 seconds. This direct correspondence of the periodicity of the strain gauge signals and the heart contractions was also observed in a fluoroscopy video. The strain gauges in the right ventricle and strain ventricle cardiac vein were clearly seen to move and deflect in concert with the cardiac contractions.

Figure 30:
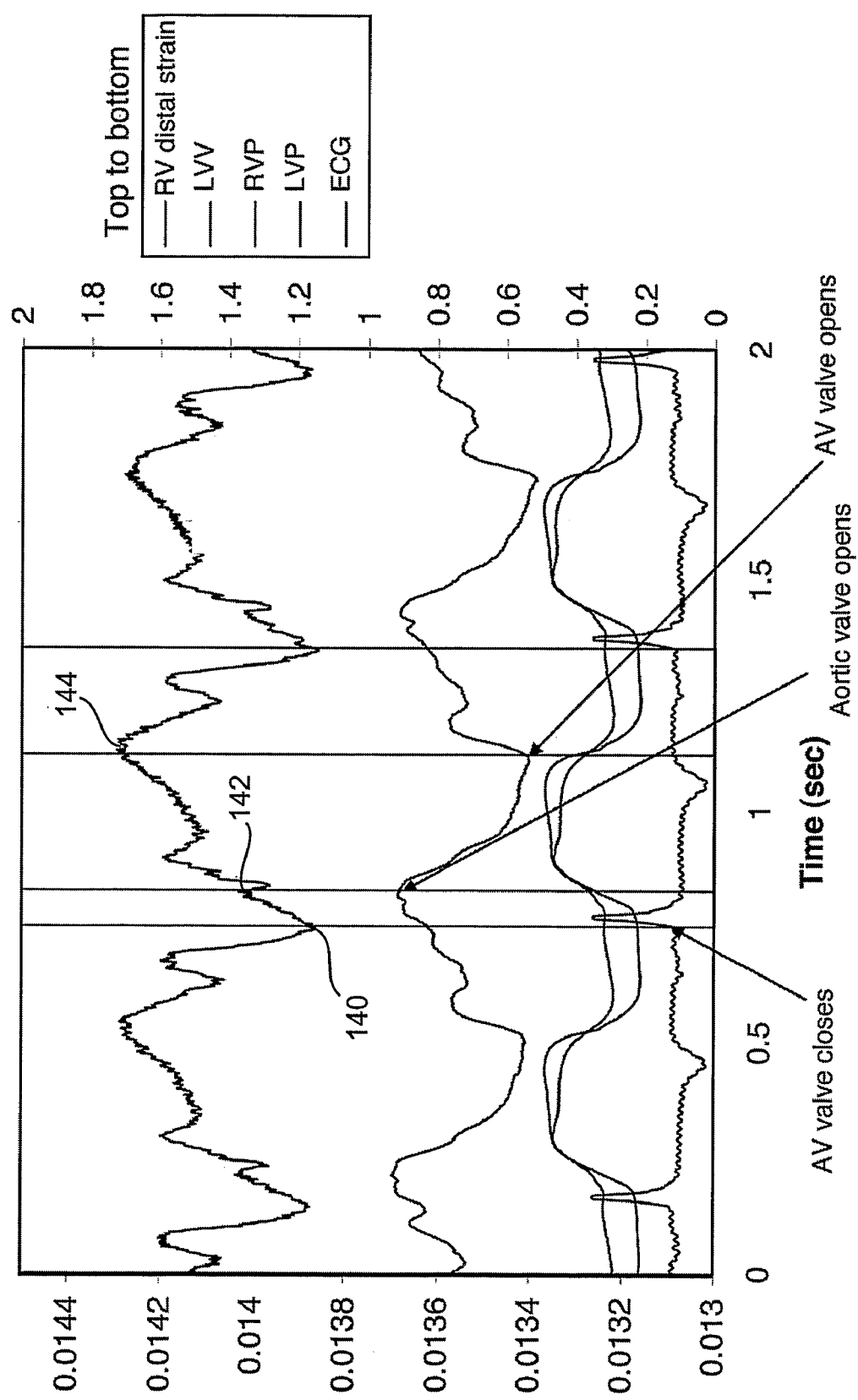

FIG. 30 shows a recording of the right ventricle distal strain gauge, EKG, left and right ventricle pressures, and left ventricle volume as a function of time. Again, very repeatable strain gauge curves are visible between cardiac cycles. The highlighted middle section of the chart represents a single cardiac cycle from the beginning of one QRS cycle, to the beginning of the next QRS cycle. A shape value or minima 140 is seen at the beginning of the QRS when the AV valve closes and iso-volumetric contraction of the ventricle starts.

Before reaching the maxima of the strain signal there is a slight pick-up 142 as visible and appears to coincide with the aortic valve opening. The strain signal reaches its maxima 144 or main peak at the moment when the AV valve opens and the rapid filling of the heart ventricle commences. The strain signal then continues to decrease until it reaches the sharp valley or minima which defines the beginning of the next cardiac cycle.

These results demonstrate that the strain signals provide valuable information, not only about when each cardiac cycle starts or ends, but also as to the various phases within the cardiac cycle which involve opening and closing of heart valves. This data will also elucidate the various phases of the cardiac cycle such as iso-volumetric contraction, rapid ejection, reduced ejection, iso-volumetric relaxation, rapid filling, reduced filling and atrialy systole.

In this experimental testing, the signature shape of the strain gauge signals appears to vary from one strain gauge to another depending on is location. Indeed, a strain gauge lead placed in the cardiac vein on the outside surface of the heart may experience different deflection profiles during the cardiac cycle than a strain gauge lead placed inside or against the endocardiac surface of the right ventricle. It is therefore important to initially study the different strain gauge signal profiles based on their location.

Figure 31:
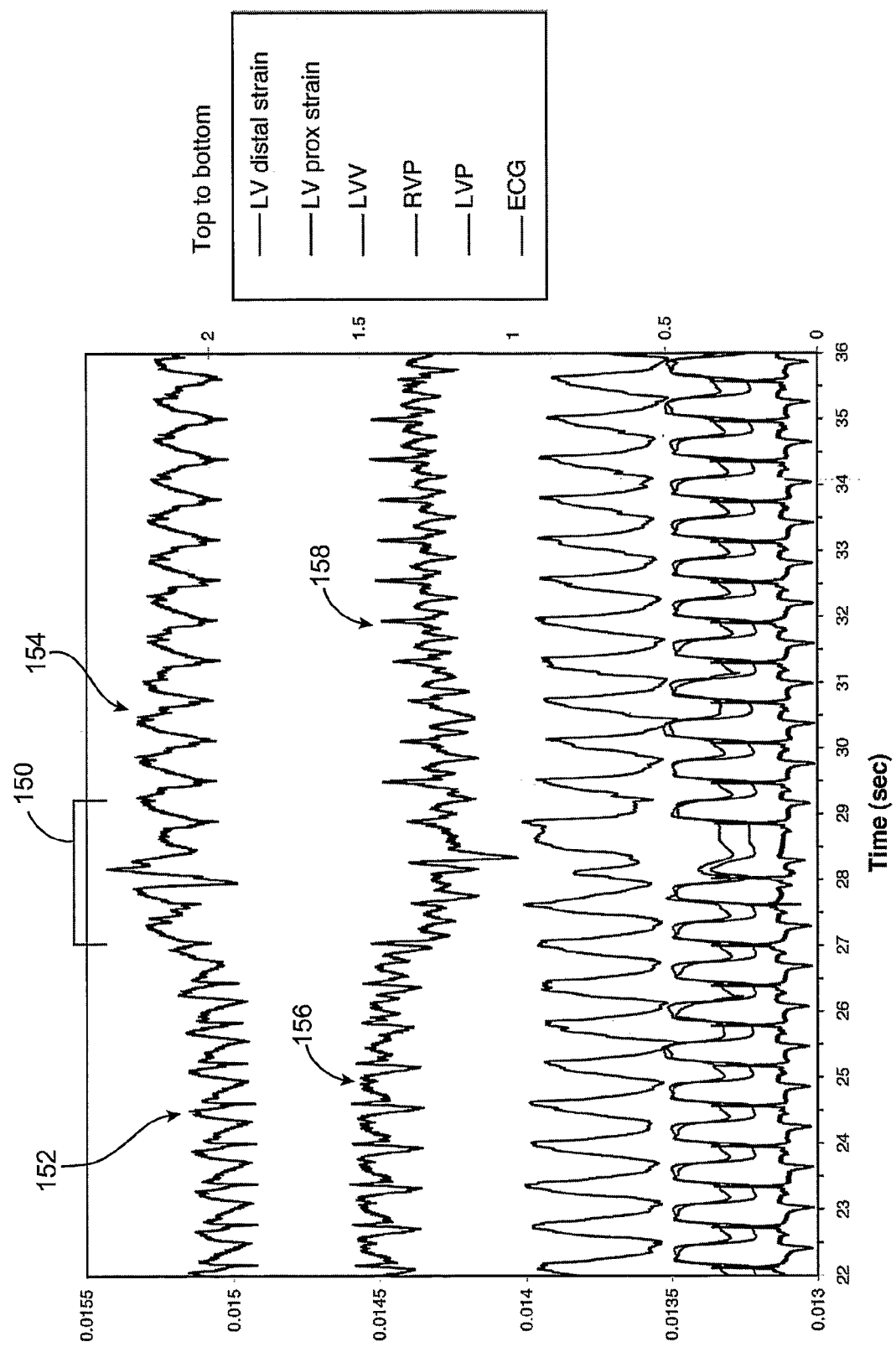

FIG. 31 shows how repositioning the left ventricle strain gauge lead causes a change in the shape and amplitude of the strain signal. The chart includes:
 1. the left ventricle strain gauge signal in dark blue,
 2. the left ventricle proximal strain gauge signal in light blue,
 3. the left ventricle volume measurement in grey,
 4. the left ventricle and
 5. right ventricle pressures in dark pink and light pink, and
 6. at the bottom, the EKG signal in black.

Around the 28 second time mark 150, the strain gauge was repositioned by pulling it back 10 mm within the cardiac vein of the left ventricle. A clear change is visible between the left ventricle distal strain signal 152 before repositioning and the strain signal after repositioning 154. A clear change is also visible to the left ventricle proximal strain gauge in comparing the strain signal before repositioning 156 and after repositioning 158. This sensitivity to location of the strain gauge suggests that having a strain gauge lead with a multiplicity of strain gauges along its length provides for the capture of a comprehensive picture of the strain signals occurring across the heart.

Figure 32:
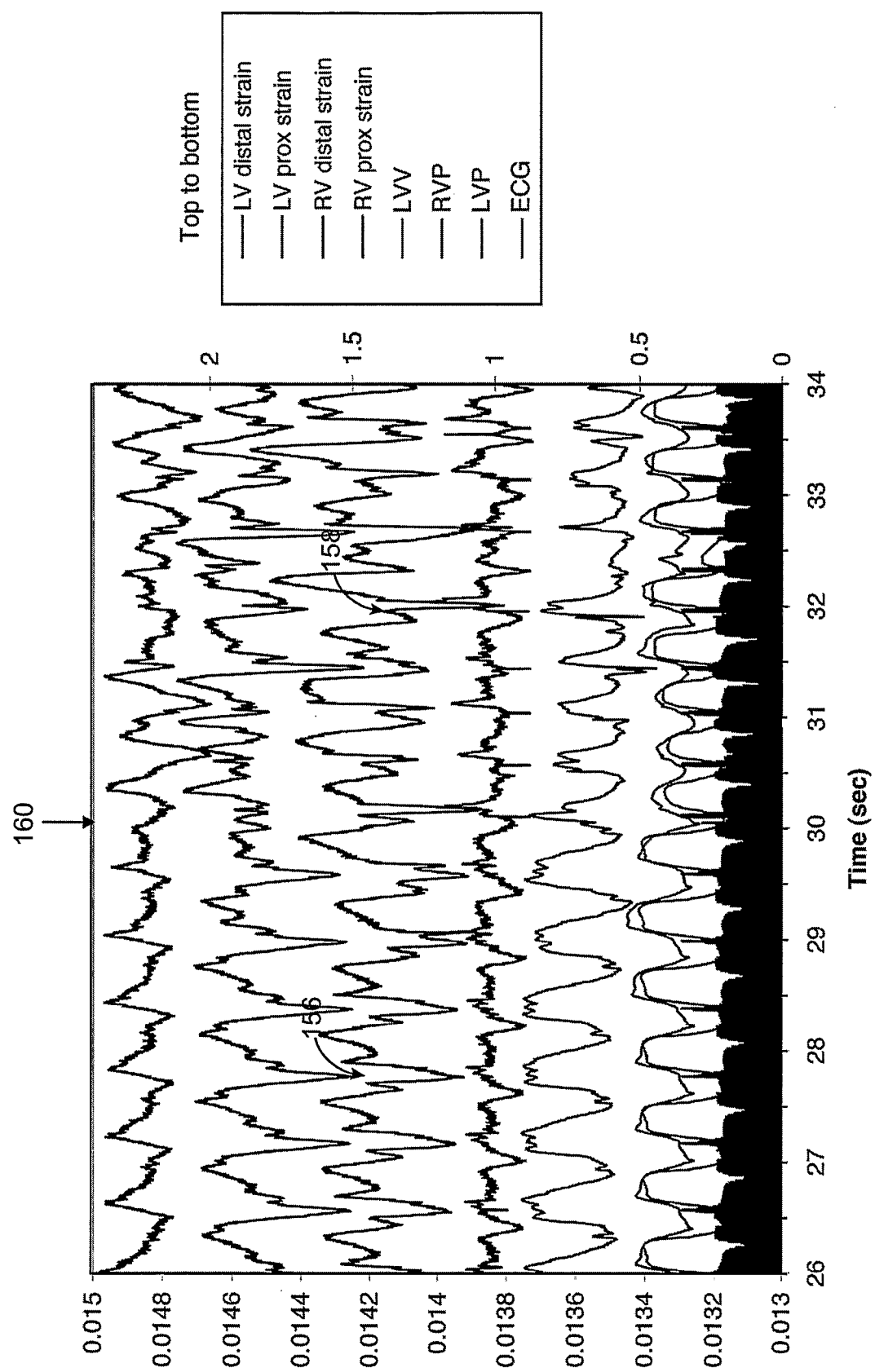

FIG. 32 shows the effect of pacing of the right ventricle screw in lead from top to bottom. The chart shows:
 1. the left ventricle distal strain gauge,
 2. the left ventricle proximal strain gauge,
 3. the right ventricle distal strain gauge,
 4. the right ventricle proximal strain gauge,
 5. the left ventricle volume, 6. the left and right ventricle pressures, and 7. at the bottom, the EKG signal.

Pacing was set at 130 beats per minute and initiated at the 32 second time mark 160. Before pacing was initiated regular strain signals are visible in all the strain gauges. The regularity and shape of the strain gauge signals is disrupted once pacing has been initiated in the right ventricle screw in lead. However it is still possible to observe that the periodicity of the strain gauges has increased from the 98 beats per minute of the base line heart to the 130 beats per minute of the paced heart.

The above data shows a clear timing link between strain gauge signals and the global cardiac contractions of the heart. Current analysis and studies involve investigating the link between the strain gauges and not only global, but regional, mechanical contractile timing of the septum, right and left ventricles. Comparing the strain signals from various signals in the heart allows measurement of dis-synchronous mechanical contractions across the heart of the congestive heart failure patient.

The signal analysis of the strain signals are performed using signal processing techniques such as peak and valley detector algorithms and fast Foley transformations.

As is evident from the above results and discussion, the subject invention provides numerous advantages. Advantages of various embodiments of the subject invention include, but are not limited to: low power consumption; real time discrimination of multiple lines of position possible (one or more); and noise tolerance, since the indicators are relative and mainly of interest in the time domain. A further advantage of this approach is that there is no need for additional catheters or electrodes for determining position. Rather the existing electrodes already used for pacing and defibrillation can be used to inject AC impulses at one or more frequencies designed not to interfere with the body or pacing apparatus. As such, the subject invention represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for evaluating movement of a cardiac tissue location in a subject, the method comprising:
    (a) determining timing of a signal obtained from a resistive strain gauge of an implantable device stably associated with the cardiac tissue location, wherein the implantable device comprises:
    a lead of a length with a proximal end and a distal end, the lead comprising:
    a guide wire core formed within the lead along the length of the lead, wherein the resistive strain gauge is physically attached to the guide wire core; and
    at least one insulated conductor spirally wrapping the guide wire core from the proximal end to the distal end, wherein the resistive strain gauge is electrically coupled to an insulated conductor of the at least one insulated conductor; and
    (b) evaluating movement of the cardiac tissue location via a signal processing element communicatively coupled to the implantable device based on the timing of the signal obtained from the resistive strain gauge.

2. The method according to claim 1, wherein said strain gauge comprises multiple strain tranducers.

3. The method according to claim 1, wherein the resistive strain gauge comprises a substrate.

4. The method according to claim 3, wherein the substrate is compliant.

5. The method according to claim 1, wherein said strain gauge does not include a substrate.

6. The method according to claim 1, wherein said strain gauge comprises a transducer that is hermetically sealed.

7. The method according to claim 1, wherein the resistive strain gauge is not hermetically sealed.

8. The method according to claim 1, wherein the resistive strain gauge comprises a transducer in which strain induces an electric signal.

9. The method according to claim 3, wherein the resistive strain gauge is a fabricated using a resistive material.

10. The method according to claim 9, wherein the resistive material is platinum.

11. The method according to claim 3, wherein said strain transducer is fabricated from a piezoelectric material.

12. The method according to claim 1, wherein said strain gauge comprises a resonant marker band structure.

13. The method according to claim 1, wherein the lead further comprises a tissue securing element configured to stably associate the resistive strain gauge with the cardiac tissue location.

14. The method according to claim 1, wherein the resistive strain gauge is stably associated with the cardiac tissue location by a compressive force.

15. The method according to claim 1, wherein the implantable device is an acute device.

16. The method according to claim 1, wherein the implantable device is present on a permanently implantable device.

17. The method according to claim 1, wherein the cardiac tissue location is a septal wall location.

18. The method according to claim 1, wherein the cardiac tissue location is on a heart wall.

19. The method according to claim 18, wherein the heart wall is a chamber wall.

20. The method according to claim 19, wherein the chamber wall is a ventricular wall.

21. The method according to claim 19, wherein the chamber wall is a septal wall.

22. A system for evaluating movement of a cardiac tissue location, the system comprising:

(a) an implantable device comprising:
a lead of a length with a proximal end and a distal end, the lead comprising:
a guide wire core formed within the lead along the length of the lead;
a resistive strain gauge physically attached to the guide wire core; and
at least one insulated conductor spirally wrapping the guide wire core from the proximal end to the distal end, wherein the resistive strain gauge is electrically coupled to an insulated conductor of the at least one insulated conductor, and the resistive strain gauge stably associated with the cardiac tissue location; and
(b) a signal processing element communicatively coupled to the implantable device and configured to employ timing of a signal obtained from the resistive strain gauge that is induced by movement of the cardiac tissue location to evaluate movement of the cardiac tissue location.

23. An implantable device comprising:
a lead of a length with a proximal end and a distal end, the lead comprising:
a guide wire core formed within the lead along the length of the lead;
a resistive strain gauge physically attached to the guide wire core; and
at least one insulated conductor spirally wrapping the guide wire core from the proximal end to the distal end, wherein the resistive strain gauge is electrically coupled to an insulated conductor of the at least one insulated conductor.

24. The implantable device according to claim 23, wherein the guide wire core is made of a stainless steel or Ni—Ti.

25. The implantable device according to claim 23, wherein the insulated conductor comprises:
a silver core;
a stainless steel wire enclosing the silver core; and
an insulation layer coating the stainless steel wire.

26. The implantable device according to claim 23, further comprising a pacing ring electrode formed at or proximate to the distal end of the lead, wherein the pacing ring electrode is coupled to another insulated conductor of the at least one insulated conductor and is configured to sense an electrical signal and pace a tissue in vicinity.

27. The implantable device according to claim 23, further comprising a catheter enclosing the lead, and wherein the resistive strain gauge is formed on a flap extending from the catheter.

28. The implantable device according to claim 27, wherein the resistive strain gauge formed on the flap is configured to measure a blood flow.

29. The implantable device according to claim 23, wherein the distal end of the lead comprises an umbrella pattern of tines, and wherein the resistive strain gauge is formed at the distal end of the lead.

30. The implantable device according to claim 23, wherein the distal end of the lead comprises a basket type of structure, and wherein the resistive strain gauge is formed at the distal end of the lead.

31. The implantable device according to claim 23, wherein the distal end of the lead comprises a coil, and wherein the resistive strain gauge is formed at the distal end of the lead.

* * * * *